(12) United States Patent
Hennequin

(10) Patent No.: US 7,989,460 B2
(45) Date of Patent: Aug. 2, 2011

(54) QUINAZOLINE DERIVATIVES AS ANGIOGENESIS INHIBITORS

(75) Inventor: Laurent Francois Andre Hennequin, Reims (FR)

(73) Assignee: AstraZeneca AB, Sodertalje (SE)

( * ) Notice: Subject to any disclaimer, the term of this patent is extended or adjusted under 35 U.S.C. 154(b) by 1308 days.

(21) Appl. No.: 10/566,842

(22) PCT Filed: Aug. 5, 2004

(86) PCT No.: PCT/GB2004/003376
§ 371 (c)(1),
(2), (4) Date: Feb. 2, 2006

(87) PCT Pub. No.: WO2005/014582
PCT Pub. Date: Feb. 17, 2005

(65) Prior Publication Data
US 2008/0058342 A1  Mar. 6, 2008

(30) Foreign Application Priority Data

Aug. 6, 2003 (GB) .................................. 0318422.3

(51) Int. Cl.
*A61K 31/517* (2006.01)
(52) U.S. Cl. ...................... 514/266.1; 544/284; 544/287
(58) Field of Classification Search .................. 544/284, 544/287
See application file for complete search history.

(56) References Cited

U.S. PATENT DOCUMENTS

| 7,074,800 B1 | 7/2006 | Stokes et al. |
| 7,268,230 B2 | 9/2007 | Hennequin |
| 2006/0004017 A1 | 1/2006 | Stokes et al. |
| 2008/0027069 A1 | 1/2008 | Hennequin |
| 2009/0156821 A1 | 6/2009 | Hennequin |

FOREIGN PATENT DOCUMENTS

| WO | WO 00/47212 A | 8/2000 |
| WO | WO 03/064413 A | 8/2003 |

*Primary Examiner* — James O Wilson
*Assistant Examiner* — Brian McDowell
(74) *Attorney, Agent, or Firm* — Morgan, Lewis & Bockius LLP

(57) ABSTRACT

The present invention relates to compounds of the formula I:

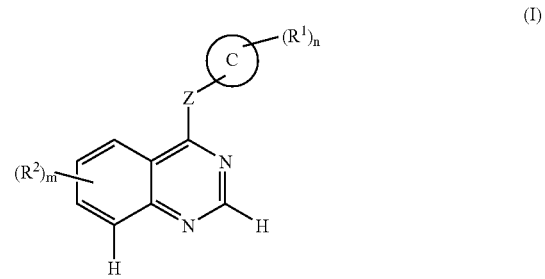

wherein: ring C is an 8, 9, 10, 12 or 13-membered bicyclic or tricyclic moiety which moiety may be saturated or unsaturated, which may be aromatic or non-aromatic, and which optionally may contain 1-3 heteroatoms selected independently from O, N and S; is —O— —NH— or —S—; is 0, 1, 2, 3, 4 or 5; is 0, 1, 2 or 3; and $R^2$ and $R^1$ are as defined herein; and salts thereof; their use in the manufacture of a medicament for use in the production of an antiangiogenic and/or vascular permeability reducing effect in warm-blooded animals; processes for the preparation of such compounds; pharmaceutical compositions containing a compound of formula I or a pharmaceutically acceptable salt thereof and methods of treating disease states involving angiogenesis by administering a compound of formula I or a pharmaceutically acceptable salt thereof. The compounds of formula I inhibit the effects of VEGF, a property of value in the treatment of a number of disease states including cancer and rheumatoid arthritis.

7 Claims, No Drawings

QUINAZOLINE DERIVATIVES AS ANGIOGENESIS INHIBITORS

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844). Basic FGF (bFGF) is a potent stimulator of angiogenesis (e.g. Hayek et al, 1987, Biochem. Biophys. Res. Commun 147: 876-880) and raised levels of FGFs have been found in the serum (Fujimoto et al, 1991, Biochem. Biophys. Res. Commun 180: 386-392) and urine (Nguyen et al, 1993, J. Natl. Cancer. Inst. 85: 241-242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt-1, the kinase insert domain-containing receptor, KDR (also referred to as Flk-1), and another fms-like tyrosine kinase receptor, Flt-4. Two of these related RTKs, Flt-1 and KDR, have been shown to bind VEGF with high affinity (De Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation including macular degeneration.

VEGF is a key stimulus for vasculogenesis and angiogenesis. This cytokine induces a vascular sprouting phenotype by inducing endothelial cell proliferation, protease expression and migration, and subsequent organisation of cells to form a capillary tube (Keck, P. J., Hauser, S. D., Krivi, G., Sanzo, K., Warren, T., Feder, J., and Connolly, D. T., Science (Washington D.C.), 246: 1309-1312, 1989; Lamoreaux, W. J., Fitzgerald, M. E., Reiner, A., Hasty, K. A., and Charles, S. T., Microvasc. Res., 55: 29-42, 1998; Pepper, M. S., Montesano, R., Mandroita, S. J., Orci, L. and Vassalli, J. D., Enzyme Protein, 49: 138-162, 1996). In addition, VEGF induces significant vascular permeability (Dvorak, H. F., Detmar, M., Claffey, K. P., Nagy, J. A., van de Water, L., and Senger, D. R., (Int. Arch. Allergy Immunol., 107: 233-235, 1995; Bates, D. O., Heald, R. I., Curry, F. E. and Williams, B. J. Physiol. (Lond.), 533: 263-272, 2001), promoting formation of a hyper-permeable, immature vascular network which is characteristic of pathological angiogenesis.

It has been shown that activation of KDR alone is sufficient to promote all of the major phenotypic responses to VEGF, including endothelial cell proliferation, migration, and survival, and the induction of vascular permeability (Meyer, M., Clauss, M., Lepple-Wienhues, A., Waltenberger, J., Augustin, H. G., Ziche, M., Lanz, C., Büttner, M., Rziha, H-J., and Dehio, C., EMBO J., 18: 363-374, 1999; Zeng, H., Sanyal, S. and Mukhopadhyay, D., J. Biol. Chem., 276: 32714-32719, 2001; Gille, H., Kowalski, J., Li, B., LeCouter, J., Moffat, B, Zioncheck, T. F., Pelletier, N. and Ferrara, N., J. Biol. Chem., 276: 3222-3230, 2001).

International patent application publication number WO 00/47212 describes VEGF receptor tyrosine kinase inhibitors. Compounds of WO 00/47212 possess activity against VEGF receptor tyrosine kinase (RTK) such that they may be used in an amount sufficient to inhibit VEGF RTK whilst demonstrating no significant activity against EGF RTK. Their VEGF RTK inhibitory activity is due both to activity against KDR and against Flt-1, but generally they are more potent against KDR. Generally they have extended plasma pharmacokinetics. Some VEGF RTK inhibitors have been found to act as potassium channel blockers and are positive in a hERG assay; such activity may give rise to ECG (electrocardiogram) changes in vivo. Compounds of WO 00/47212 have predominantly basic side chains.

Surprisingly we have now found compounds of the present invention to be very potent KDR inhibitors but to have less activity against Flt-1 than compounds of WO 00/47212, to have less extended plasma pharmacokinetics than compounds of WO 00/47212 and to be inactive or only weakly active in a hERG assay. Compounds of the present invention have predominantly neutral side chains. Compounds of the present invention have a beneficial toxicological profile compared to compounds of WO 00/47212.

According to one aspect of the present invention there is provided the use of a compound of the formula I:

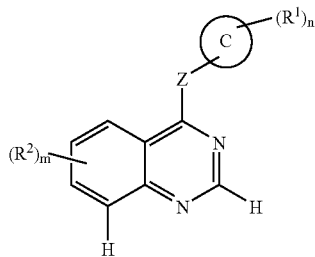

wherein:
ring C is an 8, 9, 10, 12 or 13-membered bicyclic or tricyclic moiety which moiety may be saturated or unsaturated, which may be aromatic or non-aromatic, and which optionally may contain 1-3 heteroatoms selected independently from O, N and S;
Z is —O—, —NH— or —S—;
n is 0, 1, 2, 3, 4 or 5;
m is 0, 1, 2 or 3;
$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —$NR^3R^4$ (wherein $R^3$ and $R^4$, which may be the same or different, each represents hydrogen or $C_{1-3}$alkyl), or $R^5X^1$— (wherein $X^1$ represents a direct bond, —O—, —$CH_2$—, —OC(O)—, —C(O)—, —S—, —SO—, —$SO_2$—, —$NR^6$C(O)—, —C(O)$NR^7$—, —$SO_2NR^8$—, —$NR^9SO_2$— or —$NR^{10}$— (wherein $R^6$, $R^7$, $R^8$, $R^9$ and $R^{10}$ each independently represents hydrogen, $C_{1-3}$alkyl or $C_{1-3}$alkoxy$C_{2-3}$alkyl), and $R^5$ is selected from one of the following twenty-two groups:
1) hydrogen, oxiranyl$C_{1-4}$alkyl or $C_{1-5}$alkyl which may be unsubstituted or which may be substituted with one or more groups selected from hydroxy, fluoro, chloro, bromo and amino;
2) $C_{1-5}$alkyl$X^2$C(O)$R^{11}$ (wherein $X^2$ represents —O— or —$NR^{12}$— (in which $R^{12}$ represents hydrogen, $C_{1-3}$alkyl or $C_{1-3}$alkoxy$C_{2-3}$alkyl) and $R^{11}$ represents $C_{1-3}$alkyl, —$NR^{13}R^{14}$ or —$OR^{15}$ (wherein $R^{13}$, $R^{14}$ and $R^{15}$ which may be the same or different each represents hydrogen, $C_{1-5}$alkyl or $C_{1-3}$alkoxy$C_{2-3}$alkyl));
3) $C_{1-5}$alkyl$X^3R^{16}$ (wherein $X^3$ represents —O—, —S—, —SO—, —$SO_2$—, —OC(O)—, —$NR^{17}$C(O)—, —C(O)$NR^{18}$—, —$SO_2NR^{19}$—, —$NR^{20}SO_2$— or —$NR^{21}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl) and $R^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
4) $C_{1-5}$alkyl$X^4C_{1-5}$alkyl$X^5R^{22}$ (wherein $X^4$ and $X^5$ which may be the same or different are each —O—, —S—, —SO—, —$SO_2$—, —$NR^{23}$C(O)—, —C(O)$NR^{24}$—, —$SO_2NR^{25}$—, —$NR^{26}SO_2$— or —$NR^{27}$— (wherein $R^{23}$, $R^{24}$, $R^{25}$, $R^{26}$ and $R^{27}$ each independently represents hydrogen, $C_{1-3}$alkyl or $C_{1-3}$alkoxy$C_{2-3}$alkyl) and $R^{22}$ represents hydrogen, $C_{1-3}$alkyl or $C_{1-3}$alkoxy$C_{2-3}$alkyl);
5) $R^{28}$ (wherein $R^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
6) $C_{1-5}$alkyl$R^{28}$ (wherein $R^{28}$ is as defined hereinbefore);
7) $C_{2-5}$alkenyl$R^{28}$ (wherein $R^{28}$ is as defined hereinbefore);
8) $C_{2-5}$alkynyl$R^{28}$ (wherein $R^{28}$ is as defined hereinbefore);
9) $R^{29}$ (wherein $R^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)$NR^{30}R^{31}$, —$NR^{32}$C(O)$R^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
10) $C_{1-5}$alkyl$R^{29}$ (wherein $R^{29}$ is as defined hereinbefore);
11) $C_{2-5}$alkenyl$R^{29}$ (wherein $R^{29}$ is as defined hereinbefore);
12) $C_{2-5}$alkynyl$R^{29}$ (wherein $R^{29}$ is as defined hereinbefore);
13) $C_{1-5}$alkyl$X^6R^{29}$ (wherein $X^6$ represents —O—, —S—, —SO—, —$SO_2$—, —$NR^{34}$C(O)—, —C(O)$NR^{35}$—, —$SO_2NR^{36}$—, —$NR^{37}SO_2$— or —$NR^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);
14) $C_{2-5}$alkenyl$X^7R^{29}$ (wherein $X^7$ represents —O—, —S—, —SO—, —$SO_2$—, —$NR^{39}$C(O)—, —C(O)$NR^{40}$—, —$SO_2NR^{41}$—, —$NR^{42}SO_2$— or —$NR^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);
15) $C_{2-5}$alkynyl$X^8R^{29}$ (wherein $X^8$ represents —O—, —S—, —SO—, —$SO_2$—, —$NR^{44}$C(O)—, —C(O)$NR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);
16) $C_{1-4}$alkyl$X^9C_{1-4}$alkyl$R^{29}$ (wherein $X^9$ represents —O—, —S—, —SO—, —$SO_2$—, —$NR^{49}$C(O)—, —C(O)$NR^{50}$—, —$SO_2NR^{51}$—, —$NR^{52}SO_2$— or —$NR^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore);

17) $C_{1-4}$alkyl$X^9 C_{1-4}$alkyl$R^{28}$ (wherein $X^9$ and $R^{28}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^9 C_{1-4}$alkyl$R^{28}$ (wherein $X^9$ and $R^{28}$ are as defined hereinbefore);

21) $C_{2-5}$alkynyl$X^9 C_{1-4}$alkyl$R^{28}$ (wherein $X^9$ and $R^{28}$ are as defined hereinbefore); and 22) $C_{1-4}$alkyl$R^{54}(C_{1-4}$alkyl$)_q(X^9)_r R^{55}$ (wherein $X^9$ is as defined hereinbefore, q is 0 or 1, r is 0 or 1, and $R^{54}$ and $R^{55}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$-aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl$)_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5 X^1$— which is linked to $X^1$ may bear one or more substituents selected from hydroxy, halogeno and amino); $R^1$ represents hydrogen, oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-3}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$ alkylaminosulphonyl, N,N-di($C_{1-4}$alkyl)aminosulphonyl, N—($C_{1-4}$alkylsulphonyl)amino, N—($C_{1-4}$alkylsulphonyl)-N—($C_{1-4}$alkyl)amino, N,N-di($C_{1-4}$alkylsulphonyl)amino, a $C_{3-7}$alkylene chain joined to two ring C carbon atoms, $C_{1-4}$alkanoylamino$C_{1-4}$alkyl, carboxy or a group $R^{56}X^{10}$ (wherein $X^{10}$ represents a direct bond, —O—, —$CH_2$—, —OC(O)—, —C(O)—, —S—, —SO—, —$SO_2$—, —$NR^{57}$C(O)—, —C(O)$NR^{58}$—, —$SO_2 NR^{59}$—, —$NR^{60}$ $SO_2$— or —$NR^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl), and $R^{56}$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkyl$X^{11}$C(O)$R^{62}$ (wherein $X^{11}$ represents —O— or —$NR^{63}$— (in which $R^{63}$ represents hydrogen, $C_{1-3}$alkyl or $C_{1-3}$alkoxy$C_{2-3}$alkyl) and $R^{62}$ represents $C_{1-3}$alkyl, —$NR^{64}R^{65}$ or —$OR^{66}$ (wherein $R^{64}$, $R^{65}$ and $R^{66}$ which may be the same or different each represents hydrogen, $C_{1-5}$alkyl or $C_{1-3}$alkoxy$C_{2-3}$alkyl));

3) $C_{1-5}$alkyl$X^{12}R^{67}$ (wherein $X^{12}$ represents —O—, —S—, —SO—, —$SO_2$—, —OC(O)—, —$NR^{68}$C(O)—, —C(O)$NR^{69}$—, —$SO_2 NR^{70}$—, —$NR^{71}SO_2$— or —$NR^{72}$— (wherein $R^{68}$, $R^{69}$, $R^{70}$, $R^{71}$ and $R^{72}$ each independently represents hydrogen, $C_{1-3}$alkyl or $C_{1-3}$alkoxy$C_{2-3}$alkyl) and $R^{67}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$-aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl$)_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

4) $C_{1-5}$alkyl$X^{13}C_{1-5}$alkyl$X^{14}R^{73}$ (wherein $X^{13}$ and $X^{14}$ which may be the same or different are each —O—, —S—, —SO—, —$SO_2$—, —$NR^{74}$C(O)—, —C(O)$NR^{75}$—, —$SO_2 NR^{76}$—, —$NR^{77}SO_2$— or —$NR^{78}$— (wherein $R^{74}$, $R^{75}$, $R^{76}$, $R^{77}$ and $R^{78}$ each independently represents hydrogen, $C_{1-3}$alkyl or $C_{1-3}$alkoxy$C_{2-3}$alkyl) and $R^{73}$ represents hydrogen, $C_{1-3}$alkyl or $C_{1-3}$alkoxy$C_{2-3}$alkyl);

5) $R^{79}$ (wherein $R^{79}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$-aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl$)_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

6) $C_{1-5}$alkyl$R^{79}$ (wherein $R^{79}$ is as defined hereinbefore);

7) $C_{2-5}$alkenyl$R^{79}$ (wherein $R^{79}$ is as defined hereinbefore);

8) $C_{2-5}$alkynyl$R^{79}$ (wherein $R^{79}$ is as defined hereinbefore);

9) $R^{80}$ (wherein $R^{80}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$-hydroxyalkyl, $C_{1-4}$-aminoalkyl, $C_{1-4}$alkylamino, $C_{1-4}$hydroxyalkoxy, carboxy, trifluoromethyl, cyano, —C(O)$NR^{81}R^{82}$, —$NR^{83}$C(O)$R^{84}$ (wherein $R^{81}$, $R^{82}$, $R^{83}$ and $R^{84}$, which may be the same or different, each represents hydrogen, $C_{1-4}$alkyl or $C_{1-3}$alkoxy$C_{2-3}$alkyl) and a group —(—O—)$_f(C_{1-4}$alkyl$)_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

10) $C_{1-5}$alkylR$^{80}$ (wherein R$^{80}$ is as defined hereinbefore);
11) $C_{2-5}$alkenylR$^{80}$ (wherein R$^{80}$ is as defined hereinbefore);
12) $C_{2-5}$alkynylR$^{80}$ (wherein R$^{80}$ is as defined hereinbefore);
13) $C_{1-5}$alkylX$^{15}$R$^{80}$ (wherein X$^{15}$ represents —O—, —S—, —SO—, —SO$_2$—, —NR$^{85}$C(O)—, —C(O)NR$^{86}$—, —SO$_2$NR$^{87}$—, —NR$^{88}$SO$_2$— or —NR$^{89}$— (wherein R$^{85}$, R$^{86}$, R$^{87}$, R$^{88}$ and R$^{89}$ each independently represents hydrogen, $C_{1-3}$alkyl or $C_{1-3}$alkoxy$C_{2-3}$alkyl) and R$^{80}$ is as defined hereinbefore);
14) $C_{2-5}$alkenylX$^{16}$R$^{80}$ (wherein X$^{16}$ represents —O—, —S—, —SO—, —SO$_2$—, —NR$^{90}$C(O)—, —C(O)NR$^{91}$—, —SO$_2$NR$^{92}$—, —NR$^{93}$SO$_2$— or —NR$^{94}$— (wherein R$^{90}$, R$^{91}$, R$^{92}$, R$^{93}$ and R$^{94}$ each independently represents hydrogen, $C_{1-3}$alkyl or $C_{1-3}$alkoxy$C_{2-3}$alkyl) and R$^{80}$ is as defined hereinbefore);
15) $C_{2-5}$alkynylX$^{17}$R$^{80}$ (wherein X$^{17}$ represents —O—, —S—, —SO—, —SO$_2$—, —NR$^{95}$C(O)—, —C(O)NR$^{96}$—, —SO$_2$NR$^{97}$—, —NR$^{98}$SO$_2$— or —NR$^{99}$— (wherein R$^{95}$, R$^{96}$, R$^{97}$, R$^{98}$ and R$^{99}$ each independently represents hydrogen, $C_{1-3}$alkyl or $C_{1-3}$alkoxy$C_{2-3}$alkyl) and R$^{80}$ is as defined hereinbefore);
16) $C_{1-4}$alkylX$^{18}$$C_{1-4}$alkylR$^{80}$ (wherein X$^{18}$ represents —O—, —S—, —SO—, —SO$_2$—, —NR$^{100}$C(O)—, —C(O)NR$^{101}$—, —SO$_2$NR$^{102}$—, —NR$^{103}$SO$_2$— or NR$^{104}$— (wherein R$^{100}$, R$^{101}$, R$^{102}$, R$^{103}$ and R$^{104}$ each independently represents hydrogen, $C_{1-3}$alkyl or $C_{1-3}$alkoxy$C_{2-3}$alkyl) and R$^{80}$ is as defined hereinbefore);
17) $C_{1-4}$alkylX$^{18}$$C_{1-4}$alkylR$^{79}$ (wherein X$^{18}$ and R$^{79}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-5}$alkenylX$^{18}$$C_{1-4}$alkylR$^{79}$ (wherein X$^{18}$ and R$^{79}$ are as defined hereinbefore);
21) $C_{2-5}$alkynylX$^{18}$$C_{1-4}$alkylR$^{79}$ (wherein X$^{18}$ and R$^{79}$ are as defined hereinbefore); and
22) $C_{1-4}$alkylR$^{105}$($C_{1-4}$alkyl)$_x$(X$^{18}$)$_y$R$^{106}$ (wherein X$^{18}$ is as defined hereinbefore, x is 0 or 1, y is 0 or 1, and R$^{105}$ and R$^{106}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$-aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl) with the proviso that R$^{105}$ cannot be hydrogen);
and additionally wherein any $C_{1-5}$alkyl, $C_{2-5}$alkenyl or $C_{2-5}$alkynyl group in R$^{56}$X$^{10}$— which is linked to X$^{10}$ may bear one or more substituents selected from hydroxy, halogeno and amino);

with the proviso that one or more R$^1$ and/or one or more R$^2$ are selected from Q$^1$X$^1$— wherein X$^1$ is as defined hereinbefore and Q$^1$ is selected from one of the following groups:
1) $C_{1-4}$alkyl-Q$^{13}$-C(O)—$C_{1-4}$alkyl-Q$^{14}$ wherein Q$^{13}$ is $C_{1-3}$alkyl, cyclopentyl, cyclohexyl and a 5-6-membered saturated or partially unsaturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear either one substituent selected from methylenedioxy or ethylenedioxy to form a bicyclic ring, or may bear 1, 2 or 3 substituents selected from $C_{2-5}$alkenyl, $C_{2-5}$alkynyl, $C_{1-6}$fluoroalkyl, $C_{1-6}$alkanoyl, $C_{1-6}$alkanoyl$C_{1-6}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$-alkyl, $C_{1-4}$alkylsulphonyl$C_{1-4}$alkyl, $C_{1-4}$alkoxycarbonyl, $C_{1-4}$-aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl), and Q$^{14}$ is a 5-6-membered saturated or partially unsaturated heterocyclic group containing at least one nitrogen atom and optionally containing a further nitrogen atom wherein Q$^{14}$ is linked to $C_{1-6}$alkanoyl through a nitrogen atom and wherein Q$^{14}$ optionally bears either one substituent selected from methylenedioxy or ethylenedioxy to form a bicyclic ring, or bears 1, 2 or 3 substituents selected from $C_{2-5}$alkenyl, $C_{2-5}$alkynyl, $C_{1-6}$fluoroalkyl, $C_{1-6}$alkanoyl, $C_{1-6}$alkanoyl$C_{1-6}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$-fluoroalkylsulphonyl, oxo, hydroxy, halogeno, cyano, $C_{1-4}$cyanoalkyl, $C_{1-4}$alkyl, $C_{1-4}$-hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl);
2) Q$^2$ (wherein Q$^2$ is a 5-6-membered saturated or partially unsaturated heterocyclic group with 1-2 heteroatoms, selected independently from O, S and N, which heterocyclic group bears either one substituent selected from methylenedioxy or ethylenedioxy to form a bicyclic ring, or bears at least one substituent selected from $C_{1-6}$alkanoyl$C_{1-6}$alkyl and optionally bears a further 1 or 2 substituents selected from $C_{2-5}$alkenyl, $C_{2-5}$alkynyl, $C_{1-6}$fluoroalkyl, $C_{1-6}$alkanoyl, $C_{1-6}$alkanoyl$C_{1-6}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$-fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$-alkyl, $C_{1-4}$alkylsulphonyl$C_{1-4}$alkyl, $C_{1-4}$alkoxycarbonyl, $C_{1-4}$-aminoalkyl, $C_{1-4}$alkylamino, di($C_{1-4}$alkyl)amino, $C_{1-4}$alkylamino$C_{1-4}$alkyl, di($C_{1-4}$alkyl) amino$C_{1-4}$alkyl, $C_{1-4}$alkylamino$C_{1-4}$alkoxy, di($C_{1-4}$alkyl) amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which cyclic group may bear one or more substituents selected from $C_{1-4}$alkyl));

3) $C_{1-5}$alkyl$W^1Q^2$ (wherein $W^1$ represents —O—, —S—, —SO—, —SO$_2$—, —OC(O)—, —NQ$^3$C(O)—, —C(O)NQ$^4$-, —SO$_2$NQ$^5$-, —NQ$^6$SO$_2$— or —NQ$^7$- (wherein $Q^3$, $Q^4$, $Q^5$, $Q^6$ and $Q^7$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl) and $Q^2$ is as defined hereinbefore;

4) $C_{1-5}$alkyl$Q^2$ (wherein $Q^2$ is as defined hereinbefore);

5) $C_{2-5}$alkenyl$Q^2$ (wherein $Q^2$ is as defined hereinbefore);

6) $C_{2-5}$alkynyl$Q^2$ (wherein $Q^2$ is as defined hereinbefore);

7) $C_{1-4}$alkyl$W^2C_{1-4}$alkyl$Q^2$ (wherein $W^2$ represents —O—, —S—, —SO—, —SO$_2$—, NQ$^8$C(O)—, —C(O)NQ$^9$-, —SO$_2$NQ$^{10}$-, —NQ$^{11}$SO$_2$— or —NQ$^{12}$- (wherein $Q^8$, $Q^9$, $Q^{10}$, $Q^{11}$ and $Q^{12}$ each independently represents hydrogen, $C_{1-3}$alkyl, $C_{1-3}$alkoxy$C_{2-3}$alkyl, $C_{2-5}$alkenyl, $C_{2-5}$alkynyl or $C_{1-4}$haloalkyl) and $Q^2$ is as defined hereinbefore);

8) $C_{2-5}$alkenyl$W^2C_{1-4}$alkyl$Q^2$ (wherein $W^2$ and $Q^2$ are as defined hereinbefore);

9) $C_{2-5}$alkynyl$W^2C_{1-4}$alkyl$Q^2$ (wherein $W^2$ and $Q^2$ are as defined hereinbefore);

10) $C_{1-4}$alkyl$Q^{15}(C_{1-4}$alkyl)$_j(W^2)_kQ^{16}$ (wherein $W^2$ is as defined hereinbefore, j is 0 or 1, k is 0 or 1, and $Q^{15}$ and $Q^{16}$ are each independently selected from hydrogen, $C_{1-3}$alkyl, cyclopentyl, cyclohexyl and a 5-6-membered saturated or partially unsaturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear either one substituent selected from methylenedioxy or ethylenedioxy to form a bicyclic ring, or may bear 1, 2 or 3 substituents selected from $C_{2-5}$alkenyl, $C_{2-5}$alkynyl, $C_{1-6}$fluoroalkyl, $C_{1-6}$alkanoyl, amino$C_{1-6}$alkanoyl, $C_{1-4}$alkylamino$C_{1-6}$alkanoyl, di($C_{1-4}$alkyl) amino$C_{1-6}$ alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, di($C_{1-4}$alkyl)amino$C_{1-4}$alkyl, 4alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl), with the provisos that $Q^{15}$ cannot be hydrogen and one or both of $Q^{15}$ and $Q^{16}$ must be a 5-6-membered saturated or partially unsaturated heterocyclic group as defined hereinbefore which heterocyclic group bears either one substituent selected from methylenedioxy or ethylenedioxy to form a bicyclic ring, or bears at least one substituent selected from $C_{1-6}$alkanoyl$C_{1-6}$alkyl and optionally bears 1 or 2 further substituents selected from those defined hereinbefore);

11) $C_{1-4}$alkyl$Q^{15}C_{1-4}$alkanoyl$Q^{16n}$ wherein $Q^{15}$ is as defined hereinbefore and is not hydrogen and $Q^{16n}$ is a 5-6-membered saturated or partially unsaturated heterocyclic group containing at least one nitrogen atom and optionally containing a further nitrogen atom wherein $Q^{16n}$ is linked to $C_{1-6}$alkanoyl through a nitrogen atom and wherein $Q^{16n}$ bears either one substituent selected from methylenedioxy or ethylenedioxy to form a bicyclic ring, or bears 1, 2 or 3 substituents selected from $C_{2-5}$alkenyl, $C_{2-5}$alkynyl, $C_{1-6}$fluoroalkyl, $C_{1-6}$alkanoyl, $C_{1-6}$alkanoyl$C_{1-6}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$ alkyl)amino$C_{1-4}$alkyl, $C_{1-4}$alkylamino$C_{1-4}$alkoxy, di($C_{1-4}$ alkyl)amino$C_{1-4}$alkoxy and a group —(—O—)$_f$($C_{1-4}$ alkyl)$_g$ ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl); with the proviso that one or both of $Q^{15}$ and $Q^{16n}$ must be a 5-6-membered saturated or partially unsaturated heterocyclic group as defined hereinbefore which heterocyclic group bears either one substituent selected from methylenedioxy or ethylenedioxy to form a bicyclic ring, or bears at least one substituent selected from $C_{1-6}$alkanoyl$C_{1-6}$alkyl and optionally bears 1 or 2 further substituents selected from those defined hereinbefore;

and additionally wherein any $C_{1-5}$alkyl, $C_{2-5}$alkenyl or $C_{2-5}$alkynyl group in $Q^1X^1$— which is linked to $X^1$ may bear one or more substituents selected from hydroxy, halogeno and amino); or a salt thereof, or a prodrug thereof for example an ester or an amide, in the manufacture of a medicament for use in the production of an antiangiogenic and/or vascular permeability reducing effect in warm-blooded animals such as humans.

According to one aspect of the present invention there is provided the use of a compound of the formula I:

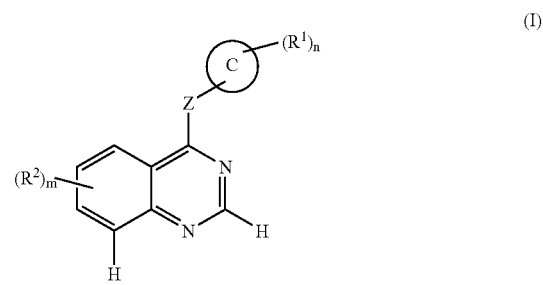

wherein:
ring C is an 8, 9, 10, 12 or 13-membered bicyclic or tricyclic moiety which moiety may be saturated or unsaturated, which may be aromatic or non-aromatic, and which optionally may contain 1-3 heteroatoms selected independently from O, N and S;
Z is —O—, —NH— or —S—;
n is 0, 1, 2, 3, 4 or 5;
m is 0, 1, 2 or 3;

$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —$NR^3R^4$ (wherein $R^3$ and $R^4$, which may be the same or different, each represents hydrogen or $C_{1-3}$alkyl), or $R^5X^1$— (wherein $X^1$ represents a direct bond, —O—, —$CH_2$—, —OC(O)—, —C(O)—, —S—, —SO—, —$SO_2$—, —$NR^6$C(O)—, —C(O)$NR^7$—, —$SO_2NR^8$—, —$NR^9SO_2$— or —$NR^{10}$— (wherein $R^6$, $R^7$, $R^8$, $R^9$ and $R^{10}$ each independently represents hydrogen, $C_{1-3}$alkyl or $C_{1-3}$alkoxy$C_{2-3}$alkyl), and $R^5$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkyl$X^2$C(O)$R^{11}$ (wherein $X^2$ represents —O— or —$NR^{12}$— (in which $R^{12}$ represents hydrogen, $C_{1-3}$alkyl or $C_{1-3}$alkoxy$C_{2-3}$alkyl) and $R^{11}$ represents $C_{1-3}$alkyl, —$NR^{13}R^{14}$ or —$OR^{15}$ (wherein $R^{13}$, $R^{14}$ and $R^{15}$ which may be the same or different each represents hydrogen, $C_{1-5}$alkyl or $C_{1-3}$alkoxy$C_{2-3}$alkyl));

3) $C_{1-5}$alkyl$X^3R^{16}$ (wherein $X^3$ represents —O—, —S—, —SO—, —$SO_2$—, —OC(O)—, —$NR^{17}$C(O)—, —C(O)$NR^{18}$—, —$SO_2NR^{19}$—, —$NR^{20}SO_2$— or —$NR^{21}$— (wherein $R^{17}$, $R^{18}$, $R^{19}$, $R^{20}$ and $R^{21}$ each independently represents hydrogen, $C_{1-3}$alkyl or $C_{1-3}$alkoxy$C_{2-3}$alkyl) and $R^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

4) $C_{1-5}$alkyl$X^4C_{1-5}$alkyl$X^5R^{22}$ (wherein $X^4$ and $X^5$ which may be the same or different are each —O—, —S—, —SO—, —$SO_2$—, —$NR^{23}$C(O)—, —C(O)$NR^{24}$—, —$SO_2NR^{25}$—, —$NR^{26}SO_2$— or —$NR^{27}$— (wherein $R^{23}$, $R^{24}$, $R^{25}$, $R^{26}$ and $R^{27}$ each independently represents hydrogen, $C_{1-3}$alkyl or $C_{1-3}$alkoxy$C_{2-3}$alkyl) and $R^{22}$ represents hydrogen, $C_{1-3}$alkyl or $C_{1-3}$alkoxy$C_{2-3}$alkyl);

5) $R^{28}$ (wherein $R^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

6) $C_{1-5}$alkyl$R^{28}$ (wherein $R^{28}$ is as defined hereinbefore);

7) $C_{2-5}$alkenyl$R^{28}$ (wherein $R^{28}$ is as defined hereinbefore);

8) $C_{2-5}$alkynyl$R^{28}$ (wherein $R^{28}$ is as defined hereinbefore);

9) $R^{29}$ (wherein $R^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)$NR^{30}R^{31}$, —$NR^{32}$C(O)$R^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

10) $C_{1-5}$alkyl$R^{29}$ (wherein $R^{29}$ is as defined hereinbefore);

11) $C_{2-5}$alkenyl$R^{29}$ (wherein $R^{29}$ is as defined hereinbefore);

12) $C_{2-5}$alkynyl$R^{29}$ (wherein $R^{29}$ is as defined hereinbefore);

13) $C_{1-5}$alkyl$X^6R^{29}$ (wherein $X^6$ represents —O—, —S—, —SO—, —$SO_2$—, —$NR^{34}$C(O)—, —C(O)$NR^{35}$—, —$SO_2NR^{36}$—, —$NR^{37}SO_2$— or —$NR^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);

14) $C_{2-5}$alkenyl$X^7R^{29}$ (wherein $X^7$ represents —O—, —S—, —SO—, —$SO_2$—, —$NR^{39}$C(O)—, —C(O)$NR^{40}$—, —$SO_2NR^{41}$—, —$NR^{42}SO_2$— or —$NR^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);

15) $C_{2-5}$alkynyl$X^8R^{29}$ (wherein $X^8$ represents —O—, —S—, —SO—, —$SO_2$—, —$NR^{44}$C(O)—, —C(O)$NR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);

16) $C_{1-5}$alkyl$X^9C_{1-4}$alkyl$R^{29}$ (wherein $X^9$ represents —O—, —S—, —SO—, —$SO_2$—, —$NR^{49}$C(O)—, —C(O)$NR^{50}$—, —$SO_2NR^{51}$—, —$NR^{52}SO_2$— or —$NR^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore);

17) $C_{1-4}$alkyl$X^9C_{1-4}$alkyl$R^{28}$ (wherein $X^9$ and $R^{28}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^9C_{1-4}$alkyl$R^{28}$ (wherein $X^9$ and $R^{28}$ are as defined hereinbefore);

21) $C_{2-5}$alkynyl$X^9C_{1-4}$alkyl$R^{28}$ (wherein $X^9$ and $R^{28}$ are as defined hereinbefore); and 22) $C_{1-4}$alkyl$R^{54}(C_{1-4}$alkyl)$_q(X^9)_rR^{55}$ (wherein $X^9$ is as defined hereinbefore, q is 0 or 1, r is 0 or 1, and $R^{54}$ and $R^{55}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— which is linked to $X^1$ may bear one or more substituents selected from hydroxy, halogeno and amino);

$R^1$ represents hydrogen, oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-3}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, N—($C_{1-4}$alkylsulphonyl)amino, N—($C_{1-4}$alkylsulphonyl)-N—($C_{1-4}$alkyl)amino, N,N-di($C_{1-4}$ alkylsulphonyl)amino, a $C_{3-7}$alkylene chain joined to two ring C carbon atoms, $C_{1-4}$alkanoylamino$C_{1-4}$alkyl, carboxy or a group $R^{56}X^{10}$ (wherein $X^{10}$ represents a direct bond, —O—, —$CH_2$—, —OC(O)—, —C(O)—, —S—, —SO—, —$SO_2$—, —$NR^{57}C(O)$—, —$C(O)NR^{58}$—, —$SO_2NR^{59}$—, —$NR^{60}SO_2$— or —$NR^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl), and $R^{56}$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;

2) $C_{1-5}$alkyl$X^{11}C(O)R^{62}$ (wherein $X^{11}$ represents —O— or —$NR^{63}$— (in which $R^{63}$ represents hydrogen, $C_{1-3}$alkyl or $C_{1-3}$alkoxy$C_{2-3}$alkyl) and $R^{62}$ represents $C_{1-3}$alkyl, —$NR^{64}R^{65}$ or —$OR^{66}$ (wherein $R^{64}$, $R^{65}$ and $R^{66}$ which may be the same or different each represents hydrogen, $C_{1-5}$alkyl or $C_{1-3}$alkoxy$C_{2-3}$alkyl));

3) $C_{1-5}$alkyl$X^{12}R^{67}$ (wherein $X^{12}$ represents —O—, —S—, —SO—, —$SO_2$—, —OC(O)—, —$NR^{68}C(O)$—, —$C(O)NR^{69}$—, —$SO_2NR^{70}$—, —$NR^{71}SO_2$— or —$NR^{72}$— (wherein $R^{68}$, $R^{69}$, $R^{70}$, $R^{71}$ and $R^{72}$ each independently represents hydrogen, $C_{1-3}$alkyl or $C_{1-3}$alkoxy$C_{2-3}$alkyl) and $R^{67}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

4) $C_{1-5}$alkyl$X^{13}C_{1-5}$alkyl$X^{14}R^{73}$ (wherein $X^{13}$ and $X^{14}$ which may be the same or different are each —O—, —S—, —SO—, —$SO_2$—, —$NR^{74}C(O)$—, —$C(O)NR^{75}$—, —$SO_2NR^{76}$—, —$NR^{77}SO_2$— or —$NR^{78}$— (wherein $R^{74}$, $R^{75}$, $R^{76}$, $R^{77}$ and $R^{78}$ each independently represents hydrogen, $C_{1-3}$alkyl or $C_{1-3}$alkoxy$C_{2-3}$alkyl) and $R^{73}$ represents hydrogen, $C_{1-3}$alkyl or $C_{1-3}$alkoxy$C_{2-3}$alkyl);

5) $R^{79}$ (wherein $R^{79}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

6) $C_{1-5}$alkyl$R^{79}$ (wherein $R^{79}$ is as defined hereinbefore);

7) $C_{2-5}$alkenyl$R^{79}$ (wherein $R^{79}$ is as defined hereinbefore);

8) $C_{2-5}$alkynyl$R^{79}$ (wherein $R^{79}$ is as defined hereinbefore);

9) $R^{80}$ (wherein $R^{80}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from oxo, hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$C(O)NR^{81}R^{82}$, —$NR^{83}C(O)R^{84}$ (wherein $R^{81}$, $R^{82}$, $R^{83}$ and $R^{84}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));

10) $C_{1-5}$alkyl$R^{80}$ (wherein $R^{80}$ is as defined hereinbefore);

11) $C_{2-5}$alkenyl$R^{80}$ (wherein $R^{80}$ is as defined hereinbefore);

12) $C_{2-5}$alkynyl$R^{80}$ (wherein $R^{80}$ is as defined hereinbefore);

13) $C_{1-5}$alkyl$X^{15}R^{80}$ (wherein $X^{15}$ represents —O—, —S—, —SO—, —$SO_2$—, —$NR^{85}C(O)$—, —$C(O)NR^{86}$—, —$SO_2NR^{87}$—, —$NR^{88}SO_2$— or —$NR^{89}$— (wherein $R^{85}$, $R^{86}$, $R^{87}$, $R^{88}$ and $R^{89}$ each independently represents hydrogen, $C_{1-3}$alkyl or $C_{1-3}$alkoxy$C_{2-3}$alkyl) and $R^{80}$ is as defined hereinbefore);

14) $C_{2-5}$alkenyl$X^{16}R^{80}$ (wherein $X^{16}$ represents —O—, —S—, —SO—, —$SO_2$—, —$NR^{90}C(O)$—, —$C(O)NR^{91}$—, —$SO_2NR^{92}$—, —$NR^{93}SO_2$— or —$NR^{94}$— (wherein $R^{90}$, $R^{91}$, $R^{92}$, $R^{93}$ and $R^{94}$ each independently represents hydrogen, $C_{1-3}$alkyl or $C_{1-3}$alkoxy$C_{2-3}$alkyl) and $R^{80}$ is as defined hereinbefore);

15) $C_{2-5}$alkynyl$X^{17}R^{80}$ (wherein $X^{17}$ represents —O—, —S—, —SO—, —$SO_2$—, —$NR^{95}C(O)$—, —$C(O)NR^{96}$—, —$SO_2NR^{97}$—, —$NR^{98}SO_2$— or —$NR^{99}$— (wherein $R^{95}$, $R^{96}$, $R^{97}$, $R^{98}$ and $R^{99}$ each independently represents hydrogen, $C_{1-3}$alkyl or $C_{1-3}$alkoxy$C_{2-3}$alkyl) and $R^{80}$ is as defined hereinbefore);

16) $C_{1-4}$alkyl$X^{18}C_{1-4}$alkyl$R^{80}$ (wherein $X^{18}$ represents —O—, —S—, —SO—, —$SO_2$—, —$NR^{100}C(O)$—, —$C(O)NR^{101}$—, —$SO_2NR^{102}$—, —$NR^{103}SO_2$— or —$NR^{104}$— (wherein $R^{100}$, $R^{101}$, $R^{102}$, $R^{103}$ and $R^{104}$ each independently represents hydrogen, $C_{1-3}$alkyl or $C_{1-3}$alkoxy$C_{2-3}$alkyl) and $R^{80}$ is as defined hereinbefore);

17) $C_{1-4}$alkyl$X^{18}C_{1-4}$alkyl$R^{79}$ (wherein $X^{18}$ and $R^{79}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^{18}C_{1-4}$alkyl$R^{79}$ (wherein $X^{18}$ and $R^{79}$ are as defined hereinbefore);

21) $C_{2-5}$alkynyl$X^{18}C_{1-4}$alkyl$R^{79}$ (wherein $X^{18}$ and $R^{79}$ are as defined hereinbefore); and 22) $C_{1-4}$alkyl$R^{105}(C_{1-4}$alkyl$)_x(X^{18})_yR^{106}$ (wherein $X^{18}$ is as defined hereinbefore, x is 0 or 1, y is 0 or 1, and $R^{105}$ and $R^{106}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, 4alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl$)_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl) with the proviso that $R^{105}$ cannot be hydrogen); and additionally wherein any $C_{1-5}$alkyl, $C_{2-5}$alkenyl or $C_{2-5}$alkynyl group in $R^{56}X^{16}$— which is linked to $X^{10}$ may bear one or more substituents selected from hydroxy, halogeno and amino); with the proviso that one or more $R^1$ and/or one or more $R^2$ are selected from the following group:

$Q^1X^1$— wherein $X^1$ is as defined hereinbefore and $Q^1$ is $C_{1-4}$alkyl-$Q^{13n}$-C(O)—$C_{1-4}$alkyl-$Q^{14n}$ wherein $Q^{13n}$ is $C_{1-3}$alkyl, cyclopentyl, cyclohexyl and a 5-6-membered saturated or partially unsaturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1, 2 or 3 substituents selected from $C_{2-5}$alkenyl, $C_{2-5}$alkynyl, $C_{1-6}$fluoroalkyl, $C_{1-6}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$ alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl$)_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl), and $Q^{14n}$ is a 5-6-membered saturated or partially unsaturated heterocyclic group containing at least one nitrogen atom and optionally containing a further nitrogen atom wherein $Q^{14n}$ is linked to $C_{1-6}$alkanoyl through a nitrogen atom and wherein $Q^{14n}$ optionally bears 1, 2 or 3 substituents selected from $C_{2-5}$alkenyl, $C_{2-5}$alkynyl, $C_{1-6}$fluoroalkyl, $C_{1-6}$alkanoyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$ alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl$)_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl);

and additionally wherein the $C_{1-4}$alkyl group in $Q^1X^1$—which is linked to $X^1$ may bear one or more substituents selected from hydroxy, halogeno and amino);

or a salt thereof, or a prodrug thereof for example an ester or an amide, in the manufacture of a medicament for use in the production of an antiangiogenic and/or vascular permeability reducing effect in warm-blooded animals such as humans.

According to one aspect of the present invention ring C is a 9-10-membered aromatic bicyclic moiety which may optionally contain 1-3 heteroatoms selected independently from O, N and S.

According to one aspect of the present invention ring C is a 9-10-membered heteroaromatic bicyclic moiety which contains 1-3 heteroatoms selected independently from O, N and S.

According to one aspect of the present invention ring C is a 9-10-membered heteroaromatic bicyclic moiety which contains 1 or 2 nitrogen atoms.

According to one aspect of the present invention ring C is indolyl, quinolinyl, indazolyl or azaindolyl.

According to one aspect of the present invention ring C is indolyl, indazolyl or azaindolyl.

According to one aspect of the present invention ring C is indolyl or azaindolyl.

According to one aspect of the present invention ring C is azaindolyl.

According to one aspect of the present invention ring C is indolyl.

According to one aspect of the present invention ring C is indazolyl.

According to one aspect of the present invention Z is —O— or —S—.

According to one aspect of the present invention Z is —O—.

In one embodiment of the present invention $X^1$ represents a direct bond, —O—, —S—, —NR$^6$C(O)—, —NR$^9$SO$_2$— or —NR$^{16}$— (wherein R$^6$, R$^9$ and R$^{16}$ each independently represents hydrogen, $C_{1-2}$alkyl or $C_{1-2}$alkoxyethyl).

In one embodiment of the present invention $X^1$ represents a direct bond, —O—, —S—, —NR$^6$C(O)—, —NR$^9$SO$_2$— (wherein R$^6$ and R$^9$ each independently represents hydrogen or $C_{1-2}$alkyl) or NH.

In one embodiment of the present invention $X^1$ represents —O—, —S—, —NR$^6$C(O)— (wherein R$^6$ represents hydrogen or $C_{1-2}$alkyl) or NH.

In one embodiment of the present invention $X^1$ represents —O— or —NR$^6$C(O)— (wherein R$^6$ represents hydrogen or $C_{1-2}$alkyl).

In one embodiment of the present invention $X^1$ represents —O— or —NHC(O)—.

In one embodiment of the present invention $X^1$ represents —O—.

According to another aspect of the present invention $X^1$ represents —O— or a direct bond.

In one embodiment of the present invention $R^1$ is $Q^1X^1$ wherein $Q^1$ and $X^1$ are as defined hereinbefore, and/or $R^1$ represents oxo, hydroxy, $C_{1-2}$alkoxymethyl, amino, halogeno, $C_{1-2}$alkyl, $C_{1-2}$alkoxy, trifluoromethyl, cyano, nitro, $C_{2-3}$alkanoyl.

According to one aspect of the present invention $R^1$ represents methyl, ethyl, trifluoromethyl or halogeno.

According to another aspect of the present invention $R^1$ represents methyl, fluoro, chloro or bromo.

According to another aspect of the present invention $R^1$ represents methyl or fluoro.

In one embodiment of the present invention n is 3.
In one embodiment of the present invention n is 2.
In one embodiment of the present invention n is 1.
In one embodiment of the present invention n is 0.
In one embodiment of the present invention n is 0, 1 or 2.
In one embodiment of the present invention m is 1 or 2.
In one embodiment of the present invention m is 1.
In one embodiment of the present invention m is 2.

In one embodiment of the present invention $X^3$ represents —O—, —S—, —SO—, —SO$_2$—, —SO$_2$NR$^{19}$— or —NR$^{21}$— (wherein $R^{19}$ and $R^{21}$ each independently represents hydrogen, $C_{1-2}$alkyl or $C_{1-2}$alkoxyethyl).

In one embodiment of the present invention $X^3$ represents —O— or —NR$^{21}$— (wherein $R^{21}$ represents hydrogen or $C_{1-2}$alkyl).

In one embodiment of the present invention $X^3$ represents —O—.

In one embodiment of the present invention $X^4$ and $X^5$ which may be the same or different each represents —O—, —S— or —NR$^{27}$— (wherein $R^{27}$ represents hydrogen, $C_{1-2}$alkyl or $C_{1-2}$alkoxyethyl).

In one embodiment of the present invention $X^4$ and $X^5$ which may be the same or different each represents —O— or —NH—.

In one embodiment of the present invention $X^4$ and $X^5$ each represents —O—.

In one embodiment of the present invention $X^6$ represents —O—, —S— or —NR$^{38}$— (wherein $R^{38}$ represents hydrogen, $C_{1-2}$alkyl or $C_{1-2}$alkoxyethyl).

In one embodiment of the present invention $X^6$ represents —O— or —NR$^{38}$— (wherein $R^{38}$ represents hydrogen or $C_{1-2}$alkyl).

In one embodiment of the present invention $X^6$ represents —O—.

In one embodiment of the present invention $X^2$ represents —O—, —S— or —NR$^{43}$— (wherein $R^{43}$ represents hydrogen, $C_{1-2}$alkyl or $C_{1-2}$alkoxyethyl).

In one embodiment of the present invention $X^2$ represents —O— or —NR$^{43}$— (wherein $R^{43}$ represents hydrogen or $C_{1-2}$alkyl).

In one embodiment of the present invention $X^2$ represents —O—.

In one embodiment of the present invention $X^8$ represents —O—, —S— or —NR$^{48}$— (wherein $R^{48}$ represents hydrogen, $C_{1-2}$alkyl or $C_{1-2}$alkoxyethyl).

In one embodiment of the present invention $X^8$ represents —O— or —NR$^{48}$— (wherein $R^{48}$ represents hydrogen or $C_{1-2}$alkyl).

In one embodiment of the present invention $X^8$ represents —O—.

In one embodiment of the present invention $X^9$ represents —O—, —S— or —NR$^{53}$— (wherein $R^{53}$ represents hydrogen, $C_{1-2}$alkyl or $C_{1-2}$alkoxyethyl).

In one embodiment of the present invention $X^9$ represents —O— or —NR$^{53}$— (wherein $R^{53}$ represents hydrogen or $C_{1-2}$alkyl).

In one embodiment of the present invention $X^9$ represents —O—.

In one embodiment of the present invention $R^{28}$ is pyrrolidinyl, piperazinyl, piperidinyl, imidazolidinyl, 1,3-dioxolan-2-yl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxyC$_{1-3}$alkyl, $C_{1-2}$alkylsulphonylC$_{1-3}$alkyl, $C_{1-3}$alkoxycarbonyl, $C_{1-3}$alkylamino, di($C_{1-3}$alkyl)amino, $C_{1-3}$alkylamino $C_{1-3}$alkyl, di($C_{1-3}$alkyl)aminoC$_{1-3}$alkyl, $C_{1-3}$alkylaminoC$_{1-3}$alkoxy, di($C_{1-3}$alkyl)aminoC$_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, morpholino and thiomorpholino, which cyclic group may bear one or more substituents selected from $C_{1-3}$alkyl).

In one embodiment of the present invention $R^{28}$ is pyrrolidinyl, piperazinyl, piperidinyl, 1,3-dioxolan-2-yl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxyC$_{1-3}$alkyl and $C_{1-2}$alkylsulphonylC$_{1-3}$alkyl.

In one embodiment of the present invention $R^{29}$ is phenyl, pyridyl, imidazolyl, thiazolyl or triazolyl group which group may bear 1 or 2 substituents selected from oxo, hydroxy, halogeno, $C_{1-4}$alkyl, $C_{1-4}$alkoxy, cyano and —NR$^{32}$C(O)R$^{33}$ (wherein $R^{32}$ and $R^{33}$ are each independently selected from hydrogen and $C_{1-4}$alkyl).

In one embodiment of the present invention $R^{54}$ and $R^{55}$ are each selected from pyrrolidinyl, piperazinyl, piperidinyl, imidazolidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxyC$_{1-3}$alkyl, $C_{1-2}$alkylsulphonylC$_{1-3}$ alkyl, $C_{1-3}$alkoxycarbonyl and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, morpholino and thiomorpholino, which cyclic group may bear one or more substituents selected from $C_{1-3}$alkyl).

In one embodiment of the present invention $R^2$ is $Q^1X^1$ wherein $Q^1$ and $X^1$ are as defined hereinbefore; and/or $R^2$ represents 6,7-methylenedioxy, 6,7-ethylenedioxy, hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 2-(ethylamino) ethyl, 2-(N,N-dimethylamino)ethyl, 2-(N,N-diethylamino) ethyl, 2-(N-methyl-N-methylsulphonylamino)ethyl, 3-(N- methyl-N-methylsulphonylamino)propyl, 2-morpholinoethyl, 3-morpholinopropyl, 2-piperidinoethyl, 2-(methylpiperidino)ethyl, 2-(ethylpiperidino)ethyl, 2-((2-methoxyethyl)piperidino)ethyl, 2-((2-methylsulphonyl)ethylpiperidino)ethyl, 3-((2-methylsulphonyl)ethylpiperidino)propyl, (1-cyanomethylpiperidin-3-yl)methyl, (1-cyanomethylpiperidin-4-yl)methyl, 2-(1-cyanomethylpiperidin-3-yl)ethyl, 2-(1-cyanomethylpiperidin-4-yl)ethyl, 3-(1-cyanomethylpiperidin-3-yl)propyl, 3-(1-cyanomethylpiperidin-4-yl)propyl, ((2-methoxyethyl)piperidin-3-yl)methyl, ((2-methoxyethyl)piperidin-4-yl)methyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, (pyrrolidin-2-yl)methyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-morpholinoethyl)piperidin-4-ylmethyl, 1-(2-thiomorpholinoethyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-(1-methylpiperazin-4-yl)-2-hydroxypropyl, (2R)-3-(1-methylpiperazin-4-yl)-2-hydroxypropyl or (2S)-3-(1-methylpiperazin-4-yl)-2-hydroxypropyl].

In one embodiment of the present invention $R^2$ is $Q^1X^1$ wherein $Q^1$ and $X^1$ are as defined hereinbefore, and/or $R^2$ represents 6,7-methylenedioxy, 6,7-ethylenedioxy, hydroxy, $C_{1-3}$alkyl, amino or $R^5X^1$— [wherein $X^1$ is —O— and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 2-(ethylamino)ethyl, 2-(N,N-dimethylamino)ethyl, 2-(N,N-diethylamino)ethyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 2-(methylpiperidino)ethyl, 2-(ethylpiperidino)ethyl, 2-((2-methoxyethyl)piperidino)ethyl, 2-((2-methylsulphonyl)ethylpiperidino)ethyl, 3-((2-methylsulphonyl)ethylpiperidino)propyl, (1-cyanomethylpiperidin-3-yl)methyl, (1-cyanomethylpiperidin-4-yl)methyl, 2-(1-cyanomethylpiperidin-3-yl)ethyl, 2-(1-cyanomethylpiperidin-4-yl)ethyl, 3-(1-cyanomethylpiperidin-3-yl)propyl, 3-(1-cyanomethylpiperidin-4-yl)propyl, ((2-methoxyethyl)piperidin-3-yl)methyl, ((2-methoxyethyl)piperidin-4-yl)methyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, (pyrrolidin-2-yl)methyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-morpholinoethyl)piperidin-4-ylmethyl, 1-(2-thiomorpholinoethyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2- hydroxypropyl, 3-(1-methylpiperazin-4-yl)-2-hydroxypropyl, (2R)-3-(1-methylpiperazin-4-yl)-2-hydroxypropyl or (2S)-3-(1-methylpiperazin-4-yl)-2-hydroxypropyl].

In one embodiment of the present invention $R^2$ substituents are at the 6- and/or 7-positions of the quinazoline ring.

In one embodiment of the present invention $R^2$ is $Q^1X^1$ wherein $Q^1$ and $X^1$ are as defined hereinbefore and/or $R^2$ represents methoxy.

According to another aspect of the present invention there are provided compounds of the formula I.

According to another aspect of the present invention there are provided compounds of the formula Ia:

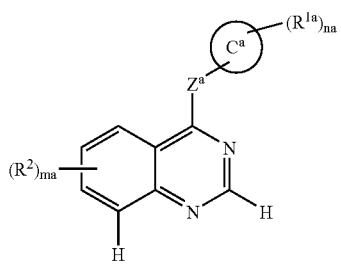

wherein:
ring $C^a$ is indolyl, indazolyl or azaindolyl;
$R^{1a}$ is selected from oxo, hydroxy, $C_{1-2}$alkoxymethyl, amino, halogeno, $C_{1-3}$alkyl, $C_{1-3}$alkoxy, trifluoromethyl, cyano, nitro, $C_{1-3}$alkanoyl and $Q^1X^1$ wherein $Q^1$ and $X^1$ are as defined hereinbefore;
$R^2$ is as defined hereinbefore;
ma is 0, 1, 2 or 3;
Za is —O— or —S—;
and na is 0, 1 or 2;
with the proviso that at least one $R^2$ is selected from $Q^1X^1$ as defined hereinbefore in the definitions of $R^2$, and/or $R^{1a}$ is selected from $Q^1X^1$ as defined hereinbefore;
and salts thereof, and prodrugs thereof for example esters, amides and sulphides, preferably esters and amides.

According to another aspect of the present invention there are provided compounds of the formula II:

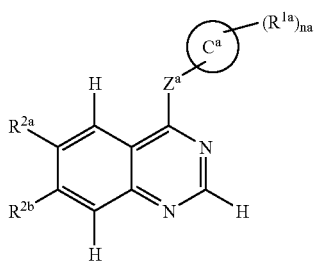

wherein:
ring $C^a$ is indolyl, indazolyl or azaindolyl;
$R^{1a}$ is selected from oxo, hydroxy, $C_{1-2}$alkoxymethyl, amino, halogeno, $C_{1-3}$alkyl, $C_{1-3}$alkoxy, trifluoromethyl, cyano, nitro, $C_{1-3}$alkanoyl and $Q^1X^1$ wherein $Q^1$ and $X^1$ are as defined hereinbefore;
$R^{2a}$ and $R^{2b}$, are each independently selected from hydrogen, hydroxy, halogeno, cyano, nitro, trifluoromethyl, $C_{1-3}$alkyl, $C_{1-3}$alkoxy, $C_{1-3}$alkylsulphanyl, —NR$^{3a}$R$^{4a}$ (wherein $R^{3a}$ and $R^{4a}$, which may be the same or different, each represents hydrogen or $C_{1-3}$alkyl), and $Q^1X^1$ wherein $Q^1$ and $X^1$ are as defined hereinbefore;
Za is —O— or —S—;
and na is 0, 1 or 2;
with the proviso that at least one of $R^{2a}$ and $R^{2b}$ is $Q^1X^1$ wherein $Q^1$ and $X^1$ are as defined hereinbefore;
and salts thereof, and prodrugs thereof for example esters, amides and sulphides, preferably esters and amides.

According to another aspect of the present invention there are provided compounds of the formula IIa as defined hereinbefore wherein at least one of $R^{2a}$ and $R^{2b}$ is $Q^1X^1$ wherein $Q^1$ and $X^1$ are as defined hereinbefore.

In one embodiment of the present invention $Z^a$ is —O—.
In one embodiment of the present invention $C^a$ is indol-5-yl, indol-6-yl, 7-azaindol-5-yl, indazol-5-yl, indazol-6-yl.
In one embodiment of the present invention $C^a$ is indol-5-yl, 7-azaindol-5-yl or indazol-5-yl.
In one embodiment of the present invention $C^a$ is indol-5-yl or indol-6-yl.
In one embodiment of the present invention $C^a$ is indol-5-yl.
In one embodiment of the present invention $C^a$ is 7-azaindol-5-yl.
In one embodiment of the present invention $R^{1a}$ is halogeno or $C_{1-3}$ alkyl.
In one embodiment of the present invention $R^{1a}$ is fluoro or methyl.
In one embodiment of the present invention $R^{2a}$ is methoxy and $R^{2b}$ is $Q^1X^1$ wherein $Q^1$ and $X^1$ are as defined hereinbefore.
In another embodiment of the present invention $R^{2b}$ is methoxy and $R^{2a}$ is $Q^1X^1$ wherein $Q^1$ and $X^1$ are as defined hereinbefore.

According to another aspect of the present invention there are provided compounds of the formula IIb:

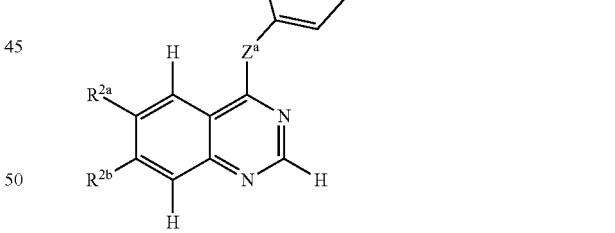

wherein:
M is —CH— or —N—;
nc is 0, 1 or 2;
$R^{2c}$ is linked to a carbon atom of the 5-membered ring and is selected from hydrogen and methyl;
$R^{2d}$ is linked to a carbon atom of the 6-membered ring and is selected from hydrogen and fluoro;
$Z^a$, $R^{2a}$ and $R^{2b}$, are as defined hereinbefore;
with the proviso that at least one of $R^{2a}$ and $R^{2b}$ is $Q^1X^1$ wherein $Q^1$ and $X^1$ are as defined hereinbefore;
and salts thereof, and prodrugs thereof for example esters, amides and sulphides, preferably esters and amides.

According to another aspect of the present invention there are provided compounds of the formula IId:

(IId)

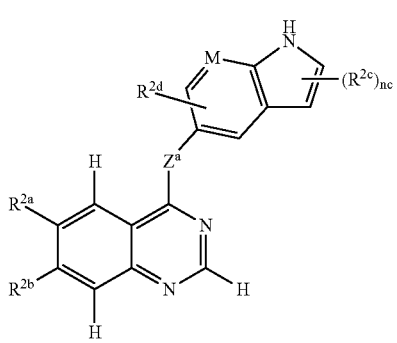

[wherein:
M is —CH— or —N—;
nc is 0, 1 or 2;
Za is —O— or —S—;
$R^{2c}$ is linked to a carbon atom of the 5-membered ring and is selected from hydrogen and methyl;
$R^{2d}$ is linked to a carbon atom of the 6-membered ring and is selected from hydrogen and fluoro;
one of $R^{2a}$ and $R^{2b}$ is methoxy and the other is $Q^1X^1$ wherein $X^1$ is as defined hereinbefore and $Q^1$ is selected from one of the following groups:
1) $C_{1-4}$alkyl-$Q^{13}$-C(O)—$C_{1-4}$alkyl-$Q^{14}$ wherein $Q^{13}$ is as defined hereinbefore and $Q^{14}$ is selected from pyrrolidinyl, piperidinyl, piperazinyl,

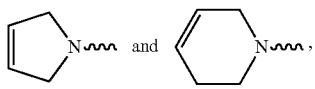

wherein $Q^{14}$ is linked to $C_{1-6}$alkanoyl through a nitrogen atom;
2) $Q^2$ (wherein $Q^2$ is a 5-6-membered heterocyclic group selected from pyrrolidinyl, piperidinyl, piperazinyl,

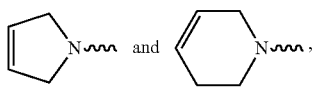

which heterocyclic group bears either one substituent selected from methylenedioxy or ethylenedioxy to form a bicyclic ring, or bears at least one substituent selected from $C_{1-6}$alkanoyl$C_{1-6}$alkyl and optionally bears a further 1 or 2 substituents selected from $C_{2-5}$alkenyl, $C_{2-5}$alkynyl, $C_{1-6}$fluoroalkyl, $C_{1-6}$alkanoyl, $C_{1-6}$alkanoyl$C_{1-6}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which cyclic group may bear one or more substituents selected from $C_{1-4}$alkyl));
3) $C_{1-5}$alkyl$W^1Q^2$ (wherein $W^1$ and $Q^2$ are as defined hereinbefore;
4) $C_{1-5}$alkyl$Q^2$ (wherein $Q^2$ is as defined hereinbefore);
5) $C_{2-5}$alkenyl$Q^2$ (wherein $Q^2$ is as defined hereinbefore);
6) $C_{2-5}$alkynyl$Q^2$ (wherein $Q^2$ is as defined hereinbefore);
7) $C_{1-4}$alkyl$W^2C_{1-4}$alkyl $Q^2$ (wherein $W^2$ and $Q^2$ are as defined hereinbefore);
8) $C_{2-5}$alkenyl$W^2C_{1-4}$alkyl$Q^2$ (wherein $W^2$ and $Q^2$ are as defined hereinbefore);
9) $C_{2-5}$alkynyl$W^2C_{1-4}$alkyl$Q^2$ (wherein $W^2$ and $Q^2$ are as defined hereinbefore);
10) $C_{1-4}$alkyl$Q^{15}(C_{1-4}$alkyl)$_j(W^2)_kQ^{16}$ (wherein $W^2$ is as defined hereinbefore, j is 0 or 1, k is 0 or 1, and $Q^{15}$ and $Q^{16}$ are each independently selected from a 5-6-membered heterocyclic group selected from pyrrolidinyl, piperidinyl, piperazinyl,

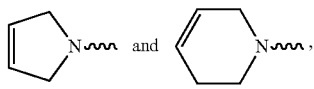

which heterocyclic group may bear either one substituent selected from methylenedioxy or ethylenedioxy to form a bicyclic ring, or may bear 1, 2 or 3 substituents selected from $C_{2-5}$alkenyl, $C_{2-5}$alkynyl, $C_{1-6}$fluoroalkyl, $C_{1-6}$alkanoyl, $C_{1-6}$alkanoyl$C_{1-6}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$ alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl), with the proviso one or both of $Q^{15}$ and $Q^{16}$ must be a 5-6-membered heterocyclic group as defined hereinbefore which heterocyclic group bears either one substituent selected from methylenedioxy or ethylenedioxy to form a bicyclic ring, or bears at least one substituent selected from $C_{1-6}$alkanoyl$C_{1-6}$alkyl and optionally bears 1 or 2 further substituents selected from those defined hereinbefore);
11) $C_{1-4}$alkyl$Q^{15}C_{1-4}$alkanoyl$Q^{16n}$ wherein $Q^{15}$ is as defined hereinbefore and $Q^{16n}$ is a 5-6-membered heterocyclic group selected from pyrrolidinyl, piperidinyl, piperazinyl,

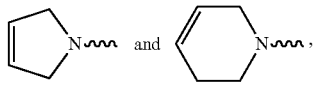

wherein $Q^{16n}$ is linked to $C_{1-6}$alkanoyl through a nitrogen atom and wherein $Q^{16n}$ bears either one substituent selected from methylenedioxy or ethylenedioxy to form a bicyclic ring, or bears 1, 2 or 3 substituents selected from $C_{2-5}$alkenyl, $C_{2-5}$alkynyl, $C_{1-6}$fluoroalkyl, $C_{1-6}$alkanoyl, $C_{1-6}$alkanoyl$C_{1-6}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl); with the proviso that one or both of $Q^{15}$ and $QQ^{16n}$ must be a 5-6-membered heterocyclic group as defined hereinbefore which heterocyclic group bears either one substituent selected from methylenedioxy or ethylenedioxy to form a bicyclic ring, or bears at least one substituent selected from $C_{1-6}$alkanoyl$C_{1-6}$alkyl and optionally bears 1 or 2 further substituents selected from those defined hereinbefore;

and additionally wherein any $C_{1-5}$alkyl, $C_{2-5}$alkenyl or $C_{2-5}$alkynyl group in $Q^1X^1$— which is linked to $X^1$ may bear one or more substituents selected from hydroxy, halogeno and amino); and salts thereof, and prodrugs thereof for example esters, amides and sulphides, preferably esters and amides.

In one embodiment of the present invention one of $R^{2a}$ and $R^{2b}$ is methoxy and the other is $Q^1X^1$ wherein $X^1$ is —O— and $Q^1$ is selected from one of the following groups:
1) $C_{1-4}$alkyl-$Q^{13}$-C(O)—$C_{1-4}$alkyl-$Q^{14}$ wherein $Q^{13}$ and $Q^{14}$ are each independently selected from pyrrolidinyl, piperidinyl, piperazinyl,

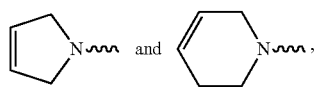

wherein $Q^{14}$ is linked to $C_{1-6}$alkanoyl through a nitrogen atom;
2) $Q^2$ (wherein $Q^2$ is a 5-6-membered heterocyclic group selected from pyrrolidinyl, piperidinyl, piperazinyl,

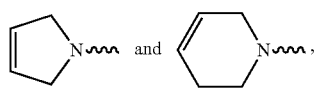

which heterocyclic group bears either one substituent selected from methylenedioxy or ethylenedioxy to form a bicyclic ring, or bears at least one substituent selected from $C_{2-4}$alkanoyl$C_{1-3}$alkyl and optionally bears a further 1 or 2 substituents selected from $C_{2-5}$alkenyl, $C_{2-5}$alkynyl, $C_{1-6}$fluoroalkyl, $C_{1-6}$alkanoyl, $C_{2-4}$alkanoyl$C_{1-3}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which cyclic group may bear one or more substituents selected from $C_{1-4}$alkyl));
3) $C_{1-5}$alkyl$Q^2$ (wherein $Q^2$ is as defined hereinbefore);
4) $C_{1-4}$alkyl$W^2C_{1-4}$alkyl$Q^2$ (wherein $W^2$ and $Q^2$ are as defined hereinbefore);
5) $C_{1-4}$alkyl$Q^{15}$($C_{1-4}$alkyl)$_j$($W^2$)$_k$$Q^{16}$ (wherein $W^2$ is as defined hereinbefore, j is 0 or 1, k is 0 or 1, and $Q^{15}$ and $Q^{16}$ are each independently selected from a 5-6-membered heterocyclic group selected from pyrrolidinyl, piperidinyl, piperazinyl,

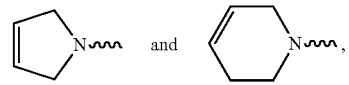

which heterocyclic group may bear either one substituent selected from methylenedioxy or ethylenedioxy to form a bicyclic ring, or may bear 1, 2 or 3 substituents selected from $C_{2-5}$alkenyl, $C_{2-5}$alkynyl, $C_{1-6}$fluoroalkyl, $C_{1-6}$alkanoyl, $C_{2-4}$alkanoyl$C_{1-3}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from $C_{1-4}$alkyl), with the proviso one or both of $Q^{15}$ and $Q^{16}$ must be a 5-6-membered heterocyclic group as defined hereinbefore which heterocyclic group bears either one substituent selected from methylenedioxy or ethylenedioxy to form a bicyclic ring, or bears at least one substituent selected from $C_{2-4}$alkanoyl$C_{1-3}$alkyl and optionally bears 1 or 2 further substituents selected from those defined hereinbefore);
6) $C_{1-4}$alkyl$Q^{15}C_{1-4}$alkanoyl$Q^{16n}$ wherein $Q^{15}$ is as defined hereinbefore and $Q^{16n}$ is a 5-6-membered heterocyclic group selected from pyrrolidinyl, piperidinyl, piperazinyl,

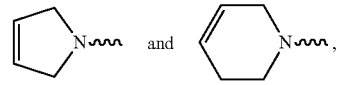

wherein $Q^{16n}$ is linked to $C_{1-6}$alkanoyl through a nitrogen atom and wherein $Q^{16n}$ bears either one substituent selected from methylenedioxy or ethylenedioxy to form a bicyclic ring, or bears 1, 2 or 3 substituents selected from $C_{2-5}$alkenyl, $C_{2-5}$alkynyl, $C_{1-6}$fluoroalkyl, $C_{1-6}$alkanoyl, $C_{2-4}$alkanoyl$C_{1-3}$ alkyl, aminoC$_{1-6}$alkanoyl, C$_{1-4}$alkylaminoC$_{1-6}$alkanoyl, di(C$_{1-4}$alkyl)aminoC$_{1-6}$alkanoyl, C$_{1-6}$fluoroalkanoyl, carbamoyl, C$_{1-4}$alkylcarbamoyl, di(C$_{1-4}$alkyl)carbamoyl, carbamoylC$_{1-6}$alkyl, C$_{1-4}$alkylcarbamoylC$_{1-6}$alkyl, di(C$_{1-4}$alkyl)carbamoylC$_{1-6}$alkyl, C$_{1-6}$alkylsulphonyl, C$_{1-6}$fluoroalkylsulphonyl, oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$ alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 5-6-membered saturated or partially unsaturated heterocyclic group with 1-2 heteroatoms, selected independently from O, S and N, which heterocyclic group may bear one or more substituents selected from C$_{1-4}$alkyl); with the proviso that one or both of Q$^{15}$ and Q$^{16n}$ must be a 5-6-membered heterocyclic group as defined hereinbefore which heterocyclic group bears either one substituent selected from methylenedioxy or ethylenedioxy to form a bicyclic ring, or bears at least one substituent selected from C$_{2-4}$alkanoylC$_{1-3}$alkyl and optionally bears 1 or 2 further substituents selected from those defined hereinbefore;

and additionally wherein any C$_{1-5}$alkyl, C$_{2-5}$alkenyl or C$_{2-5}$alkynyl group in Q$^1$X$^1$— which is linked to X$^1$ may bear one or more substituents selected from hydroxy, halogeno and amino).

In one embodiment of the present invention one of R$^{2a}$ and R$^{2b}$ is methoxy and the other is Q$^1$X$^1$ wherein X$^1$ is —O— and Q$^1$ is
C$_{1-4}$alkyl-Q$^{13}$-C(O)—C$_{1-4}$alkyl-Q$^{14}$ wherein Q$^{13}$ and Q$^{14}$ are each independently selected from pyrrolidinyl, piperidinyl, piperazinyl,

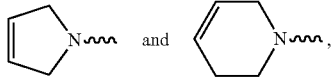

wherein Q$^{14}$ is linked to C$_{1-6}$alkanoyl through a nitrogen atom.

In one embodiment of the present invention one of R$^{2a}$ and R$^{2b}$ is methoxy and the other is Q$^1$X$^1$ wherein X$^1$ is —O— and Q$^1$ is selected from one of the following groups:
1) Q$^2$ (wherein Q$^2$ is a 5-6-membered heterocyclic group selected from pyrrolidinyl, piperidinyl, piperazinyl,

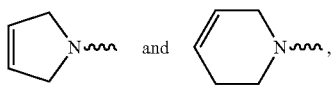

which heterocyclic group bears either one substituent selected from methylenedioxy or ethylenedioxy to form a bicyclic ring, or bears one substituent selected from C$_{2-4}$alkanoylC$_{1-3}$alkyl; and
2) C$_{1-5}$alkylQ$^2$ (wherein Q$^2$ is as defined hereinbefore).

In one embodiment of the present invention R$^{2a}$ is methoxy.

In one embodiment of the present invention one of R$^{2a}$ and R$^{2b}$ is methoxy and the other is Q$^1$X$^1$ wherein X$^1$ is —O— and Q$^1$ is
C$_{1-4}$alkyl-Q$^{13n}$-C(O)—C$_{1-4}$alkyl-Q$^{14n}$
Q$^{13}$a and Q$^{14}$a are each independently selected from pyrrolidinyl, piperidinyl, piperazinyl,

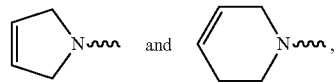

which heterocyclic group may bear 1, 2 or 3 substituents selected from C$_{2-5}$alkenyl, C$_{2-5}$alkynyl, C$_{1-4}$fluoroalkyl, C$_{1-4}$alkanoyl, aminoC$_{1-6}$alkanoyl, C$_{1-4}$alkylaminoC$_{1-6}$alkanoyl, di(C$_{1-4}$alkyl)aminoC$_{1-6}$alkanoyl, C$_{1-6}$fluoroalkanoyl, carbamoyl, C$_{1-4}$alkylcarbamoyl, di(C$_{1-4}$alkyl)carbamoyl, carbamoylC$_{1-6}$alkyl, C$_{1-4}$alkylcarbamoylC$_{1-6}$alkyl, di(C$_{1-4}$alkyl)carbamoylC$_{1-6}$alkyl, C$_{1-4}$alkylsulphonyl, C$_{1-4}$fluoroalkylsulphonyl, oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl;
with the proviso that at least one of Q$^{13}$a and Q$^{14n}$ bears at least one substituent selected from C$_{2-5}$alkenyl, C$_{2-5}$alkynyl, C$_{1-4}$fluoroalkyl, C$_{1-4}$alkanoyl, aminoC$_{1-6}$alkanoyl, C$_{1-4}$alkylaminoC$_{1-6}$alkanoyl, di(C$_{1-4}$alkyl)aminoC$_{1-6}$alkanoyl, C$_{1-6}$fluoroalkanoyl, carbamoyl, C$_{1-4}$alkylcarbamoyl, di(C$_{1-4}$alkyl)carbamoyl, carbamoylC$_{1-6}$alkyl, C$_{1-4}$alkylcarbamoylC$_{1-6}$alkyl, di(C$_{1-4}$alkyl)carbamoylC$_{1-6}$alkyl, C$_{1-4}$alkylsulphonyl and C$_{1-4}$fluoroalkylsulphonyl);
and additionally wherein any C$_{1-4}$alkyl group in Q$^1$X$^1$— which is linked to X$^1$ may bear one or more substituents selected from hydroxy, halogeno and amino).

In one embodiment of the present invention one of R$^{2a}$ and R$^{2b}$ is methoxy and the other is Q$^1$X$^1$ wherein X$^1$ is —O— and Q$^1$ is
C$_{1-4}$alkyl-Q$^{13n}$C(O)—C$_{1-4}$alkyl-Q$^{14n}$
Q$^{13n}$ and Q$^{14n}$ are each independently selected from pyrrolidinyl, piperidinyl, piperazinyl,

which heterocyclic group may bear 1, 2 or 3 substituents selected from C$_{2-5}$alkenyl, C$_{2-5}$alkynyl, C$_{1-4}$alkanoyl, aminoC$_{1-6}$alkanoyl, C$_{1-4}$alkylaminoC$_{1-6}$alkanoyl, di(C$_{1-4}$alkyl)aminoC$_{1-6}$alkanoyl, C$_{1-6}$fluoroalkanoyl, carbamoyl, C$_{1-4}$alkylcarbamoyl, di(C$_{1-4}$alkyl)carbamoyl, carbamoylC$_{1-6}$alkyl, C$_{1-4}$alkylcarbamoylC$_{1-6}$alkyl, di(C$_{1-4}$alkyl)carbamoylC$_{1-6}$alkyl, C$_{1-4}$alkylsulphonyl, C$_{1-4}$fluoroalkylsulphonyl, oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl;
with the proviso that at least one of Q$^{13n}$ and Q$^{14n}$ bears at least one substituent selected from C$_{2-5}$alkenyl, C$_{2-5}$alkynyl, C$_{1-4}$alkanoyl, aminoC$_{1-6}$alkanoyl, C$_{1-4}$alkylaminoC$_{1-6}$alkanoyl, di(C$_{1-4}$alkyl)aminoC$_{1-6}$alkanoyl, C$_{1-6}$fluoroalkanoyl, carbamoyl, C$_{1-4}$alkylcarbamoyl, di(C$_{1-4}$alkyl)carbamoyl, carbamoylC$_{1-6}$alkyl, C$_{1-4}$alkylcarbamoylC$_{1-6}$alkyl, di(C$_{1-4}$alkyl)carbamoylC$_{1-6}$alkyl, C$_{1-4}$alkylsulphonyl and C$_{1-4}$fluoroalkylsulphonyl); and additionally wherein any C$_{1-4}$alkyl group in Q$^1$X$^1$— which is linked to X$^1$ may bear one or more substituents selected from hydroxy, halogeno and amino).

Examples of compounds of the present invention include
7-({1-[(4-acetylpiperazin-1-yl)acetyl]piperidin-4-yl}methoxy)-4-[(4-fluoro-2-methyl-1H-indol)-5-yloxy]-6-methoxyquinazoline,
4-[(4-fluoro-2-methyl-1H-indol)-5-yloxy]-6-methoxy-7-{[1-(pyrrolidin-1-ylacetyl)piperidin-4-yl]methoxy}quinazoline, 4-[(4-fluoro-2-methyl-1H-indol)-5-yloxy]-6-methoxy-7-{[1-(piperidin-1-ylacetyl)piperidin-4-yl]methoxy}quinazoline,
4-[(4-fluoro-2-methyl-1H-indol)-5-yloxy]-6-methoxy-7-{[1-(morpholin-4-ylacetyl)piperidin-4-yl]methoxy}quinazoline,
4-[(4-fluoro-2-methyl-1H-indol)-5-yloxy]-6-methoxy-7-({1-[(3aR,6aS)-tetrahydro-5H-[1,3]dioxolo[4,5-c]pyrrol-5-ylacetyl]piperidin-4-yl}methoxy)quinazoline,
(3S)-4-[4-fluoro-2-methyl-1H-indol)-5-yloxy]-7-({1-[(3-hydroxypyrrolidin-1-yl)acetyl]piperidin-4-yl}methoxy)-6-methoxyquinazoline,
7-({1-[(3,3-difluoropyrrolidin-1-yl)acetyl]piperidin-4-yl}methoxy)-4-[4-fluoro-2-methyl-1H-indol)-5-yloxy]-6-methoxy-quinazoline,
and salts thereof.

Examples of compounds of the present invention include:
7-{[1-(acetylmethyl)piperidin-4-yl]methoxy}-6-methoxy-4-[(3-methyl-1H-indol-5-yl)oxy]quinazoline,
7-{[1-(acetylmethyl)piperidin-4-yl]methoxy}-6-methoxy-4-[(2-methyl-1H-indol-6-yl)oxy]quinazoline,
7-{[1-(acetylmethyl)piperidin-4-yl]methoxy}-6-methoxy-4-[(2-methyl-1H-indol-5-yl)oxy]quinazoline,
6-methoxy-4-[(3-methyl-1H-indol-5-yl)oxy]-7-{[1-(pyrrolidin-1-ylacetyl)piperidin-4-yl]methoxy}quinazoline,
6-methoxy-4-[(2-methyl-1H-indol-6-yl)oxy]-7-{[1-(pyrrolidin-1-ylacetyl)piperidin-4-yl]methoxy}quinazoline,
6-methoxy-4-[(2-methyl-1H-indol-5-yl)oxy]-7-{[1-(pyrrolidin-1-ylacetyl)piperidin-4-yl]methoxy}quinazoline,
6-methoxy-4-[(2-methyl-1H-indol-5-yl)oxy]-7-[2-(tetrahydro-5H-[1,3]dioxolo[4,5-c]pyrrol-5-yl)ethoxy]quinazoline,
6-methoxy-4-[(3-methyl-1H-indol-5-yl)oxy]-7-[2-(tetrahydro-5H-[1,3]dioxolo[4,5-c]pyrrol-5-yl)ethoxy]quinazoline,
4-[(2,3-dimethyl-1H-indol-5-yl)oxy]-6-methoxy-7-[2-(tetrahydro-5H-[1,3]dioxolo[4,5-c]pyrrol-5-yl)ethoxy]quinazoline,
4-[(4-fluoro-2-methyl-1H-indol-5-yl)oxy]-6-methoxy-7-[2-(tetrahydro-5H-[1,3]dioxolo[4,5-c]pyrrol-5-yl)ethoxy]quinazoline,
7-{2-[4-(acetylmethyl)piperazin-1-yl]ethoxy}-4-[(2,3-dimethyl-1H-indol-5-yl)oxy]-6-methoxyquinazoline,
7-{2-[4-(acetylmethyl)piperazin-1-yl]ethoxy}-6-methoxy-4-[(3-methyl-1H-indol-5-yl)oxy]quinazoline,
7-{2-[4-(acetylmethyl)piperazin-1-yl]ethoxy}-6-methoxy-4-[(2-methyl-1H-indol-5-yl)oxy]quinazoline,
7-{2-[4-(acetylmethyl)piperazin-1-yl]ethoxy}-4-[(4-fluoro-2-methyl-1H-indol-5-yl)oxy]-6-methoxyquinazoline,
6-methoxy-4-[(2-methyl-1H-indol-5-yl)oxy]-7-{2-[4-(pyrrolidin-1-ylacetyl)piperazin-1-yl]ethoxy}quinazoline,
7-{[1-(acetylmethyl)piperidin-4-yl]oxy}-6-methoxy-4-[(2-methyl-1H-indol-6-yl)oxy]quinazoline,
7-{[1-(acetylmethyl)piperidin-4-yl]oxy}-6-methoxy-4-[(2-methyl-1H-indol-5-yl)oxy]quinazoline,
7-{[1-(acetylmethyl)piperidin-4-yl]oxy}-4-[(4-fluoro-2-methyl-1H-indol-5-yl)oxy]-6-methoxyquinazoline,
and salts thereof.

Particularly preferred compounds of the present invention include:
4-[(4-fluoro-2-methyl-1H-indol-5-yl)oxy]-6-methoxy-7-[2-(tetrahydro-5H-[1,3]dioxolo[4,5-c]pyrrol-5-yl)ethoxy]quinazoline,
7-{2-[4-(acetylmethyl)piperazin-1-yl]ethoxy}-6-methoxy-4-[(2-methyl-1H-indol-5-yl)oxy]quinazoline,
7-{2-[4-(acetylmethyl)piperazin-1-yl]ethoxy}-4-[(4-fluoro-2-methyl-1H-indol-5-yl)oxy]-6-methoxyquinazoline,
and salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1-6 carbon atoms, preferably 1-4 carbon atoms. The term "alkoxy" as used herein, unless stated otherwise includes "alkyl"-O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"-O-groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C=O$, $C_1$alkanoyl is formyl and refers to CHO. Butanoyl refers to $CH_3$—$CH_2$—$CH_2$—C(O), isobutyryl refers to $(CH_3)_2$.CH—C(O). In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2-5 carbon atoms, preferably 3-4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2-5 carbon atoms, preferably 3-4 carbon atoms. Unless stated otherwise the term "haloalkyl" refers to an alkyl group as defined hereinbefore which bears one or more halogeno groups, such as for example trifluoromethyl.

In this specification the term azaindolyl refers to the moiety (1H-pyrrolo[2,3-b]pyridinyl) and an analogous convention applies to similar groups. For example 7-azaindol-5-yl is (1H-pyrrolo[2,3-b]pyridin-5-yl) and is the group:

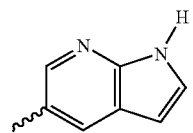

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated that compounds of the formula I or a salt thereof may possess an asymmetric carbon atom. Such an asymmetric carbon atom is also involved in the tautomerism described above, and it is to be understood that the present invention encompasses any chiral form (including both pure enantiomers, scalemic and racemic mixtures) as well as any tautomeric form which inhibits VEGF receptor tyrosine kinase activity, and is not to be limited merely to any one tautomeric form or chiral form utilised within the formulae drawings. It is to be understood that the invention encompasses all optical and diastereomers which inhibit VEGF receptor tyrosine kinase activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ration 50:50.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^6C(O)$—, it is the nitrogen atom bearing the $R^6$ group which is attached to the quinazoline ring and the carbonyl (C(O)) group is attached to $R^5$, whereas when $X^1$ is, for example, a group of formula —$C(O)NR^7$—, it is the carbonyl group which is attached to the quinazoline ring and the nitrogen atom bearing the $R^7$ group is attached to $R^5$. A similar convention applies to the other two atom $X^1$ linking groups such as —$NR^9SO_2$— and —$SO_2NR^8$—. When $X^1$ is —$NR^{16}$— it is the nitrogen atom bearing the $R^{10}$ group which is linked to the quinazoline ring and to $R^5$. An analogous convention applies to other groups. It is further to be understood that when $X^1$ represents —$NR^{10}$— and $R^{10}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^5$ is, for example, a group of formula $C_{1-3}$alkyl$X^9C_{1-3}$alkyl$R^{29}$, it is the terminal $C_{1-3}$alkyl moiety which is linked to $X^1$, similarly when $R^5$ is, for example, a group of formula $C_{2-5}$alkenyl$R^{28}$ it is the $C_{2-5}$alkenyl moiety which is linked to $X^1$ and an analogous convention applies to other groups. When $R^5$ is a group 1-$R^{29}$prop-1-en-3-yl it is the first carbon to which the group $R^{29}$ is attached and it is the third carbon which is linked to $X^1$ and an analogous convention applies to other groups.

For the avoidance of any doubt, it is to be understood that in a compound of the formula I when $R^5$ is, for example, $R^{28}$ and $R^{28}$ is a pyrrolidinyl ring which bears a group —(—O—)$_f$($C_{1-4}$alkyl)$_g$ringD, it is the —O— or $C_{1-4}$alkyl which is linked to the pyrrolidinyl ring, unless f and g are both 0 when it is ring D which is linked to the pyrrolidinyl ring and an analogous convention applies to other groups.

For the avoidance of any doubt, it is to be understood that when $R^{29}$ carries a $C_{1-4}$aminoalkyl substituent it is the $C_{1-4}$alkyl moiety which is attached to $R^{29}$ whereas when $R^{29}$ carries a $C_{1-4}$alkylamino substituent it is the amino moiety which is attached to $R^{29}$ and an analogous convention applies to other groups.

For the avoidance of any doubt, it is to be understood that when $R^{28}$ carries a $C_{1-4}$alkoxy$C_{1-4}$alkyl substituent it is the $C_{1-4}$alkyl moiety which is attached to $R^{28}$ and an analogous convention applies to other groups.

For the avoidance of any doubt, it is to be understood that when $R^2$ is —$X^1$—$C_{1-4}$alkyl-$Q^{13}$-C(O)—$C_{1-4}$alkyl-$Q^{14}$ it is $X^1$ that is linked to the quinazoline ring, $Q^{13}$ is linked to the $C_{1-4}$alkyl chain and to the carbonyl group, the carbonyl group is also linked to the terminal $C_{1-4}$alkyl chain and $Q^{14}$ is linked to the terminal $C_{1-4}$alkyl chain.

A particular value of $C_{1-6}$alkanoyl$C_{1-6}$alkyl is acetylmethyl.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine A compound of the formula I, or salt thereof, and other compounds of the invention (as herein defined) may be prepared by any process known to be applicable to the preparation of chemically-related compounds. Such processes include, for example, those illustrated in International Patent Application Number WO 00/47212 and in European Patent Applications Publication Nos. 0520722, 0566226, 0602851 and 0635498. Such processes also include, for example, solid phase synthesis. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus, the following processes (a) to (f) and (i) to (vi) constitute further features of the present invention.

Synthesis of Compounds of Formula I (a) Compounds of the formula I and salts thereof may be prepared by the reaction of a compound of the formula III:

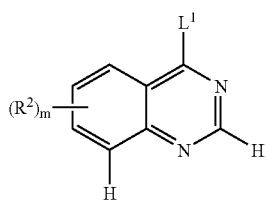

(III)

(wherein $R^2$ and m are as defined hereinbefore and $L^1$ is a displaceable moiety), with a compound of the formula IV:

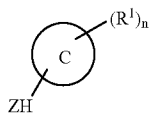

(IV)

(wherein ring C, $R^1$, Z and n are as defined hereinbefore) to obtain compounds of the formula I and salts thereof. A convenient displaceable moiety $L^1$ is, for example, a halogeno, alkoxy (preferably $C_{1-4}$alkoxy), aryloxy, alkylsulphanyl, arylsulphanyl, alkoxyalkylsulphanyl or sulphonyloxy group, for example a chloro, bromo, methoxy, phenoxy, methylsulphanyl, 2-methoxyethylsulphanyl, methanesulphonyloxy or toluene-4-sulphonyloxy group.

The reaction is advantageously effected in the presence of a base. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, calcium carbonate, cesium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trimethylsilyl)amide, potassium amide or potassium bis(trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethyl sulphoxide. The reaction is conveniently effected at a temperature in the range, for example, 10 to 150° C., preferably in the range 20 to 90° C.

Where $R^1$ or $R^2$ contains a heterocyclic ring with a substituent it is possible to add the substituent after process (a) above using standard procedures of organic chemistry. Thus for example a compound of formula III as defined hereinbefore but wherein $R^2$ contains an unsubstituted heterocyclic ring may be reacted with a compound of formula IV as defined hereinbefore to give an intermediate compound in which $R^2$ contains an unsubstituted heterocyclic ring. The intermediate compound can then be substituted on the heterocyclic ring in $R^2$ using standard organic chemistry techniques to give a final compound of formula I.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) Production of those compounds of formula I and salts thereof wherein at least one $R^2$ is $R^5X^1$ or $Q^1X^1$ wherein $R^5$, $Q^1$ are as defined hereinbefore, and $X^1$ is —O—, —S—, —OC(O)— or —NR$^{10}$— (wherein R$^{10}$ independently represents hydrogen, $C_{1-3}$alkyl or $C_{1-3}$alkoxy$C_{2-3}$alkyl) can be achieved by the reaction, conveniently in the presence of a base (as defined hereinbefore in process (a)) of a compound of the formula V:

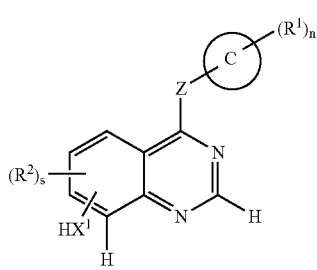

(V)

(wherein ring C, Z, $R^1$, $R^2$ and n are as hereinbefore defined and $X^1$ is as hereinbefore defined in this section and s is an integer from 0 to 2) with one of the compounds of the formulae VIa-b:

$R^5$-$L^1$ (VIa)

$Q^1$-$L^1$ (VIb)

(wherein $R^5$, $Q^1$ and $L^1$ are as hereinbefore defined), $L^1$ is a displaceable moiety for example a halogeno or sulphonyloxy group such as a bromo, methanesulphonyloxy or toluene-4-sulphonyloxy group, or $L^1$ may be generated in situ from an alcohol under standard Mitsunobu conditions ("Organic Reactions", John Wiley & Sons Inc, 1992, vol 42, chapter 2, David L Hughes). The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(c) Compounds of the formula I and salts thereof wherein at least one $R^2$ is $R^5X^1$ or $Q^1X^1$ wherein $R^5$ and $Q^1$ are as defined hereinbefore, and $X^1$ is —O—, —S—, —OC(O)— or —NR$^{10}$— (wherein $R^{16}$ represents hydrogen, $C_{1-3}$alkyl or $C_{1-3}$alkoxy$C_{2-3}$alkyl) may be prepared by the reaction of a compound of the formula VII:

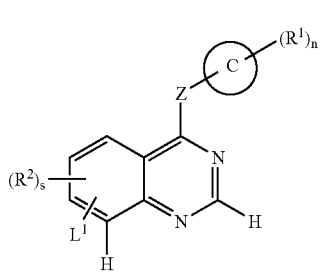

(VII)

with one of the compounds of the formulae VIIIa-b:

$R^5$—$X^1$—H (VIIIa)

$Q^1$-$X^1$—H (VIIIb)

(wherein $L^1$, $R^1$, $R^2$, $R^5$, $Q^1$ ring C, Z, n and s are all as hereinbefore defined and $X^1$ is as hereinbefore defined in this section). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(d) Compounds of the formula I and salts thereof wherein at least one $R^2$ is $R^5X^1$ or $Q^1X^1$ wherein $X^1$ is as defined hereinbefore, $R^5$ is $C_{1-5}$alkyl$R^{113}$, wherein $R^{113}$ is selected from one of the following nine groups:

1) $X^{19}C_{1-3}$alkyl (wherein $X^{19}$ represents —O—, —S—, —SO$_2$—, —NR$^{114}$C(O)— or —NR$^{115}$SO$_2$— (wherein $R^{114}$ and $R^{115}$ which may be the same or different are each hydrogen, $C_{1-3}$alkyl or $C_{1-3}$alkoxy$C_{2-3}$alkyl);
2) NR$^{116}$R$^{117}$ (wherein $R^{116}$ and $R^{117}$ which may be the same or different are each hydrogen, $C_{1-3}$alkyl or $C_{1-3}$alkoxy$C_{2-3}$alkyl);
3) $X^{20}C_{1-5}$alkyl$X^5R^{22}$ (wherein $X^{20}$ represents —O—, —S—, —SO$_2$—, —NR$^{118}$C(O)—, —NR$^{119}$SO$_2$— or —NR$^{120}$— (wherein $R^{118}$, $R^{119}$, and $R^{120}$ which may be the same or different are each hydrogen, $C_{1-3}$alkyl or $C_{1-3}$alkoxy$C_{2-3}$alkyl) and $X^5$ and $R^{22}$ are as defined hereinbefore);
4) $R^{28}$ (wherein $R^{28}$ is as defined hereinbefore);
5) $X^{21}R^{29}$ (wherein $X^{21}$ represents —O—, —S—, —SO$_2$—, —NR$^{121}$C(O)—, —NR$^{122}$SO$_2$—, or —NR$^{123}$— (wherein $R^{121}$, $R^{122}$, and $R^{123}$ which may be the same or different are each hydrogen, $C_{1-3}$alkyl or $C_{1-3}$alkoxy$C_{2-3}$alkyl) and $R^{29}$ is as defined hereinbefore); and
6) $X^{22}C_{1-3}$alkyl$R^{29}$ (wherein $X^{22}$ represents —O—, —S—, —SO$_2$—, NR$^{124}$C(O)—, —NR$^{125}$SO$_2$— or NR$^{126}$— (wherein $R^{124}$, $R^{125}$ and $R^{126}$ each independently represents hydrogen, $C_{1-3}$alkyl or $C_{1-3}$alkoxy$C_{2-3}$alkyl) and $R^{29}$ is as defined hereinbefore);
7) $R^{29}$ (wherein $R^{29}$ is as defined hereinbefore);
8) $X^{22}C_{1-4}$-alkyl$R^{28}$ (wherein $X^{22}$ and $R^{28}$ are as defined hereinbefore); and
9) $R^{54}(C_{1-4}$alkyl$)_q(X^9)_rR^{55}$ (wherein q, r, $X^9$, $R^{54}$ and $R^{55}$ are as defined hereinbefore);

$Q^1$ is $C_{1-5}$alkyl$Q^{27}$ wherein $Q^{27}$ is selected from one of the following six groups:
1) $Q^{13}$-C(O)—$C_{1-4}$alkyl$Q^{14}$ (wherein $Q^{13}$ and $Q^{14}$ are as defined hereinbefore);
2) $W^1Q^2$ (wherein $W^1$ and $Q^2$ are as defined hereinbefore);
3) $Q^2$ (wherein $Q^2$ is as defined hereinbefore);
4) $W^2C_{1-4}$alkyl$Q^2$ (wherein $W^2$ and $Q^2$ are as defined hereinbefore);
5) $Q^{15}(C_{1-4}$alkyl$)_j(W^2)_kQ^{16}$ (wherein $W^2$, j, k, $Q^{15}$ and $Q^{16}$ are as defined hereinbefore);
6) $Q^{15}C_{1-4}$alkanoyl$Q^{16n}$ (wherein $Q^{15}$ and $Q^{16}$ are as defined hereinbefore); may be prepared by reacting a compound of the formula IX:

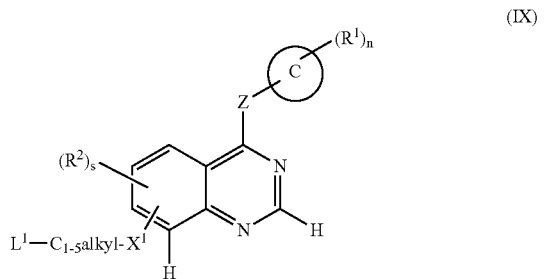

(wherein $L^1$, $X^1$, $R^1$, $R^2$, ring C, Z, n and s are as hereinbefore defined) with one of the compounds of the formulae Xa-b:

R$^{113}$—H  (Xa)

Q$^{27}$-H  (Xb)

(wherein $R^{113}$ and $Q^{27}$ are as defined hereinbefore) to give a compound of the formula I or salt thereof. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Where $R^1$ or $R^2$ contains a heterocyclic ring with a substituent it is possible to add the substituent after process (d) above using standard procedures of organic chemistry. Thus for example a compound of formula III as defined hereinbefore but wherein $R^2$ contains an unsubstituted heterocyclic ring may be reacted with a compound of formula IV as defined hereinbefore to give an intermediate compound in which $R^2$ contains an unsubstituted heterocyclic ring. The intermediate compound can then be substituted on the heterocyclic ring in $R^2$ using standard organic chemistry techniques to give a final compound of formula I.Processes (a), Processes (a) and (b) are the more preferred.

Process (d) is also preferred.

(e) The production of those compounds of the formula I and salts thereof wherein one or more of the substituents $(R^2)_m$ is represented by —NR$^{127}$R$^{128}$, where one (and the other is hydrogen) or both of $R^{127}$ and $R^{128}$ are $C_{1-3}$alkyl, may be effected by the reaction of compounds of formula I wherein the substituent $(R^2)_m$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents $R^2$ is an amino group may be effected by the reduction of a corresponding compound of formula I wherein the substituent(s) at the corresponding position(s) of the quinazoline group is/are a nitro group(s). The reduction may conveniently be effected as described in process (i) hereinafter. The production of a compound of formula I and salts thereof wherein the substituent(s) at the corresponding position(s) of the quinazoline group is/are a nitro group(s) may be effected by the processes described hereinbefore and hereinafter in processes (a-d) and (i-v) using a compound selected from the compounds of the formulae (I-XXII) in which the substituent(s) at the corresponding position(s) of the quinazoline group is/are a nitro group(s).

(f) Compounds of the formula I and salts thereof wherein $X^1$ is —SO— or —SO$_2$— may be prepared by oxidation from the corresponding compound in which $X^1$ is —S— or —SO— (when $X^1$ is —SO$_2$— is required in the final product). Conventional oxidation conditions and reagents for such reactions are well known to the skilled chemist.

Synthesis of Intermediates (i) The compounds of formula III and salts thereof in which $L^1$ is halogeno may for example be prepared by halogenating a compound of the formula XI:

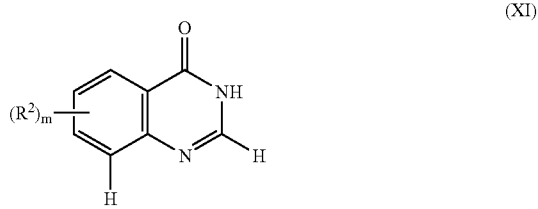

wherein $R^2$ and m are as hereinbefore defined).

Convenient halogenating agents include inorganic acid halides, for example thionyl chloride, phosphorus(III) chloride, phosphorus(V) oxychloride and phosphorus(V) chloride. The halogenation reaction may be effected in the presence of an inert solvent or diluent such as for example a halogenated solvent such as methylene chloride, trichloromethane or carbon tetrachloride, or an aromatic hydrocarbon solvent such as benzene or toluene, or the reaction may be effected without the presence of a solvent. The reaction is conveniently effected at a temperature in the range, for example 10 to 150° C., preferably in the range 40 to 100° C.

The compounds of formula XI and salts thereof may, for example, be prepared by reacting a compound of the formula XII:

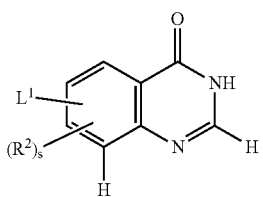

(XII)

(wherein $R^2$, s and $L^1$ are as hereinbefore defined) with one of the compounds of formulae VIIIa-d as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

Compounds of formula XI and salts thereof wherein at least one $R^2$ is $R^5X^1$ or $Q^1X^1$, wherein $R^5$ and $Q^1$ are as defined hereinbefore, and wherein $X^1$ is —O—, —S—, —SO—, —SO_2—, —C(O)—, —C(O)NR^7—, —SO_2NR^8— or —NR^{10}— (wherein $R^7$, $R^8$ and $R^{10}$ each independently represents hydrogen, $C_{1-3}$alkyl or $C_{1-3}$alkoxy$C_{2-3}$alkyl), may for example also be prepared by the reaction of a compound of the formula XIII:

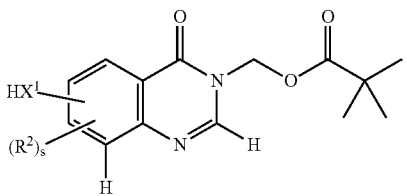

(XIII)

(wherein $R^2$ and s are as hereinbefore defined and $X^1$ is as hereinbefore defined in this section) with one of the compounds of formulae VIa-b as hereinbefore defined. The reaction may for example be effected as described for process (b) hereinbefore. The pivaloyloxymethyl group can then be cleaved by reacting the product with a base such as, for example, aqueous ammonia, triethylamine in water, an alkali metal or alkaline earth metal hydroxide or alkoxide, preferably aqueous ammonia, aqueous sodium hydroxide or aqueous potassium hydroxide, in a polar protic solvent such as an alcohol, for example methanol or ethanol. The reaction is conveniently effected at a temperature in the range 20 to 100° C., preferably in the range 20 to 50° C.

The compounds of formula XI and salts thereof may also be prepared by cyclising a compound of the formula XIV:

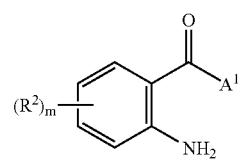

(XIV)

(wherein $R^2$ and m, are as hereinbefore defined, and $A^1$ is an hydroxy, alkoxy (preferably $C_{1-4}$alkoxy) or amino group) whereby to form a compound of formula XI or salt thereof. The cyclisation may be effected by reacting a compound of the formula XIV, where $A^1$ is an hydroxy or alkoxy group, with formamide or an equivalent thereof effective to cause cyclisation whereby a compound of formula XI or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XI may also be prepared by cyclising a compound of the formula XIV, where $A^1$ is an amino group, with formic acid or an equivalent thereof effective to cause cyclisation whereby a compound of formula XI or salt thereof is obtained. Equivalents of formic acid effective to cause cyclisation include for example a tri-$C_{1-4}$ alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethyl ether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof may for example be prepared by the reduction of the nitro group in a compound of the formula XV:

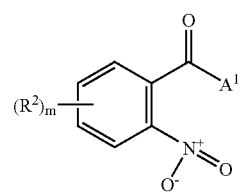

(XV)

(wherein $R^2$, m and $A^1$ are as hereinbefore defined) to yield a compound of formula XIV as hereinbefore defined. The reduction of the nitro group may conveniently be effected by any of the procedures known for such a transformation. The reduction may be carried out, for example, by stirring a solution of the nitro compound under hydrogen at 1 to 4 atmospheres pressure in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound under hydrogen at 2 atmospheres pressure in the presence of the activated metal and a solvent or diluent such as a mixture of water and alcohol, for example methanol or ethanol, at a temperature in the range, for example 50 to 150° C., conveniently at about 70° C.

Compounds of the formula XV and salts thereof may for example be prepared by the reaction of a compound of the formula XVI:

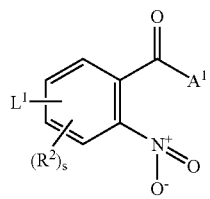

(XVI)

(wherein $R^2$, s, $L^1$ and $A^1$ are as hereinbefore defined) with one of the compounds of formulae VIIIa-d as hereinbefore defined to give a compound of the formula XV. The reaction of the compounds of formulae XVI and VIIIa-b is conveniently effected under conditions as described for process (c) hereinbefore.

Compounds of formula XV and salts thereof wherein at least one $R^2$ is $R^5X^1$ or $Q^1X^1$,
wherein $R^5$ and $Q^1$ are as defined hereinbefore, and wherein $X^1$ is —O—, —S—, —SO$_2$—, —C(O)—, —C(O)NR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxyC$_{2-3}$alkyl), may for example also be prepared by the reaction of a compound of the formula XVII:

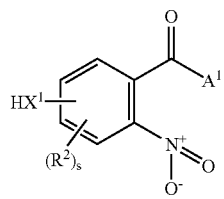

(XVII)

(wherein $R^2$, s and $A^1$ are as hereinbefore defined and $X^1$ is as hereinbefore defined in this section) with one of the compounds of formulae VIa-b as hereinbefore defined to yield a compound of formula XV as hereinbefore defined. The reaction of the compounds of formulae XVII and VIa-d is conveniently effected under conditions as described for process (b) hereinbefore.

The compounds of formula III and salts thereof wherein at least one $R^2$ is $R^5X^1$ and wherein $X^1$ is —CH$_2$— may be prepared for example as described above from a compound of the formula XV (in which $R^2$ is —CH$_3$) or XIII (in which HX$^1$— is —CH$_3$), by radical bromination or chlorination to give a —CH$_2$Br or —CH$_2$Cl group which may then be reacted with a compound of the formula $R^5$—H under standard conditions for such substitution reactions.

The compounds of formula III and salts thereof wherein at least one $R^2$ is $R^5X^1$ and wherein $X^1$ is a direct bond may be prepared for example as described above from a compound of the formula XI, wherein the $R^5$ group is already present in the intermediate compounds (for example in a compound of the formula XV) used to prepare the compound of formula XI.

The compounds of formula III and salts thereof wherein at least one $R^2$ is $R^5X^1$ and wherein $X^1$ is —NR$^6$C(O)— or —NR$^9$SO$_2$— may be prepared for example from a compound of the formula XIII in which HX$^1$— is an —NHR$^6$— or —NHR$^9$— group (prepared for example from an amino group (later functionalised if necessary) by reduction of a nitro group) which is reacted with an acid chloride or sulfonyl chloride compound of the formula $R^5$COCl or $R^5$SO$_2$Cl.

The compounds of formula III and salts thereof wherein at least one $R^2$ is $R^5X^1$ or $Q^1X^1$, wherein $R^5$ and $Q^1$ are as defined hereinbefore, and wherein $X^1$ is —O—, —S—, —SO$_2$—, —OC(O)—, —C(O)NR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxyC$_{2-3}$alkyl), may also be prepared for example by reacting a compound of the formula XVIII:

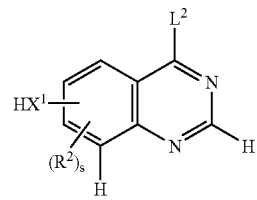

(XVIII)

(wherein $R^2$ and s are as hereinbefore defined, $X^1$ is as hereinbefore defined in this section and $L^2$ represents a displaceable protecting moiety) with one of the compounds of formulae VIa-b as hereinbefore defined, whereby to obtain a compound of formula III in which $L^1$ is represented by $L^2$.

A compound of formula XVIII is conveniently used in which $L^2$ represents a phenoxy group which may if desired carry up to 5 substituents, preferably up to 2 substituents, selected from halogeno, nitro and cyano. The reaction may be conveniently effected under conditions as described for process (b) hereinbefore.

The compounds of formula XVIII and salts thereof may for example be prepared by deprotecting a compound of the formula XIX:

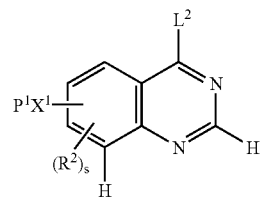

(XIX)

(wherein $R^2$, s and $L^2$ are as hereinbefore defined, $P^1$ is a protecting group and $X^1$ is as hereinbefore defined in the section describing compounds of the formula XVIII). The choice of protecting group $P^1$ is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and amino acetal derivatives (for example benzyloxymethyl). The removal of such a protecting group may be effected by any of the procedures known for such a transformation, including those reaction conditions indicated in standard texts such as that indicated hereinbefore, or by a related procedure. Deprotection may be effected by techniques well known in the literature, for example where $P^1$ represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XI as hereinbefore defined, followed by introduction of halide to the compound of formula XI, thus obtained as hereinbefore defined, to yield a compound of formula III in which $L^1$ represents halogen.

(ii) Compounds of formula IV and salts thereof in which ring C is indolyl may be prepared by any of the methods known in the art, such as for example those described in "Indoles Part I", "Indoles Part II", 1972 John Wiley & Sons Ltd and "Indoles Part III" 1979, John Wiley & Sons Ltd, edited by W. J. Houlihan. Compounds of formula IV and salts thereof in which ring C is indolyl may be prepared by any of the methods described in International Patent Application No. PCT/GB03/00343 or in WO 00/47212.

Compounds of formula IV and salts thereof in which ring C is quinolinyl may be prepared by any of the methods known in the art, such as for example those described in "The Chemistry of Heterocyclic Compounds: Quinolines Parts I, II and III", 1982 (Interscience publications) John Wiley & Sons Ltd, edited by G. Jones, and in "Comprehensive Heterocyclic Chemistry Vol II by A. R. Katritzky", 1984 Pergamon Press, edited by A. J. Boulton and A McKillop.

Compounds of formula IV and salts thereof in which ring C is indazolyl may be prepared by any of the methods known in the art, such as for example those described in Petitcoles, Bull. Soc. Chim. Fr. 1950, 466 and Davies, J. Chem. Soc. 1955, 2412.

Compounds of formula IV and salts thereof in which ring C is azaindolyl may be prepared by any of the methods known in the art, such as for example those described in Heterocycles 50, (2), 1065-1080, 1999.

(iii) Compounds of formula V as hereinbefore defined and salts thereof may be made by deprotecting the compound of formula XX:

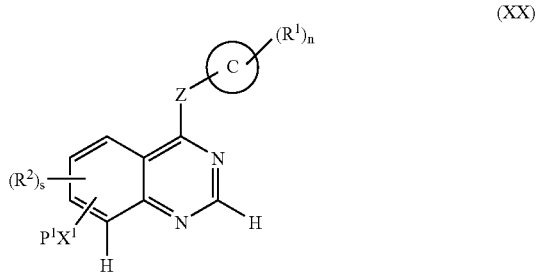

(XX)

(wherein ring C, Z, $R^1$, $R^2$, $P^1$ n and s are as hereinbefore defined and $X^1$ is as hereinbefore defined in the section describing compounds of the formula V) by a process for example as described in (i) above.

Compounds of the formula XX and salts thereof may be made by reacting compounds of the formulae XIX and IV as hereinbefore defined, under the conditions described in (a) hereinbefore, to give a compound of the formula XX or salt thereof (iv) Compounds of the formula VII and salts thereof may be made by reacting a compound of the formula XXI:

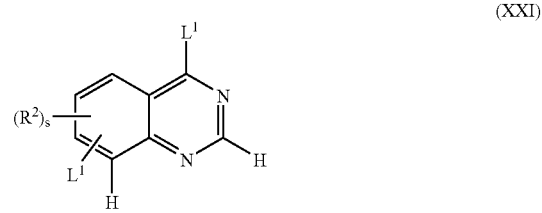

(XXI)

(wherein $R^2$, s and each $L^1$ are as hereinbefore defined and the $L^1$ in the 4-position and the other $L^1$ in a further position on the quinazoline ring may be the same or different) with a compound of the formula IV as hereinbefore defined, the reaction for example being effected by a process as described in (a) above.

(v) Compounds of formula IX as defined hereinbefore and salts thereof may for example be made by the reaction of compounds of formula V as defined hereinbefore with compounds of the formula XXII:

$$L^1\text{-}C_{1\text{-}5}\text{alkyl-}L^1 \qquad (XXII)$$

(wherein $L^1$ is as hereinbefore defined) to give compounds of formula IX or salts thereof. The reaction may be effected for example by a process as described in (b) above.

(vi) Intermediate compounds wherein $X^1$ is —SO— or —$SO_2$— may be prepared by oxidation from the corresponding compound in which $X^1$ is —S— or —SO— (when $X^1$ is —$SO_2$— is required in the final product). Conventional oxidation conditions and reagents for such reactions are well known to the skilled chemist.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel and these are provided as a further feature of the invention. The preparation of these compounds is as described herein and/or is by methods well known to persons skilled in the art of organic chemistry.

The identification of compounds which inhibit angiogenesis and/or increased vascular permeability, which potently inhibit the tyrosine kinase activity associated with the VEGF receptor KDR and are selective for KDR over Flt-1, which have less extended plasma pharmacokinetics and which are inactive or only weakly active in the hERG assay, is desirable and is the subject of the present invention.

These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19-25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt-1 (Genbank accession number X51602), a 1.7 kb DNA fragment encoding most of the cytoplasmic domain, commencing with methionine 783 and including the termination codon, described by Shibuya et al (Oncogene, 1990, 5: 519-524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(5f21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R1 receptor, Genbank accession number X51803) may be cloned and expressed in a similar manner.

For expression of cFlt-1 tyrosine kinase activity, Sf21 cells were infected with plaque-pure cFlt-1 recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microliters of 40 mM manganese(II) chloride containing 8 µM adenosine-5'-triphosphate (ATP) was added to all test wells except "blank" control wells which contained manganese(II) chloride without ATP. To start the reactions 50 µl of freshly diluted enzyme was added to each well and the plates were incubated at ambient temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at ambient temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at ambient temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20-60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1 \times 10^6$ CaLu-6 cells/mouse in 100 µl of a 50% (v/v) solution of Matrigel in serum free culture medium. Ten days after cellular implant, mice were allocated to groups of 8-10, so as to achieve comparable group mean volumes. Tumours were measured using vernier calipers and volumes were calculated as: $(l \times w) \times \sqrt{(l \times w)} \times (\pi/6)$, where l is the longest diameter and w the diameter perpendicular to the longest. Test compounds were administered orally once daily for a minimum of 21 days, and control animals received compound diluent. Tumours were measured twice weekly. The level of growth inhibition was calculated by comparison of the mean tumour volume of the control group versus the treatment group using a Student T test and/or a Mann-Whitney Rank Sum Test. The inhibitory effect of compound treatment was considered significant when p<0.05.

d) hERG-encoded Potassium Channel Inhibition Test

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at ambient temperature (~20° C.). This chamber was fixed to the stage of an inverted, phase-contrast microscope Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| MgCl$_2$ | 1 | 1 |
| CaCl$_2$ | — | 1.8 |
| HEPES | 10 | 10 |

-continued

| | | |
|---|---|---|
| glucose | — | 10 |
| Na$_2$ATP | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency (IC$_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Although the pharmacological properties of the compounds of formula I vary with structural change, in general, activity possessed by compounds of the formula I, may be demonstrated at the following concentrations or doses in one or more of the above tests (a), (b) and (c)

Test (a):—IC$_{50}$ in the range, for example, <5 µM;
Test (b):—IC$_{50}$ in the range, for example, 0.001-5 µM;
Test (c):—activity in the range, for example, 0.1-100 mg/kg;

Example 11 of the present application has an IC$_{50}$ value in the enzyme assay (a) of 0.104 µM against KDR.

Example 11 of the present application has an IC$_{50}$ of 10.1 µM in the hERG assay (d).

Plasma pharmacokinetics may be assessed by measuring plasma half-life in vivo. The longer the plasma half-life in vivo the more extended are the plasma pharmacokinetics.

Compounds of the present invention have less extended plasma pharmacokinetics than compounds of WO 00/47212. Compounds of the present invention have shorter half-lives in vivo than compounds of WO 00/47212.

Plasma half-life in vivo may be determined by standard methods which are well-known in the art of plasma pharmacokinetics. Any species may be used and the plasma half-life determined by standard methodology, for example plasma half-life may be measured in rat, dog, monkey or human.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5-5000 mg per square meter body area of the animal, i.e. approximately 0.1-100 mg/kg. A unit dose in the range, for example, 1-100 mg/kg, preferably 1-50 mg/kg is envisaged and this normally provides a therapeutically-effective dose. A unit dose form such as a tablet or capsule will usually contain, for example 1-250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 0.1-50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents such as those which inhibit the effects of vascular endothelial growth factor, (for example the anti-vascular endothelial cell growth factor antibody bevacizumab [Avastin™], and those that work by different mechanisms from those defined hereinbefore (for example linomide, inhibitors of integrin $\alpha v\beta 3$ function, angiostatin, razoxin, thalidomide), and including vascular targeting agents (for example combretastatin phosphate and compounds disclosed in International Patent Applications WO00/40529, WO 00/41669, WO01/92224, WO02/04434 and WO02/08213 and the vascular damaging agents described in International Patent Application Publication No. WO 99/02166 the entire disclosure of which document is incorporated herein by reference, (for example N-acetylcolchinol-O-phosphate));

(ii) cytostatic agents such as antioestrogens (for example tamoxifen, toremifene, raloxifene, droloxifene, iodoxyfene), oestrogen receptor down regulators (for example fulvestrant), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide, buserelin), inhibitors of 5α-reductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor), such inhibitors include growth factor antibodies, growth factor receptor antibodies, (for example the anti-erbb2 antibody trastuzumab [Herceptin™] and the anti-erbb1 antibody cetuximab [C225]), farnesyl transferase inhibitors, tyrosine kinase inhibitors for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)) and serine/threonine kinase inhibitors; and (iii) antiproliferative/antineoplastic drugs and combinations thereof, as used in medical oncology, such as antimetabolites (for example antifolates like methotrexate, fluoropyrimidines like 5-fluorouracil, tegafur, purine and adenosine analogues, cytosine arabinoside); antitumour antibiotics (for example anthracyclines like adriamycin, bleomycin, doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine, vinblastine, vindesine, vinorelbine, and taxoids like taxol, taxotere); topoisomerase inhibitors (for example epipodophyllotoxins like etoposide and teniposide, amsacrine, topotecan, camptothecin and also irinotecan); also enzymes (for example asparaginase); and thymidylate synthase inhibitors (for example raltitrexed); and additional types of chemotherapeutic agent include:

(iv) biological response modifiers (for example interferon);
(v) antibodies (for example edrecolomab);
(vi) antisense therapies, for example those which are directed to the targets listed above, such as ISIS 2503, an anti-ras antisense;

(vii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

For example such conjoint treatment may be achieved by way of the simultaneous, sequential or separate administration of a compound of formula I as defined hereinbefore, and a vascular targeting agent described in WO 99/02166 such as N-acetylcolchinol-O-phosphate (Example 1 of WO 99/02166).

It is known from WO 01/74360 that antiangiogenics can be combined with antihypertensives. A compound of the present invention can also be administered in combination with an antihypertensive. An antihypertensive is an agent which lowers blood pressure, see WO 01/74360 which is incorporated herein by reference.

Thus according to the present invention there is provided a method of treatment of a disease state associated with angiogenesis which comprises the administration of an effective amount of a combination of a compound of the present invention or a pharmaceutically acceptable salt thereof and an anti-hypertensive agent to a warm-blooded animal, such as a human being.

According to a further feature of the present invention there is provided the use of a combination of a compound of the present invention or a pharmaceutically acceptable salt thereof and an anti-hypertensive agent for use in the manufacture of a medicament for the treatment of a disease state associated with angiogenesis in a warm-blooded mammal, such as a human being.

According to a further feature of the present invention there is provided a pharmaceutical composition comprising a compound of the present invention or a pharmaceutically acceptable salt thereof and an anti-hypertensive agent for the treatment of a disease state associated with angiogenesis in a warm-blooded mammal, such as a human being.

According to a further aspect of the present invention there is provided a method for producing an anti-angiogenic and/or vascular permeability reducing effect in a warm-blooded animal, such as a human being, which comprises administering to said animal an effective amount of a combination of a compound of the present invention or a pharmaceutically acceptable salt thereof and an anti-hypertensive agent.

According to a further aspect of the present invention there is provided the use of a combination of a compound of the present invention or a pharmaceutically acceptable salt thereof and an anti-hypertensive agent for the manufacture of a medicament for producing an anti-angiogenic and/or vascular permeability reducing effect in a warm-blooded mammal, such as a human being.

Preferred antihypertensive agents are calcium channel blockers, angiotensin converting enzyme inhibitors (ACE inhibitors), angiotensin II receptor antagonists (A-II antagonists), diuretics, beta-adrenergic receptor blockers (β-blockers), vasodilators and alpha-adrenergic receptor blockers (α-blockers). Particular antihypertensive agents are calcium channel blockers, angiotensin converting enzyme inhibitors (ACE inhibitors), angiotensin II receptor antagonists (A-II antagonists) and beta-adrenergic receptor blockers (β-blockers), especially calcium channel blockers.

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, lymphoedema, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation including age-related macular degeneration. Cancer may affect any tissue and includes leukaemia, multiple myeloma and lymphoma. In particular such compounds of the invention are expected to slow advantageously the growth of primary and recurrent solid tumours of, for example, the colon, breast, prostate, lungs and skin. More particularly such compounds of the invention are expected to inhibit any form of cancer associated with VEGF including leukaemia, multiple myeloma and lymphoma and also, for example, the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:—

(i) evaporations were carried out by rotary evaporation in vacuo and work-up procedures were carried out after removal of residual solids such as drying agents by filtration;

(ii) operations were carried out at ambient temperature, that is in the range 18-25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(vii) intermediates were not generally fully characterised and purity was assessed by thin layer chromatography (TLC), high-performance liquid chromatography (HPLC), infra-red (IR) or NMR analysis;

(viii) HPLC were run under 2 different conditions:
1) on a TSK Gel super ODS 2 μM 4.6 mm×5 cm column, eluting with a gradient of methanol in water (containing 1% acetic acid) 20 to 100% in 5 minutes. Flow rate 1.4 ml/minute. Detection: U.V. at 254 nm and light scattering detections;
2) on a TSK Gel super ODS 2 μM 4.6 mm×5 cm column, eluting with a gradient of methanol in water (containing 1% acetic acid) 0 to 100% in 7 minutes. Flow rate 1.4 ml/minute. Detection: U.V. at 254 nm and light scattering detections.

(ix) petroleum ether refers to that fraction boiling between 40-60° C.

(x) the following abbreviations have been used:—
DMF N,N-dimethylformamide
DMSO dimethylsulphoxide
TFA trifluoroacetic acid
DMA dimethylacetamide
LC-MS HPLC coupled to mass spectrometry

EXAMPLE 1

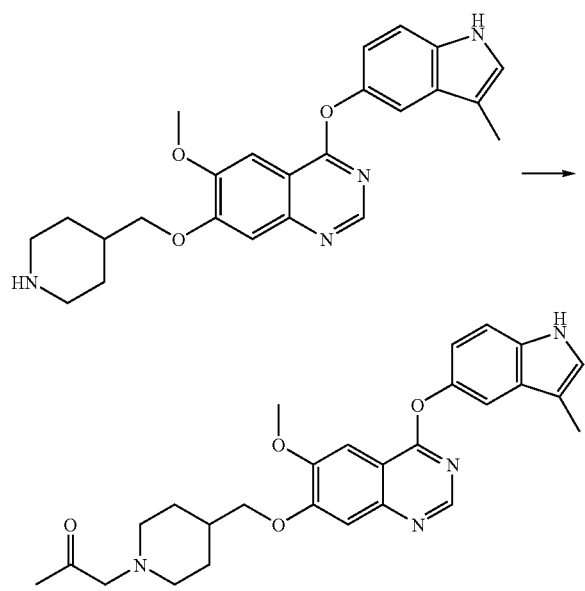

A mixture of 6-methoxy-4-[(3-methyl-1H-indol-5-yl)oxy]-7-[(piperidin-4-yl)methoxy]quinazoline (0.2 g), chloroacetone (0.046 ml), potassium carbonate (0.1 g) and DMF (6 ml) was stirred and heated to 70° C. for 1 hour. The mixture was cooled to ambient temperature, the precipitate was removed by filtration, the solvent was removed by evaporation under vacuum and the residue was purified by column chromatography on silica using increasingly polar solvent mixtures, starting with dichloromethane and ending dichloromethane/methanol (93/7). Evaporation of the solvents gave a foam which was triturated under ether/pentane (70/30) to give a solid which was collected by filtration and dried under vacuum to give 7-{[1-(acetylmethyl)piperidin-4-yl]methoxy}-6-methoxy-4-[(3-methyl-1H-indol-5-yl)oxy]quinazoline (0.074 g).

Mass Spectrum: M+H$^+$475

$^1$H NMR Spectrum: (DMSOd$_6$) 1.40 (m, 2H), 1.80 (m, 3H), 2.05 (m, 5H), 2.25 (s, 3H), 2.80 (d, 2H), 3.15 (s, 2H), 4.0 (s, 3H), 4.10 (d, 2H), 6.95 (d, 1H), 7.20 (s, 1H), 7.35 (m, 3H), 7.60 (s, 1H), 8.50 (s, 1H)

Elemental Analysis Found C, 68.38; H, 6.59; N, 11.68; C$_{27}$H$_{30}$N$_4$O$_4$. Requires C, 68.34; H, 6.37; N, 11.81%

The starting material was prepared as follows:

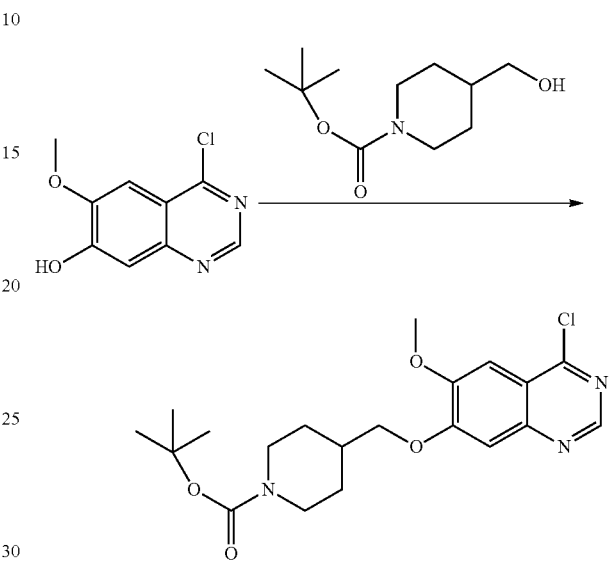

A mixture of 2-amino-4-benzyloxy-5-methoxybenzamide (10 g, 0.04 mol), (J. Med. Chem. 1977, vol 20, 146-149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The mixture was evaporated, water was added to the residue, the solid was filtered off, washed with water and dried (MgSO$_4$). Recrystallisation from acetic acid gave 7-benzyloxy-6-methoxy-3,4-dihydroquinazolin-4-one (8.7 g, 84%).

10% Palladium on carbon (8.3 g) was added to a suspension of 7-benzyloxy-6-methoxy-3,4-dihydroquinazolin-4-one (50 g, 0.177 mol) in dimethylformamide (800 ml) under nitrogen. Ammonium formate (111.8 g, 1.77 mol) was then added in portions over 5 minutes. The reaction mixture was stirred for one hour at ambient temperature then heated to 80° C. for a further hour. The reaction mixture was filtered hot through diatomaceous earth and the residues washed with dimethylformamide. The filtrate was then concentrated and the residue suspended in water. The pH was adjusted to 7.0 using 2M sodium hydroxide and the resulting mixture was stirred at ambient temperature for one hour. The solid was filtered, washed with water and dried over phosphorus pentoxide yielding 7-hydroxy-6-methoxy-3,4-dihydroquinazolin-4-one as a white solid (20.52 g, 60%).

$^1$H NMR Spectrum: (DMSOd$_6$) 3.85 (s, 3H), 6.95 (s, 1H), 7.40 (s, 1H), 7.85 (s, 1H)

MS-ESI: 193 [M+H]+

Pyridine (20 ml) was added to a suspension of 7-hydroxy-6-methoxy-3,4-dihydroquinazolin-4-one (20.5 g, 107 mmol) in acetic anhydride (150 ml, 1.6 mol). The reaction mixture was heated to 120° C. for three hours, during which time the solid dissolved. The reaction mixture was allowed to cool then poured into ice-water (900 ml). The reaction mixture was stirred for one hour then the solid was removed by filtration and dried over phosphorus pentoxide yielding 7-acetoxy-6-methoxy-3,4-dihydroquinazolin-4-one as a white solid (20.98 g, 84%).

$^1$H NMR Spectrum: (DMSOd$_6$) 2.25 (s, 3H), 3.85 (s, 3H), 7.40 (s, 1H), 7.60 (s, 1H), 8.00 (s, 1H)

MS-ESI: 235 [M+H]+

7-Acetoxy-6-methoxy-3,4-dihydroquinazolin-4-one (1 g, 4.3 mmol) was suspended in thionyl chloride (10.5 ml). One drop of dimethylformamide was added and the reaction was heated to 80° C. for two hours, during which time the solid dissolved. The reaction mixture was cooled and the thionyl chloride was removed in vacuo. The residue was azeotroped with toluene before being suspended in methylene chloride. A solution of 10% ammonia in methanol (40 ml) was added and the reaction mixture was heated to 80° C. for 15 minutes. After cooling the solvents were removed in vacuo and the residue redissolved in water (10 ml) and the pH adjusted to 7.0 with 2M hydrochloric acid. The resulting solid was filtered, washed with water and dried over phosphorus pentoxide yielding 4-chloro-7-hydroxy-6-methoxyquinazoline as a white solid (680 mg, 75%).

$^1$H NMR Spectrum: (DMSOd$_6$) 4.00 (s, 3H), 7.25 (s, 1H), 7.35 (s, 1H), 8.75 (s, 1H)

MS-ESI: 211-213 [M+H]+

While maintaining the temperature in the range 0-5° C., a solution of di-tert-butyl dicarbonate (41.7 g, 0.19 mol) in ethyl acetate (75 ml) was added in portions to a solution of ethyl 4-piperidinecarboxylate (30 g, 0.19 mol) in ethyl acetate (150 ml) cooled at 5° C. After stirring for 48 hours at ambient temperature, the mixture was poured onto water (300 ml). The organic layer was separated, washed successively with water (200 ml), 0.1N aqueous hydrochloric acid (200 ml), saturated sodium hydrogen carbonate (200 ml) and brine (200 ml), dried (MgSO$_4$) and evaporated to give ethyl 4-(1-(tert-butoxycarbonyl)piperidine)carboxylate (48 g, 98%).

$^1$H NMR Spectrum: (CDCl$_3$) 1.25 (t, 3H); 1.45 (s, 9H); 1.55-1.70 (m, 2H); 1.8-2.0 (d, 2H); 2.35-2.5 (m, 1H); 2.7-2.95 (t, 2H); 3.9-4.1 (br s, 2H); 4.15 (q, 2H)

A solution of 1M lithium aluminium hydride in THF (133 ml, 0.133 mol) was added in portions to a solution of ethyl 4-(1-(tert-butoxycarbonyl)piperidine)carboxylate (48 g, 0.19 mol) in dry THF (180 ml) cooled at 0° C. After stirring at 0° C. for 2 hours, water (30 ml) was added followed by 2N sodium hydroxide (10 ml). The precipitate was removed by filtration through diatomaceous earth and washed with ethyl acetate. The filtrate was washed with water, brine, dried (MgSO$_4$) and evaporated to give 1-(tert-butoxycarbonyl)-4-(hydroxymethyl)piperidine (36.3 g, 89%).

To a suspension of 4-chloro-7-hydroxy-6-methoxyquinazoline (10 g) in dichloromethane (250 ml) were successively added: triphenyl phosphine (18.7 g) 1-(tert-butoxycarbonyl)-4-(hydroxymethyl)piperidine (12.2 g) and di-tert-butyl azodicarboxylate (16.4 g). The reaction mixture was stirred at ambient temperature for 18 hours. The mixture was concentrated to a third and purified by column chromatography on silica using a mixture of ethyl acetate/petroleum ether (3/7) as eluent. Removal of the solvent by evaporation gave 7-{[1-(tert-butoxycarbonyl)piperidin-4-yl]methoxy}-4-chloro-6-methoxyquinazoline as a beige solid (14g).

Mass Spectrum: M+H$^+$408 and 410

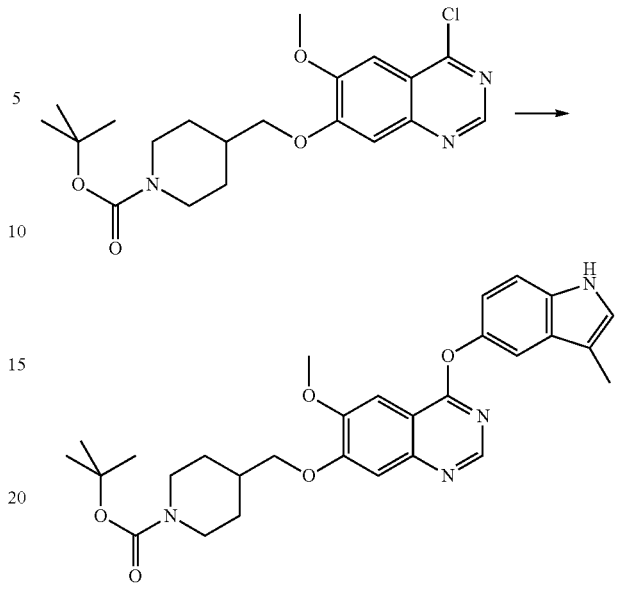

A mixture of 7-{[1-(tert-butoxycarbonyl)piperidin-4-yl]methoxy}-4-chloro-6-methoxyquinazoline (4.6 g), 5-hydroxy-3-methylindole (2 g), (Journal of Organic Chemistry 1993, 58, 3757), potassium carbonate (3.1 g) and DMF (20 ml) was stirred and heated to 90° C. for 2 hours. The solid was removed by filtration washed with acetonitrile and the combined filtrates concentrated to dryness under vacuum. The product so obtained was triturated under ether/petroleum ether (8/2), collected by filtration and dried to give 7-{[1-(tert-butoxycarbonyl)piperidin-4-yl]methoxy}-6-methoxy-4-[(3-methyl-1H-indol-5-yl)oxy]quinazoline (5.8 g).

Mass Spectrum: M+H$^+$519

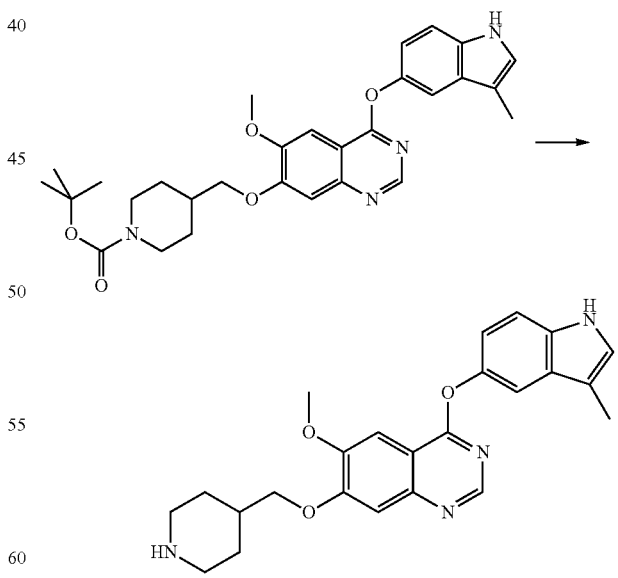

7-{[1-(tert-Butoxycarbonyl)piperidin-4-yl]methoxy}-6-methoxy-4-[(3-methyl-1H-indol-5-yl)oxy]quinazoline (5.8 g) was suspended in dichloromethane (40 ml) and cooled with an ice bath. TFA (17 ml) was added and the reaction mixture was stirred at this temperature for 1 hour. The volatiles were removed under vacuum and the residue triturated under water and dichloromethane. The pH was made basic to 12.5 with a 30% aqueous solution of sodium hydroxide while cooling with an ice bath. Extraction was done with a mixture of dichloromethane and methanol. The combined extracts were washed in turn with water and brine and dried over magnesium sulphate. The solvent was evaporated under vacuum and the residue was triturated under ether, filtered and dried to give 6-methoxy-4-[(3-methyl-1H-indol-5-yl)oxy]-7-[(piperidin-4-yl)methoxy]quinazoline (3.6 g).

Mass Spectrum: M+H$^+$419

$^1$H NMR Spectrum: (DMSOd$_6$ and CF$_3$CO$_2$D) 1.50 (m, 2H), 2.0 (m, 2H), 2.20 (m, 1H), 2.25 (s, 3H), 2.95 (m, 2H), 2.40 (m, 2H), 4.05 (s, 3H), 4.20 (d, 2H), 7.05 (d, 1H), 7.25 (s, 1H), 7.40 (d, 1H), 7.45 (d, 1H), 7.50 (s, 1H), 7.75 (s, 1H), 8.90 (s, 1H)

EXAMPLE 2

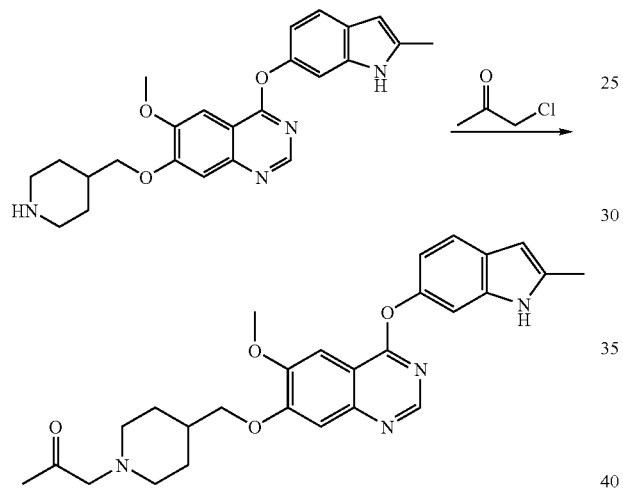

6-Methoxy-4-[(2-methyl-1H-indol-6-yl)oxy]-7-[(piperidin-4-yl)methoxy]quinazoline (0.2 g) was reacted with chloracetone (0.046 ml) using an analogous procedure to that described in Example 1 to give, after work up and purification, 7-{[1-(acetylmethyl)piperidin-4-yl]methoxy}-6-methoxy-4-[(2-methyl-1H-indol-6-yl)oxy]quinazoline (0.155 g) as a solid.

Mass Spectrum: M+H$^+$475

$^1$H NMR Spectrum: (DMSOd$_6$) 1.40 (m, 2H), 1.80 (m, 3H), 2.05 (m, 5H), 2.40 (s, 3H), 2.80 (d, 2H), 3.15 (s, 2H), 3.95 (s, 3H), 4.10 (d, 2H), 6.15 (s, 1H), 6.85 (d, 1H), 7.15 (s, 1H), 7.35 (s, 1H), 7.45 (d, 1H), 7.6 (s, 1H), 8.50 (s, 1H)

Elemental Analysis Found C, 67.52; H, 6.55; N, 11.75; C$_{27}$H$_{30}$N$_4$O$_4$ 0.2H$_2$O. Requires C, 68.34; H, 6.37; N, 11.81%

The starting material was prepared using an analogous procedure to that described in Example 1 but replacing 5-hydroxy-3-methylindole with 6-hydroxy-2-methylindole, (Eur. J. Med. Chem. 1975, 10, 187). Thus 7-{[1-(tert-butoxycarbonyl)piperidin-4-yl]methoxy}-4-chloro-6-methoxyquinazoline (4.6 g) and 6-hydroxy-2-methylindole (2 g) gave after coupling and deprotection 2.6 g of 6-methoxy-4-[(2-methyl-1H-indol-6-yl)oxy]-7-[(piperidin-4-yl)methoxy]quinazoline.

Mass Spectrum: M+H$^+$419

$^1$H NMR Spectrum: (DMSOd$_6$ and CF$_3$CO$_2$D) 1.55 (m, 2H), 2.0 (m, 2H), 2.25 (m, 1H), 2.40 (s, 3H), 2.95 (m, 2H), 3.35 (m, 2H), 4.05 (s, 3H), 4.20 (d, 2H), 6.20 (s, 1H), 6.90 (d, 1H), 7.25 (s, 1H), 7.50 (d, 1H), 7.55 (s, 1H), 7.80 (s, 1H), 8.95 (s, 1H)

EXAMPLE 3

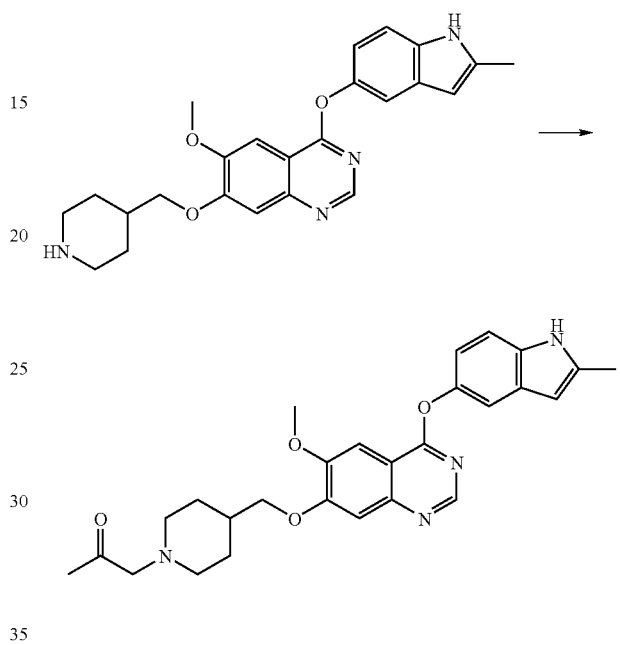

6-Methoxy-4-[(2-methyl-1H-indol-5-yl)oxy]-7-[(piperidin-4-yl)methoxy]quinazoline (0.25 g) was reacted with chloracetone (0.057 ml) using an analogous procedure to that described in Example 1 to give, after work up and purification, 7-{[1-(acetylmethyl)piperidin-4-yl]methoxy}-6-methoxy-4-[(2-methyl-1H-indol-5-yl)oxy]quinazoline (0.207 g) as a solid.

Mass Spectrum: M+H$^+$475

$^1$H NMR Spectrum: (DMSOd$_6$) 1.40 (m, 2H), 1.80 (m, 3H), 2.05 (m, 5H), 2.40 (s, 3H), 2.80 (d, 2H), 3.15 (s, 2H), 3.95 (s, 3H), 4.10 (d, 2H), 6.15 (s, 1H), 6.85 (d, 1H), 7.25 (s, 1H), 7.20 (d, 1H), 7.35 (s, 1H), 7.6 (s, 1H), 8.50 (s, 1H)

Elemental Analysis: Found C, 67.56; H, 6.44; N, 11.66; C$_{27}$H$_{30}$N$_4$O$_4$ 0.3H$_2$O 0.01ether. Requires C, 68.34; H, 6.37; N, 11.81%

The starting material was prepared using an analogous procedure to that described in Example 1 but replacing 5-hydroxy-3-methylindole with 5-hydroxy-2-methylindole. Thus 7-{[1-(tert-butoxycarbonyl)piperidin-4-yl]methoxy}-4-chloro-6-methoxyquinazoline (3 g) and 5-hydroxy-2-methylindole (1.3 g) gave after coupling and deprotection 1.7 g of 6-methoxy-4-[(2-methyl-1H-indol-5-yl)oxy]-7-[(piperidin-4-yl)methoxy]quinazoline.

Mass Spectrum: M+H$^+$419

$^1$H NMR Spectrum: (DMSOd$_6$) 1.55 (m, 2H), 2.0 (m, 2H), 2.25 (m, 1H), 2.40 (s, 3H), 2.95 (m, 2H), 3.35 (m, 2H), 4.05 (s, 3H), 4.20 (d, 2H), 6.20 (s, 1H), 6.95 (d, 1H), 7.35 (m, 2H), 7.50 (s, 1H), 7.75 (s, 1H), 8.95 (s, 1H)

EXAMPLE 4

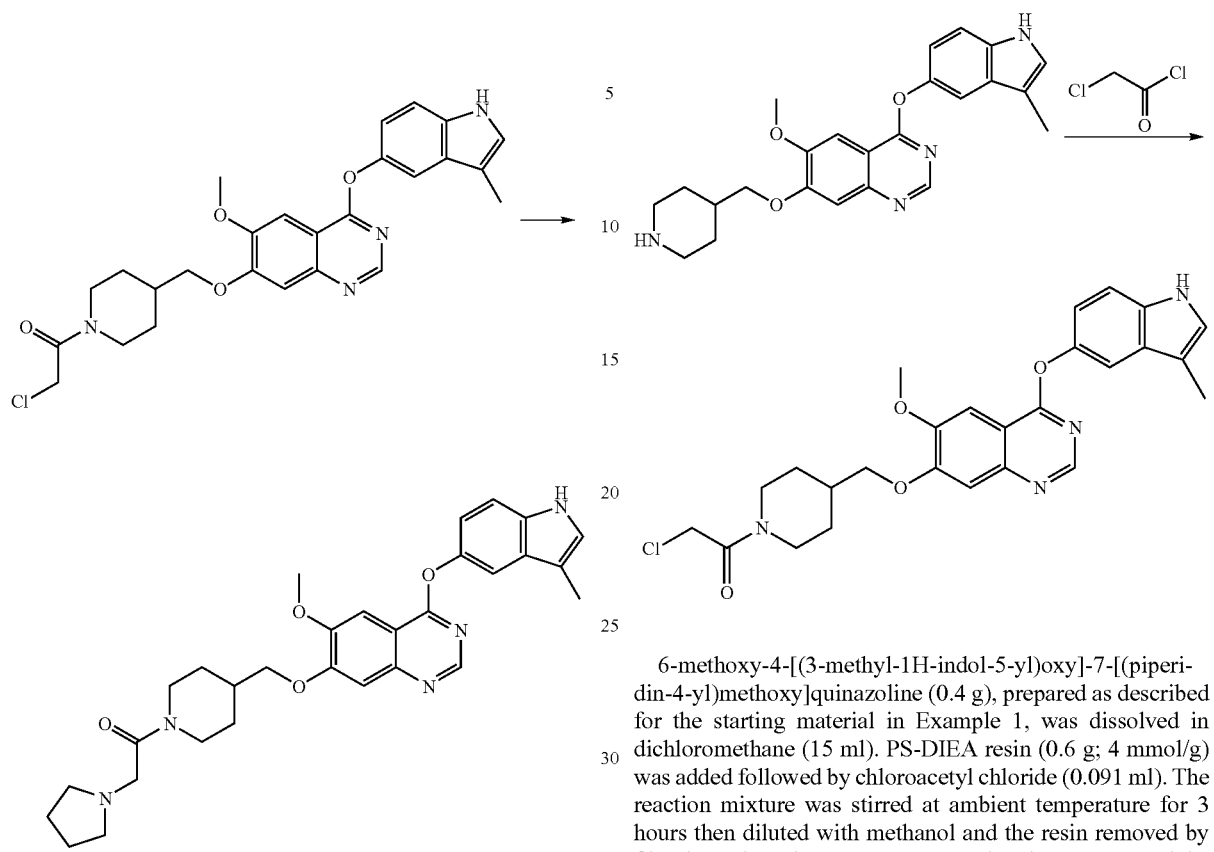

A mixture of 7-{[1-(chloroacetyl)piperidin-4-yl]methoxy}-6-methoxy-4-[(3-methyl-1H-indol-5-yl)oxy]quinazoline (0.118 g), pyrrolidine (0.059 ml), potassium iodide (0.01 g) and DMF (3 ml) was stirred and heated to 80° C. for 40 minutes. The mixture was cooled to ambient temperature, the solvent was removed by evaporation under vacuum and the residue was purified by column chromatography on silica using increasingly polar solvent mixtures, starting with dichloromethane and ending dichloromethane/methanol saturated with ammonia (3.5M) (94/6). Evaporation of the solvents gave a foam which was triturated under ether/pentane (70/30) to give a solid which was collected by filtration and dried under vacuum to give 6-methoxy-4-[(3-methyl-1H-indol-5-yl)oxy]-7-{[1-(pyrrolidin-1-ylacetyl)piperidin-4-yl]methoxy}quinazoline (0.096 g).

Mass Spectrum: M+H$^+$530

$^1$H NMR Spectrum: (DMSOd$_6$ and CF$_3$CO$_2$D) 1.25 (m, 1H), 1.40 (m, 1H), 1.90 (m, 4H), 2.05 (m, 2H), 2.25 (m, 4H), 2.80 (m, 1H), 3.05 (m, 2H), 3.15 (m, 1H), 3.60 (m, 2H), 3.70 (m, 1H), 4.05 (s, 3H), 4.15 (d, 2H), 4.40 (m, 3H), 7.0 (d, 1H), 7.25 (s, 1H), 7.40 (d, 1H), 7.45 (d, 1H), 7.50 (s, 1H), 7.75 (s, 1H), 8.90 (s, 1H)

Elemental Analysis Found C, 67.31; H, 7.01; N, 12.94;

C$_{30}$H$_{35}$N$_5$O$_4$ 0.3H$_2$O 0.1 ether. Requires C, 67.31; H, 6.80; N, 12.91%

The starting material was prepared as follows:

6-methoxy-4-[(3-methyl-1H-indol-5-yl)oxy]-7-[(piperidin-4-yl)methoxy]quinazoline (0.4 g), prepared as described for the starting material in Example 1, was dissolved in dichloromethane (15 ml). PS-DIEA resin (0.6 g; 4 mmol/g) was added followed by chloroacetyl chloride (0.091 ml). The reaction mixture was stirred at ambient temperature for 3 hours then diluted with methanol and the resin removed by filtration. The solvent was evaporated under vacuum and the residue was purified by column chromatography on silica using increasingly polar solvent mixtures, starting with dichloromethane and ending with dichloromethane/methanol (92/8). Removal of the solvents by evaporation gave 7-{[1-(chloroacetyl)piperidin-4-yl]methoxy}-6-methoxy-4-[(3-methyl-1H-indol-5-yl)oxy]quinazoline (0.237 g) as a solid foam.

Mass Spectrum: M+H$^+$495 and 497

$^1$H NMR Spectrum: (DMSOd$_6$) 1.20 (m, 1H), 1.40 (m, 1H), 1.85 (m, 2H), 2.20 (m, 1H), 2.25 (s, 3H), 2.75 (m, 1H), 3.15 (m, 1H), 3.90 (m, 1H), 4.0 (s, 3H), 4.10 (d, 2H), 4.40 (m, 3H), 6.95 (d, 1H), 7.20 (s, 1H), 7.40 (m, 2H), 7.60 (s, 1H), 8.50 (s, 1H)

EXAMPLE 5

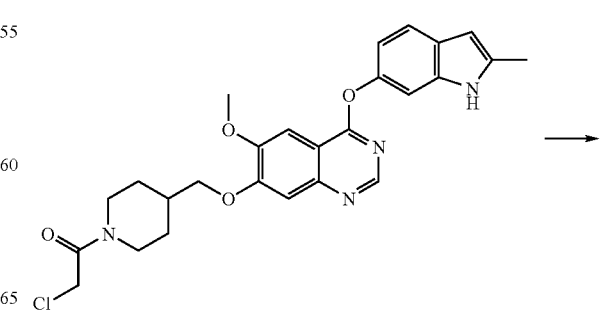

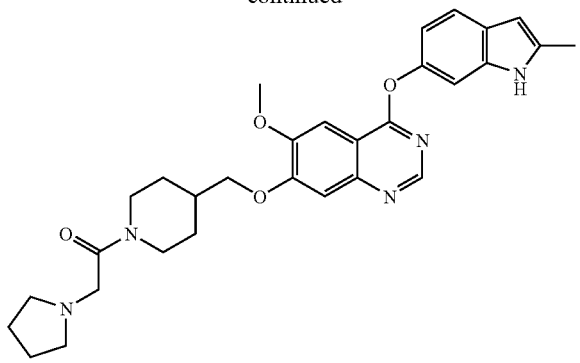

7-{[1-(Chloroacetyl)piperidin-4-yl]methoxy}-6-methoxy-4-[(2-methyl-1H-indol-6-yl)oxy]quinazoline (0.116 g) was reacted with pyrrolidine (0.059 ml) using an analogous procedure to that described in Example 4 to give, after work up and purification, 6-methoxy-4-[(2-methyl-1H-indol-6-yl)oxy]-7-{[1-(pyrrolidin-1-ylacetyl)piperidin-4-yl]methoxy}quinazoline (0.087 g) as a solid.

Mass Spectrum: M+H$^+$530

$^1$H NMR Spectrum: (DMSOd$_6$ and CF$_3$CO$_2$D) 1.25 (m, 1H), 1.40 (m, 1H), 1.90 (m, 4H), 2.05 (m, 2H), 2.25 (m, 1H), 2.40 (s, 3H), 2.80 (t, 1H), 3.05 (m, 2H), 3.15 (t, 1H), 3.6 (m, 2H), 3.70 (m, 1H), 4.05 (s, 3H), 4.15 (d, 2H), 4.35 (s, 1H), 4.45 (d, 2H), 6.20 (s, 1H), 6.90 (d, 1H), 7.20 (s, 1H), 7.50 (m, 2H), 7.75 (s, 1H), 8.90 (s, 1H)

Elemental Analysis: Found C, 66.64; H, 6.73; N, 12.98;

C$_{30}$H$_{35}$N$_5$O$_4$ 0.5H$_2$O 0.05 ether. Requires C, 66.88; H, 6.78; N, 12.91%

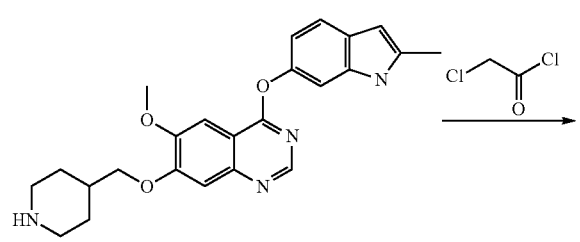

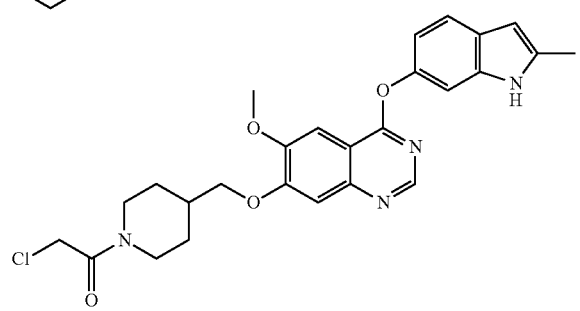

The starting material was prepared using analogous procedures to those described in Examples 1 and 4 but replacing 5-hydroxy-3-methylindole with 6-hydroxy-2-methylindole, (Eur. J. Med. Chem. 1975, 10, 187). Thus 6-methoxy-4-[(2-methyl-1H-indol-6-yl)oxy]-7-[(piperidin-4-yl)methoxy]quinazoline (0.4 g) gave 7-{[1-(chloroacetyl)piperidin-4-yl]methoxy}-6-methoxy-4-[(2-methyl-1H-indol-6-yl)oxy]quinazoline (0.233 g).

Mass Spectrum: M+H$^+$495 and 497

$^1$H NMR Spectrum: (DMSOd$_6$) 1.20 (m, 1H), 1.40 (m, 1H), 1.85 (m, 2H), 2.20 (m, 1H), 2.40 (s, 3H), 2.70 (m, 1H), 3.15 (m, 1H), 3.90 (m, 1H), 4.0 (s, 3H), 4.10 (d, 2H), 4.40 (m, 3H), 6.15 (s, 1H), 6.80 (d, 1H), 7.15 (s, 1H), 7.40 (s, 1H), 7.45 (d, 1H), 7.60 (s, 1H), 8.50 (s, 1H)

EXAMPLE 6

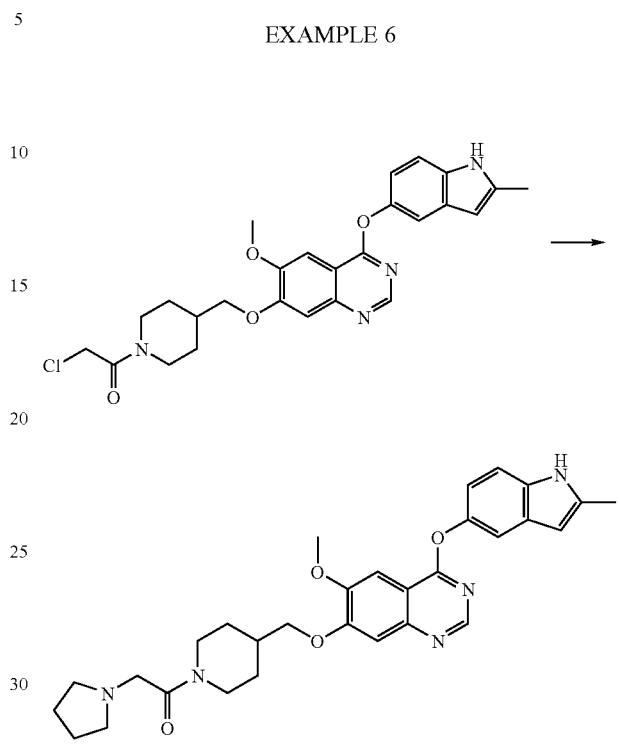

7-{[1-(Chloroacetyl)piperidin-4-yl]methoxy}-6-methoxy-4-[(2-methyl-1H-indol-5-yl)oxy]quinazoline (0.157 g) was reacted with pyrrolidine (0.077 ml) using an analogous procedure to that described in Example 4 to give, after work up and purification, 6-methoxy-4-[(2-methyl-1H-indol-5-yl)oxy]-7-{[1-(pyrrolidin-1-ylacetyl)piperidin-4-yl]methoxy}quinazoline (0.130 g) as a solid.

Mass Spectrum: M+H$^+$530

$^1$H NMR Spectrum: (DMSOd$_6$ and CF$_3$CO$_2$D) 1.25 (m, 1H), 1.40 (m, 1H), 1.90 (m, 4H), 2.0 (m, 2H), 2.25 (m, 1H), 2.45 (s, 3H), 2.80 (t, 1H), 3.10 (m, 2H), 3.15 (t, 1H), 3.6 (m, 2H), 3.70 (m, 1H), 4.05 (s, 3H), 4.20 (d, 2H), 4.35 (s, 1H), 4.45 (d, 2H), 6.20 (s, 1H), 6.95 (d, 1H), 7.30 (d, 1H), 7.35 (d, 1H), 7.50 (s, 1H), 7.75 (s, 1H), 8.90 (s, 1H)

Elemental Analysis Found C, 65.38; H, 6.62; N, 13.56;

C$_{30}$H$_{35}$N$_5$O$_4$ 0.7H$_2$O 0.4 DMF. Requires C, 65.57; H, 6.91; N, 13.23%

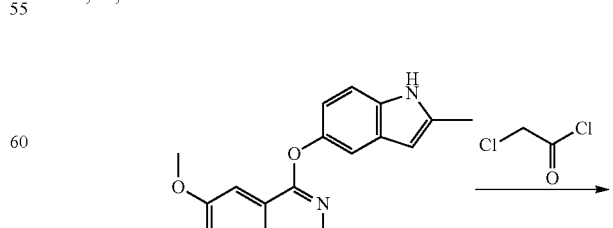

-continued

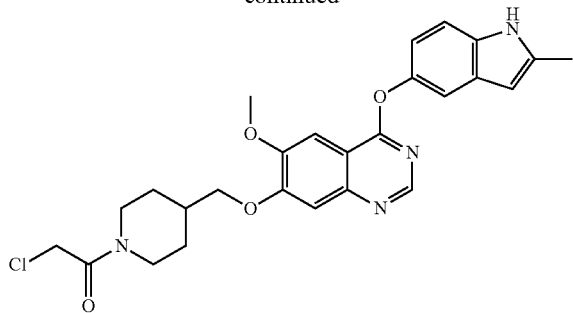

The starting material was prepared using analogous procedures to those described in Examples 1 and 4 but replacing 5-hydroxy-3-methylindole with 5-hydroxy-2-methylindole. Thus 6-methoxy-4-[(2-methyl-1H-indol-5-yl)oxy]-7-[(piperidin-4-yl)methoxy]quinazoline (0.42 g) gave 7-{[1-(chloroacetyl)piperidin-4-yl]methoxy}-6-methoxy-4-[(2-methyl-1H-indol-5-yl)oxy]quinazoline (0.315 g).

$^1$H NMR Spectrum: (DMSOd$_6$) 1.20 (m, 1H), 1.40 (m, 1H), 1.85 (m, 2H), 2.20 (m, 1H), 2.40 (s, 3H), 2.70 (m, 1H), 3.15 (m, 1H), 3.90 (m, 1H), 4.0 (s, 3H), 4.1 (d, 2H), 4.40 (m, 3H), 6.15 (s, 1H), 6.90 (d, 1H), 7.25 (s, 1H), 7.30 (d, 1H), 7.40 (s, 1H), 7.60 (s, 1H), 8.50 (s, 1H)

EXAMPLE 7

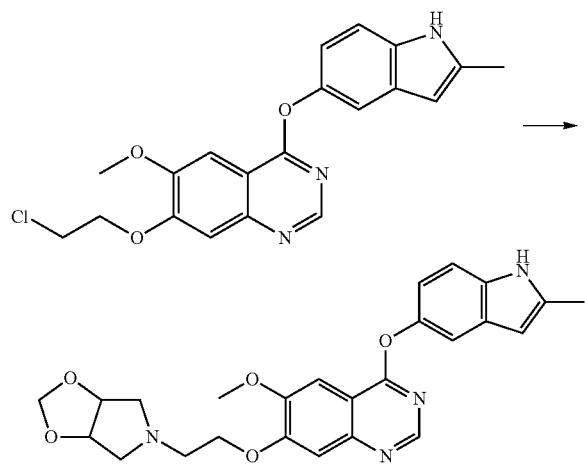

A mixture of 7-(2-chloroethoxy)-6-methoxy-4-[(2-methyl-1H-indol-5-yl)oxy]quinazoline (0.15 g), tetrahydro-3aH-[1,3]dioxolo[4,5-c]pyrrole hydrochloride (0.10 g), potassium carbonate (0.09 g) and potassium iodide (0.1 g) in DMA (1.5 ml) was stirred and heated at 80° C. for 12 hours. The mixture was diluted in DMF (0.8 ml), filtrated and purified by preparative LCMS (Hypersil C18-13-Basic column using a solvent gradient consisting of acetonitrile and water buffered with a 5% ammonium carbonate solution (100 g/L, pH 8.9). The solvent was removed by evaporation under vacuum and the residue was triturated under diethyl ether, filtered and dried to give 6-methoxy-4-[(2-methyl-1H-indol-5-yl)oxy]-7-[2-(tetrahydro-5H-[1,3]dioxolo[4,5-c]pyrrol-5-yl)ethoxy]quinazoline (0.10 g) as a pale yellow solid.

Mass Spectrum: M+H$^+$463

$^1$H NMR Spectrum: (DMSOd$_6$) 2.30 (d, 2H), 2.40 (s, 3H), 2.80 (t, 2H), 3.15 (d, 2H), 4.00 (s, 3H), 4.30 (t, 2H), 4.60 (s, 2H), 4.80 (s, 1H), 4.95 (s, 1H), 6.15 (s, 1H), 6.90 (d, 1H), 7.25 (s, 1H), 7.30 (d, 1H), 7.40 (s, 1H), 7.60 (s, 1H), 8.50 (s, 1H)

Elemental Analysis Found C, 62.51; H, 5.64; N, 11.63; C$_{25}$H$_{26}$N$_4$O$_5$. Requires C, 62.53; H, 5.99; N, 11.48%

The starting material was prepared as follows:

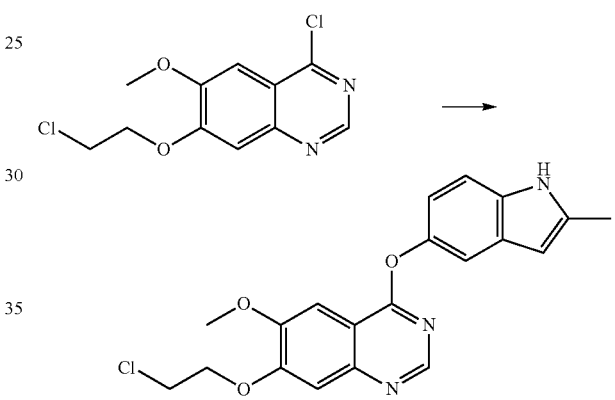

4-Chloro-7-(2-chloroethoxy)-6-methoxyquinazoline (4.0 g) was reacted with 5-hydroxy-2-methylindole (2.8 g) and potassium carbonate (3.3 g) using a procedure analogous to that described in Example 1 to give, after work up and purification, 7-(2-chloroethoxy)-6-methoxy-4-[(2-methyl-1H-indol-5-yl)oxy]quinazoline (4.8 g) as a beige solid.

Mass Spectrum: M+H$^+$384 and 386

$^1$H NMR Spectrum: (DMSOd$_6$) 2.40 (s, 3H), 4.00 (s, 3H), 4.05 (t, 2H), 4.50 (t, 2H), 6.15 (s, 1H), 7.00 (d, 1H), 7.25 (s, 1H), 7.30 (d, 1H), 7.40 (s, 1H), 7.60 (s, 1H), 8.50 (s, 1H)

The 4-chloro-7-(2-chloroethoxy)-6-methoxyquinazoline was prepared as follows:

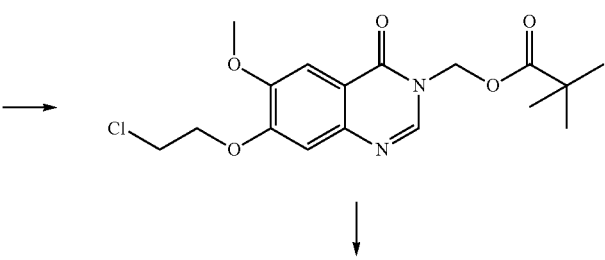

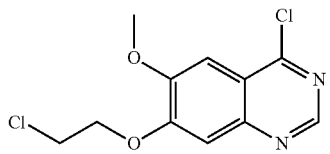 ← 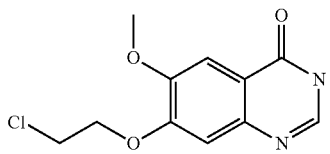

A mixture of 2-amino-4-benzyloxy-5-methoxybenzamide (10 g, 40 mmol), (J. Med. Chem. 1977, vol 20, 146-149), and Gold's reagent (7.4 g, 50 mmol) in dioxane (100 mL) was stirred and heated at reflux for 24 hours. Sodium acetate (3.02 g, 37 mmol) and acetic acid (1.65 mL, 29 mmol) were added to the reaction mixture and it was heated for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

Sodium hydride (1.44 g of a 60% suspension in mineral oil, 36 mmol) was added in portions over 20 minutes to a solution of 7-benzyloxy-6-methoxy-3,4-dihydroquinazolin-4-one (8.46 g, 30 mmol), in DMF (70 mL) and the mixture was stirred for 1.5 hours. Chloromethyl pivalate (5.65 g, 37.5 mmol) was added dropwise and the mixture stirred for 2 hours at ambient temperature. The mixture was diluted with ethyl acetate (100 mL) and poured onto ice/water (400 mL) and 2M hydrochloric acid (4 mL). The organic layer was separated and the aqueous layer extracted with ethyl acetate, the combined extracts were washed with brine, dried over magnesium sulphate and the solvent removed by evaporation. The residue was triturated with a mixture of ether and petroleum ether, the solid was collected by filtration and dried under vacuum to give 7-benzyloxy-6-methoxy-3-((pivaloyloxy)methyl)-3,4-dihydroquinazolin-4-one (10 g, 84%).

$^1$H NMR Spectrum: (DMSOd$_6$) 1.11 (s, 9H), 3.89 (s, 3H), 5.3 (s, 2H), 5.9 (s, 2H), 7.27 (s, 1H), 7.35 (m, 1H), 7.47 (t, 2H), 7.49 (d, 2H), 7.51 (s, 1H), 8.34 (s, 1H)

A mixture of 7-benzyloxy-6-methoxy-3-((pivaloyloxy)methyl)-3,4-dihydroquinazolin-4-one (7 g, 17.7 mmol) and 10% palladium-on-charcoal catalyst (700 mg) in ethyl acetate (250 mL), DMF (50 mL), methanol (50 mL) and acetic acid (0.7 mL) was stirred under hydrogen at atmospheric pressure for 40 minutes. The catalyst was removed by filtration and the solvent removed from the filtrate by evaporation. The residue was triturated with ether, collected by filtration and dried under vacuum to give 7-hydroxy-6-methoxy-3-((pivaloyloxy)methyl)-3,4-dihydroquinazolin-4-one (4.36 g, 80%).

$^1$H NMR Spectrum: (DMSOd$_6$) 1.1 (s, 9H), 3.89 (s, 3H), 5.89 (s, 2H), 7.0 (s, 1H), 7.48 (s, 1H), 8.5 (s, 1H)

7-Hydroxy-6-methoxy-3-((pivaloyloxy)methyl)-3,4-dihydroquinazolin-4-one (85 g, 270 mmol, several batches pooled together) was dissolved in DMF (400 mL), potassium carbonate (77 g, 550 mmol) and dichloroethane (400 mL, 5130 mmol) were added and the reaction mixture was stirred overnight at 70° C. The solid was removed by filtration and washed with DMF. The solvent was evaporated and the solid so obtained was washed with water and dried at 50° C. over P$_2$O$_5$. The crude product was purified by flash chromatography using dichloromethane/ethyl acetate (85/15 up to 75/25). Evaporation of the solvent gave 7-(2-chloroethoxy)-6-methoxy-3-((pivaloyloxy)methyl)-3,4-dihydroquinazolin-4-one (65.6 g, 66%) as a white solid.

$^1$H NMR Spectrum: (CDCl$_3$) 1.2 (s, 9H), 3.9 (t, 2H), 4.0 (s, 3H), 4.4 (t, 2H), 5.95 (s, 2H), 7.1 (s, 1H), 7.7 (s, 1H), 8.2 (s, 1H)

Mass Spectrum: M+H$^+$369 and 371 7-(2-Chloroethoxy)-6-methoxy-3-((pivaloyloxy)methyl)-3,4-dihydroquinazolin-4-one (65 g) was suspended in methanol saturated with ammonia gas (1.6 L) and stirred at ambient temperature for 2 days. The solvent was concentrated to about one-fourth and the precipitate collected by filtration and washed with ether to give 7-(2-chloroethoxy)-6-methoxy-3,4-dihydroquinazolin-4-one (44g, 100%) as a white solid.

$^1$H NMR Spectrum: (DMSOd$_6$) 3.9 (s, 3H), 4.05 (t, 2H), 4.4 (t, 2H), 7.15 (s, 1H), 7.45 (s, 1H), 8.0 (s, 1H)

Mass Spectrum: M+H$^+$255 and 257

7-(2-Chloroethoxy)-6-methoxy-3,4-dihydroquinazolin-4-one (5 g, 19 mmol) was suspended in thionyl chloride (28 mL) and DMF (0.7 mL) was added. The mixture was heated at 80° C. for 1.5 hours under anhydrous conditions. The excess thionyl chloride was evaporated off and toluene was added to remove the last traces by azeotropic distillation (repeated twice). The solid was suspended in ice-water and the pH adjusted to 7.5 with sodium hydroxide 2N first then with a saturated sodium hydrogen carbonate solution. The solid was collected by filtration, washed with water, ether and dried over P$_2$O$_5$ under vacuum. The crude product was purified by flash chromatography using dichloromethane/acetonitrile (95/5 up to 90/10). Evaporation of the solvent gave 4-chloro-7-(2-chloroethoxy)-6-methoxyquinazoline (3.06 g, 59%).

$^1$H NMR Spectrum: (CDCl$_3$) 3.95 (t, 2H), 4.1 (s, 3H), 4.5 (t, 2H), 7.35 (s, 1H), 7.45 (s, 1H), 8.9 (s, 1H)

Mass Spectrum: M+H$^+$273 and 275

The tetrahydro-3aH-[1,3]dioxolo[4,5-c]pyrrole hydrochloride was made as follows:

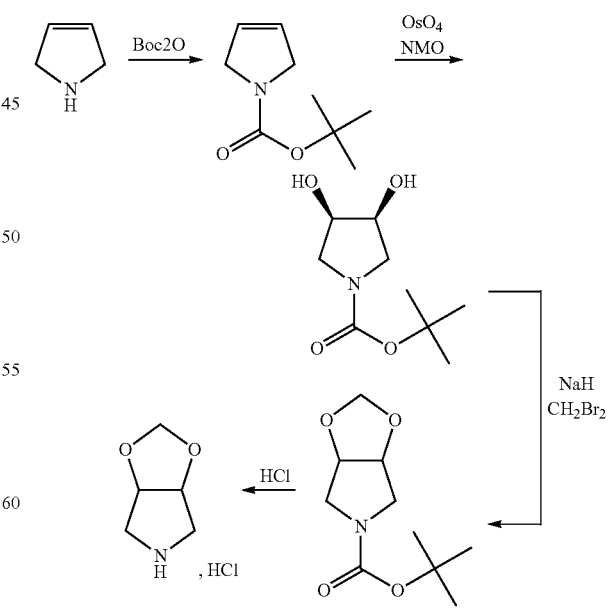

A mixture of 3-pyrroline (2,5-dihydro-1H-pyrrole) (25 g; 0.36 mole; 65% pure containing pyrrolidine) and ethyl acetate (125 mL) was cooled to 0° C. and a solution of Boc₂O (78.95 g; 0.36mol) in ethyl acetate (125 mL) was added dropwise while keeping the temperature between 5 and 10° C. The reaction mixture was then left to rise to ambient temperature overnight. The organic phase was washed successively with water, 25HCl 0.1N, water, saturated sodium hydrogen carbonate, brine and dried over magnesium sulphate. Filtration and evaporation of the solvent gave a colourless oil (62 g) containing 37% of pyrrolidine-Boc in addition to the desired tert-butyl 2,5-dihydro-1H-pyrrole-1-carboxylate (62 g, 100% based on conversion of both pyrroline and pyrrolidine).

¹H NMR Spectrum: (CDCl₃) 1.45 (s, 9H), 4.1 (d, 4H), 6.75 (m, 2H)

Pyrrolidone-Boc: 1.50 (s, 9H), 1.80 (br s, 4H), 3.3 (br s, 4H)

A solution of the crude tert-butyl 2,5-dihydro-1H-pyrrole-1-carboxylate mixture (57.5 g; 0.22 mol) in acetone (500 mL) was added dropwise to a mixture of N-methyl morpholine-N-oxide (28.45 g; 0.243 mol), osmium tetroxide (1.0 g; 0.004 mol) and water (500 mL) while keeping the temperature below 25° C. The reaction mixture was then stirred for 5 hours at ambient temperature. Acetone was evaporated off and the organic phase extracted with ethyl acetate. The combined organic phases were washed in turn with water and brine and dried over magnesium sulphate. The solvent was evaporated under vacuum and the residue was purified by column chromatography on silica using increasingly polar solvent mixtures, starting with ethyl acetate/petroleum ether (1/1) and ending with pure ethyl acetate. A second flash chromatography using increasingly polar solvent mixtures, starting with methanol/dichloromethane (2/98) and ending with methanol/dichloromethane (5/95) was done. Evaporation of the solvent gave tert-butyl (3R,4S)-3,4-dihydroxypyrrolidine-1-carboxylate (34.6 g; 77%) as a brown oil.

¹H NMR Spectrum: (CDCl₃) 1.45 (s, 9H), 2.65 (m, 2H), 3.35 (m, 2H), 3.6 (m, 2H), 4.25 (m, 2H)

tert-Butyl (3R,4S)-3,4-dihydroxypyrrolidine-1-carboxylate (34.6 g; 0.17 mol) was dissolved in DMF (400 mL) under argon and cooled down to 0-5° C. Sodium hydride (15 g; 0.375 mol) was added portionwise. The reaction mixture formed a foam which was difficult to stir. After 1 hour at 5° C., dibromomethane (15.6 mL; 0.22 mol) was added. After an additional 30 minutes at the same temperature, the reaction mixture was left to rise to ambient temperature. The temperature rose to 35° C. and was stirred overnight. The DMF was evaporated off and the residue partitioned between ethyl acetate and water. The water phase was extracted with ethyl acetate, the organic phases were combined and washed with water, brine, dried over magnesium sulphate and evaporated. The residue was dissolved in a minimum of dichloromethane and purified by flash chromatography using ethyl acetate/petroleum ether (3/7). Evaporation of the solvent gave tert-butyl tetrahydro-5H-[1,3]dioxolo[4,5-c]pyrrole-5-carboxylate (19.77 g; 54%) as a colorless oil.

¹H NMR Spectrum: (CDCl₃) 1.45 (s, 9H), 3.35 (m, 2H), 3.75 (br s, 2H), 4.65 (m, 2H), 4.9 (s, 1H), 5.1 (s, 1H)

tert-Butyl tetrahydro-5H-[1,3]dioxolo[4,5-c]pyrrole-5-carboxylate (19.77 g) was dissolved in dichloromethane (500 mL) and cooled in an ice bath. Cold (from the fridge) HCl in isopropanol (150 mL; 5N) solution was added and the reaction mixture was stirred at ambient temperature for 4 hours. The solvents were evaporated off and the residue triturated under ether. The precipitate was collected by filtration, washed with ether and dried to give tetrahydro-3aH-[1,3]dioxolo[4,5-c]pyrrole hydrochloride (13.18 g; 95%) as a beige solid.

¹H NMR Spectrum: (DMSOd₆) 3.15 (m, 2H), 3.35 (m, 2H), 4.65 (s, 1H), 4.8 (m, 2H), 5.1 (s, 1H)

EXAMPLE 8

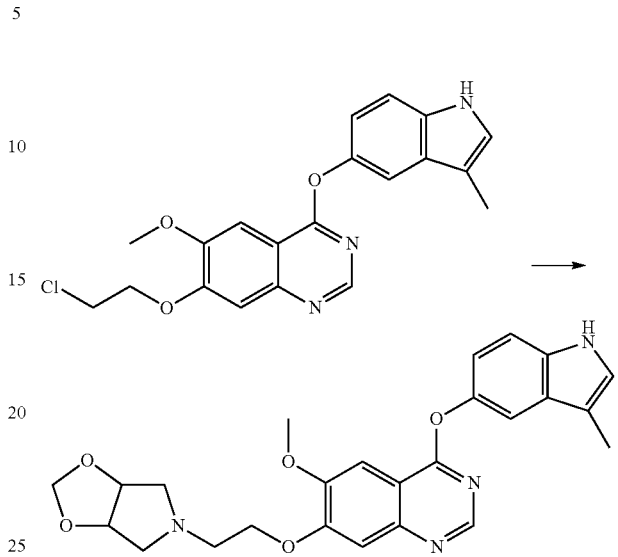

7-(2-Chloroethoxy)-6-methoxy-4-[(3-methyl-1H-indol-5-yl)oxy]quinazoline (0.15 g) was reacted with tetrahydro-3aH-[1,3]dioxolo[4,5-c]pyrrole hydrochloride, prepared as described in Example 7, (0.18 g), potassium carbonate (0.16 g) and potassium iodide (0.13 g) using an analogous procedure to that described in Example 7 to give, after work up and purification, 6-methoxy-4-[(3-methyl-1H-indol-5-yl)oxy]-7-[2-(tetrahydro-5H-[1,3]dioxolo[4,5-c]pyrrol-5-yl)ethoxy] quinazoline (0.07 g) as a pale yellow solid.

Mass Spectrum: M+H⁺463

¹H NMR Spectrum: (DMSOd₆) 2.25 (s, 3H), 2.30 (d, 2H), 2.80 (t, 2H), 3.15 (d, 2H), 4.00 (s, 3H), 4.30 (t, 2H), 4.55 (s, 2H), 4.80 (s, 1H), 4.95 (s, 1H), 6.95 (d, 1H), 7.20 (s, 1H), 7.35 (m, 3H), 7.60 (s, 1H), 8.50 (s, 1H)

Elemental Analysis Found C, 64.24; H, 5.89; N, 11.94; C₂₅H₂₆N₄O₅. Requires C, 64.30; H, 5.78; N, 11.90%

The starting material was prepared as follows:

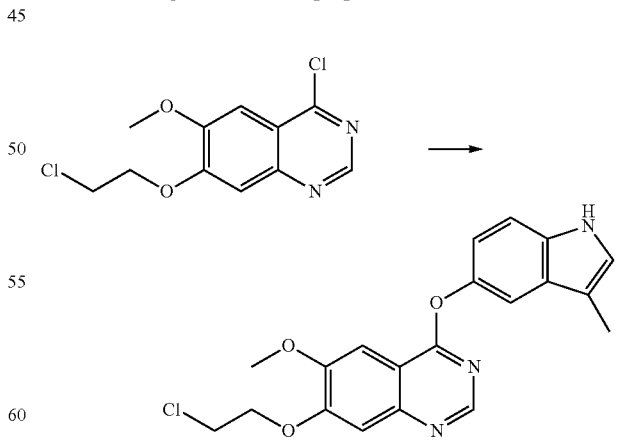

4-Chloro-7-(2-chloroethoxy)-6-methoxyquinazoline (1 g), prepared as described in Example 7, was reacted with 5-hydroxy-3-methylindole (0.65 g), (Journal of Organic Chemistry 1993, 58, 3757), and potassium carbonate (0.76 g) using an analogous procedure to that described in Example 1 to give, after work up and purification, 7-(2-chloroethoxy)-6-methoxy-4-[(3-methyl-1H-indol-5-yl)oxy]quinazoline (0.81 g) as a white solid.

Mass Spectrum: M+H⁺384 and 386

¹H NMR Spectrum: (DMSOd₆) 2.25 (s, 3H), 4.00 (s, 3H), 4.05 (t, 2H), 4.50 (t, 2H), 7.00 (d, 1H), 7.20 (s, 1H), 7.35 (s, 1H), 7.40 (d, 1H), 7.45 (s, 1H), 7.65 (s, 1H), 8.50 (s, 1H)

EXAMPLE 9

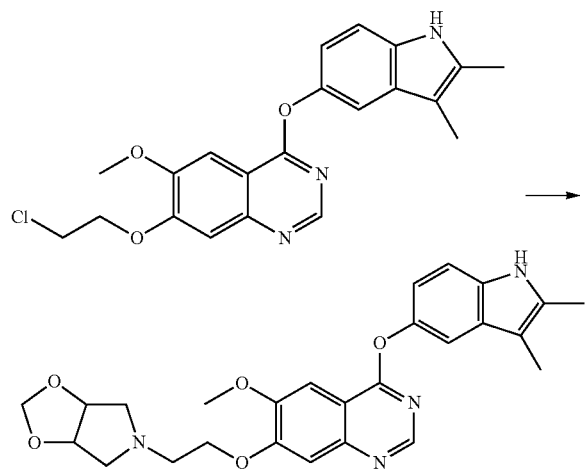

7-(2-Chloroethoxy)-4-[(2,3-dimethyl-1H-indol-5-yl)oxy]-6-methoxyquinazoline (0.15 g) was reacted with tetrahydro-3aH-[1,3]dioxolo[4,5-c]pyrrole hydrochloride, prepared as described in Example 7, (0.23 g), potassium carbonate (0.26 g) and potassium iodide (0.09 g) using an analogous procedure to that described in Example 7 to give, after work up and purification, 4-[(2,3-dimethyl-1H-indol-5-yl)oxy]-6-methoxy-7-[2-(tetrahydro-5H-[1,3]dioxolo[4,5-c]pyrrol-5-yl)ethoxy]quinazoline (0.03 g) as a pale yellow solid.

Mass Spectrum: M+H⁺477

¹H NMR Spectrum: (DMSOd₆) 2.10 (s, 3H), 2.25 (d, 2H), 2.35 (s, 3H), 2.80 (t, 2H), 3.15 (d, 2H), 4.00 (s, 3H), 4.30 (t, 2H), 4.55 (s, 2H), 4.80 (s, 1H), 5.00 (s, 1H), 6.90 (d, 1H), 7.20 (s, 1H), 7.30 (d, 1H), 7.40 (s, 1H), 7.60 (s, 1H), 8.50 (s, 1H)

Elemental Analysis: Found C, 64.45; H, 6.12; N, 11.22; C₂₆H₂₈N₄O₅. Requires C, 64.63; H, 5.86; N, 11.55%

The starting material was prepared as follows:

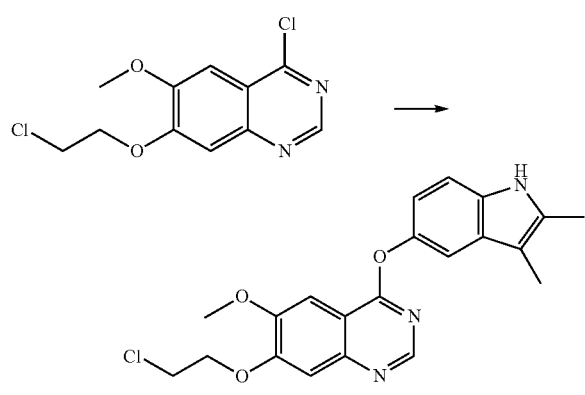

A mixture of 4-chloro-7-(2-chloroethoxy)-6-methoxyquinazoline (5.0 g), prepared as described in Example 7, 2,3-dimethyl-5-hydroxyindole (3.5 g), (Arch. Pharm. 1972, 305, 159), and potassium carbonate (4.0 g) in DMF (70 ml) was stirred and heated at 90° C. for 3 hours. The mixture was filtrated and the solvent was removed by evaporation under vacuum. The residue was purified by column chromatography on silica using the solvent mixture dichloromethane/ethyl acetate/methanol (50/48/2). The solvent was evaporated under vacuum to give 7-(2-chloroethoxy)-4-[(2,3-dimethyl-1H-indol-5-yl)oxy]-6-methoxyquinazoline (4.9 g) as a beige solid.

Mass Spectrum: M+H⁺398 and 400

¹H NMR Spectrum: (DMSOd₆) 2.15 (s, 3H), 2.35 (s, 3H), 4.00 (s, 3H), 4.10 (t, 2H), 4.50 (t, 2H), 6.85 (d, 1H), 7.20 (s, 1H), 7.25 (d, 1H), 7.40 (s, 1H), 7.60 (s, 1H), 8.50 (s, 1H)

EXAMPLE 10

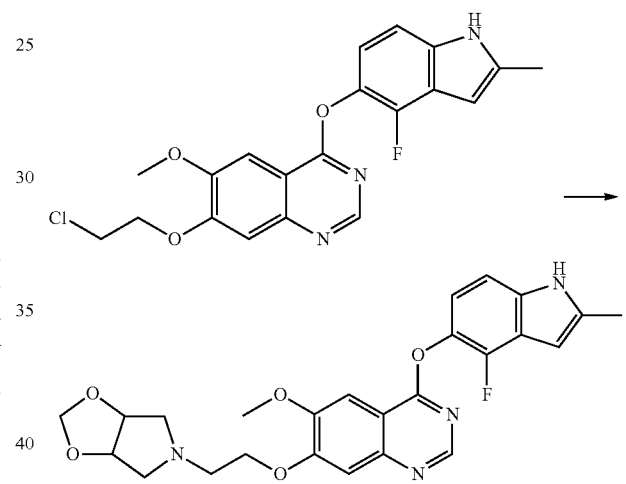

7-(2-Chloroethoxy)-4-[(4-fluoro-2-methyl-1H-indol-5-yl)oxy]-6-methoxyquinazoline (0.15 g) was reacted with tetrahydro-3aH-[1,3]dioxolo[4,5-c]pyrrole hydrochloride, prepared as described in Example 7, (0.10 g) using an analogous procedure to that described in Example 7 to give, after work up and purification, 4-[(4-fluoro-2-methyl-1H-indol-5-yl)oxy]-6-methoxy-7-[2-(tetrahydro-5H-[1,3]dioxolo[4,5-c]pyrrol-5-yl)ethoxy]quinazoline (0.09 g) as a beige solid.

Mass Spectrum: M+H⁺481

¹H NMR Spectrum: (DMSOd₆) 2.30 (d, 2H), 2.40 (s, 3H), 2.80 (t, 2H), 3.15 (d, 2H), 4.00 (s, 3H), 4.30 (t, 2H), 4.55 (s, 2H), 4.80 (s, 1H), 4.95 (s, 1H), 6.25 (s, 1H), 7.00 (t, 1H), 7.15 (d, 1H), 7.45 (s, 1H), 7.60 (s, 1H), 8.50 (s, 1H)

The starting material was prepared as follows:

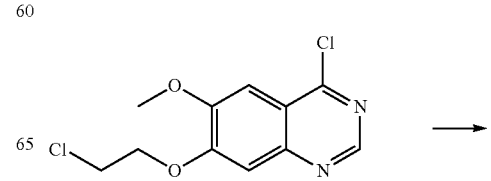

-continued

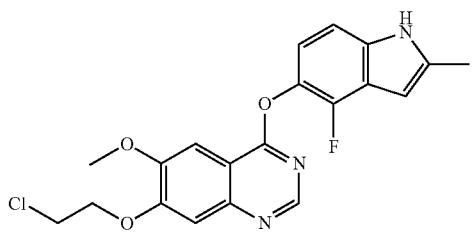

A mixture of 4-chloro-7-(2-chloroethoxy)-6-methoxyquinazoline (4.0 g), prepared as described in Example 7, was reacted with 4-fluoro-5-hydroxy-2-methylindole (3.1 g), prepared by any of the methods described in WO 00/47212, see in particular Example 237 therein, and potassium carbonate (3.3 g) using an analogous procedure to that described in Example 1 to give, after work up and purification, 7-(2-chloroethoxy)-4-[(4-fluoro-2-methyl-1H-indol-5-yl)oxy]-6-methoxyquinazoline (5.0 g) as a solid.

Mass Spectrum: M+H$^+$402 and 404

$^1$H NMR Spectrum: (DMSOd$_6$) 2.40 (s, 3H), 4.00 (s, 3H), 4.05 (t, 2H), 4.50 (t, 2H), 6.25 (s, 1H), 7.00 (t, 1H), 7.15 (d, 1H), 7.45 (s, 1H), 7.65 (s, 1H), 8.50 (s, 1H)

EXAMPLE 11

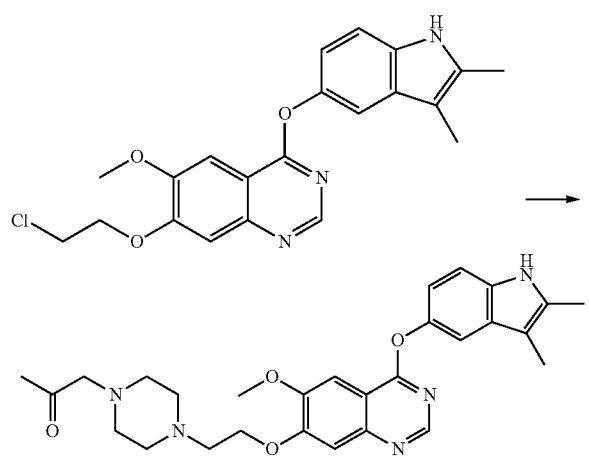

7-(2-Chloroethoxy)-4-[(2,3-dimethyl-1H-indol-5-yl)oxy]-6-methoxyquinazoline (0.14 g), prepared as described in Example 9, was reacted with 1-(acetylmethyl)piperazine (0.21 g), potassium carbonate (0.15 g) and potassium iodide (0.09 g) using an analogous procedure to that described in Example 7 to give, after work up and purification, 7-{2-[4-(acetylmethyl)piperazin-1-yl]ethoxy}-4-[(2,3-dimethyl-1H-indol-5-yl)oxy]-6-methoxyquinazoline (0.03 g) as a solid.

Mass Spectrum: M+H$^+$504

$^1$H NMR Spectrum: (DMSOd$_6$) 2.10 (s, 3H), 2.15 (s, 3H), 2.35 (s, 3H), 2.45 (m, 4H), 2.65 (m, 4H), 2.80 (t, 2H), 3.15 (s, 2H), 4.00 (s, 3H), 4.30 (t, 2H), 6.85 (d, 1H), 7.20 (s, 1H), 7.25 (d, 1H), 7.40 (s, 1H), 7.60 (s, 1H), 8.50 (s, 1H)

Elemental Analysis Found C, 64.86; H, 6.32; N, 13.80; C$_{28}$H$_{33}$N$_5$O$_4$. Requires C, 65.06; H, 6.49; N, 13.41%

The starting material was prepared as follows:

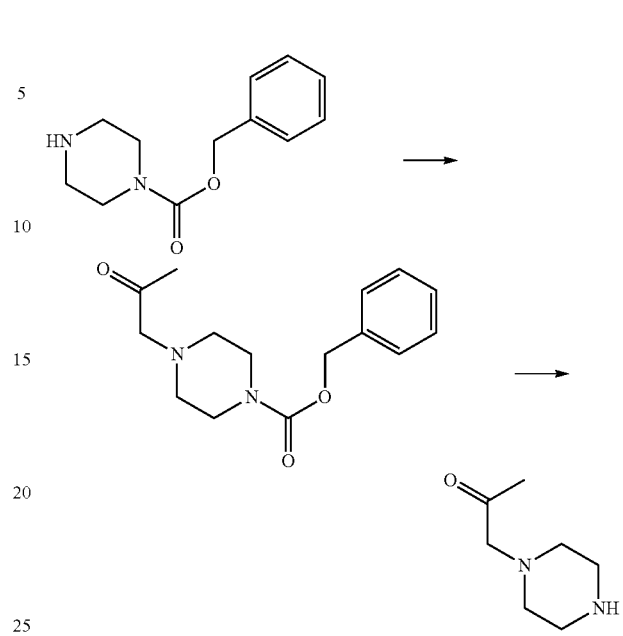

A mixture of benzyl 1-piperazinecarboxylate (4.1 ml), chloromethyl acetone (1.8 ml) and potassium carbonate (8.8 g) in acetonitrile (40 ml) was stirred overnight at ambient temperature. The reaction mixture was diluted in diethyl ether and the solution was partitioned between diethyl ether and water. The water phase was extracted with diethyl ether, the organic phases were combined and washed with water, brine, dried over magnesium sulphate and evaporated. The residue was purified by flash chromatography using dichloromethane/methanol saturated with ammonia (3.5 M) (98/2). Evaporation of the solvent gave benzyl 4-(acetylmethyl)-1-piperazinecarboxylate (3.7 g, 63%) as a yellow oil.

Mass Spectrum: M+H$^+$277

$^1$H NMR Spectrum: (DMSOd$_6$) 2.05 (s, 3H), 2.40 (m, 4H), 3.20 (s, 2H), 3.40 (m, 4H), 5.05 (s, 2H), 7.35 (m, 5H)

10% Palladium-on-charcoal catalyst (0.3 g) was added to a solution of benzyl 4-(acetylmethyl)-1-piperazinecarboxylate (3.7 g) in ethanol (45 ml). The reaction mixture was stirred under hydrogen at 3 atmospheres pressure for 1.5 hours. The catalyst was removed by filtration and the solvent removed from the filtrate by evaporation. The residue was purified by flash chromatography using dichloromethane/methanol saturated with ammonia (3.5 M) (97/3). Evaporation of the solvent gave 1-(acetylmethyl)piperazine (1.5 g, 80%) as a yellow oil.

$^1$H NMR Spectrum: (DMSOd$_6$) 2.07 (s, 3H), 2.35 (m, 4H), 2.65 (m, 4H), 3.10 (s, 2H)

EXAMPLE 12

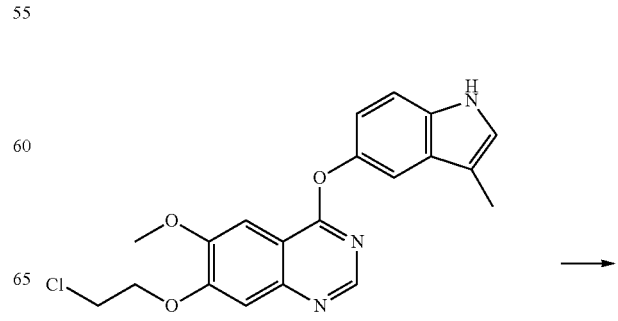

-continued

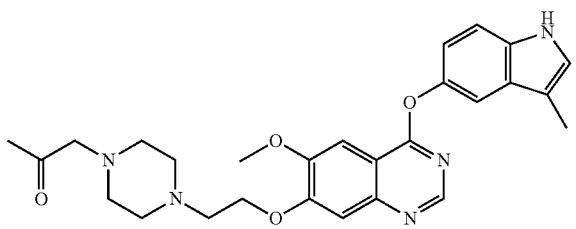

7-(2-Chloroethoxy)-6-methoxy-4-[(3-methyl-1H-indol-5-yl)oxy]quinazoline (0.15 g), prepared as described in Example 8, was reacted with 1-(acetylmethyl)piperazine (0.17 g) and potassium iodide (0.13 g) using an analogous procedure to that described in Example 7 to give, after work up and purification, 7-{2-[4-(acetylmethyl)piperazin-1-yl]ethoxy}-6-methoxy-4-[(3-methyl-1H-indol-5-yl)oxy]quinazoline (0.03 g) as a white solid.

Mass Spectrum: M+H$^+$490

$^1$H NMR Spectrum: (DMSOd$_6$) 2.10 (s, 3H), 2.25 (s, 3H), 2.45 (m, 4H), 2.55 (m, 4H), 2.80 (t, 2H), 3.15 (s, 2H), 4.00 (s, 3H), 4.30 (t, 2H), 6.95 (d, 1H), 7.20 (s, 1H), 7.35 (s, 1H), 7.40 (m, 2H), 7.60 (s, 1H), 8.50 (s, 1H)

Elemental Analysis Found C, 64.77; H, 6.64; N, 13.92; C$_{28}$H$_{33}$N$_5$O$_4$. Requires C, 64.96; H, 6.48; N, 13.98%

EXAMPLE 13

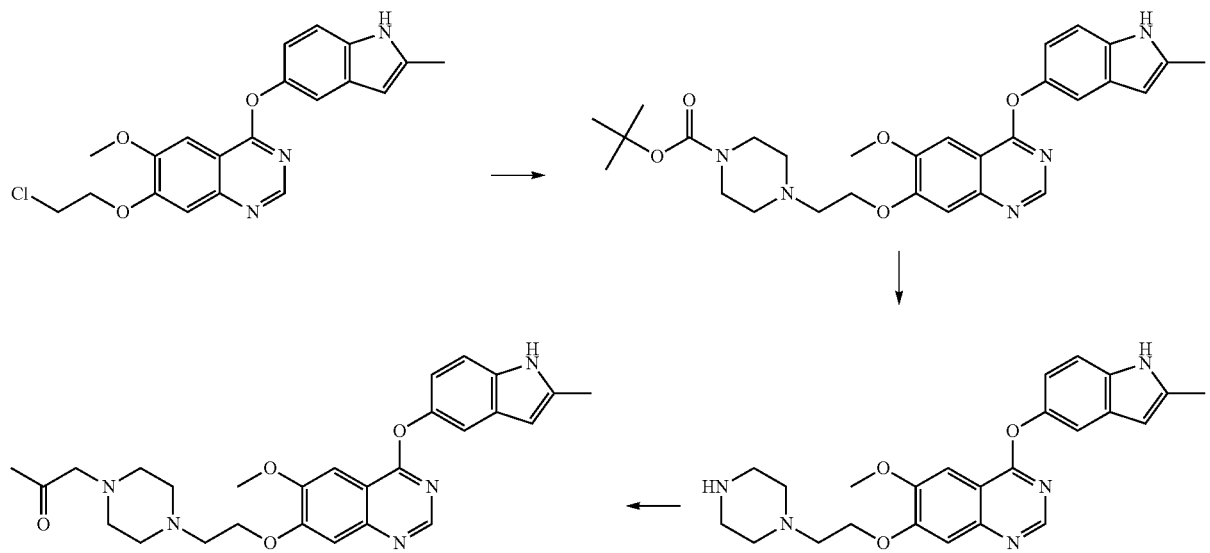

A mixture of 6-methoxy-4-[(2-methyl-1H-indol-5-yl)oxy]-7-[2-(piperazin-1-yl)ethoxy]quinazoline (0.15 g), chloroacetone (0.036 ml), potassium carbonate (0.05 g) and DMA (1.3 ml) was stirred and heated to 70° C. for 1.5 hours. The mixture was cooled to ambient temperature, the precipitate was filtered off and the residue was purified by preparative LCMS (Hypersil C18-β-Basic column using a solvent gradient consisting of acetonitrile and water buffered with a 5% ammonium carbonate solution (100 g/L, pH 8.9). Evaporation of the solvents gave 7-{2-[4-(acetylmethyl)piperazin-1-yl]ethoxy}-6-methoxy-4-[(2-methyl-1H-indol-5-yl)oxy]quinazoline as a pale yellow solid (0.10 g), which was dried under vacuum.

Mass Spectrum: M+H$^+$490

$^1$H NMR Spectrum: (DMSOd$_6$) 2.10 (s, 3H), 2.40 (s, 3H), 2.45 (m, 4H), 2.55 (m, 4H), 2.80 (t, 2H), 3.15 (s, 2H), 4.00 (s, 3H), 4.30 (t, 2H), 6.15 (s, 1H), 6.90 (d, 1H), 7.25 (s, 1H), 7.30 (d, 1H), 7.40 (s, 1H), 7.60 (s, 1H), 8.50 (s, 1H)

The starting material was prepared as follows:

7-(2-Chloroethoxy)-6-methoxy-4-[(2-methyl-1H-indol-5-yl)oxy]quinazoline (2.5 g), prepared as described in Example 7, was reacted with tert-butyl 1-piperazinecarboxylate (2.4 g), potassium iodide (1.6 g) and potassium carbonate (0.4 g) using an analogous procedure to that described in Example 7 to give, after work up and purification on silica (dichloromethane/ethyl acetate/methanol (50/48/2)), 7-{2-[4-(tert-butoxycarbonyl)piperazin-1-yl]ethoxy}-6-methoxy-4-[(2-methyl-1H-indol-5-yl)oxy]quinazoline (2.7 g) as a pale yellow solid.

Mass Spectrum: M+H$^+$534

$^1$H NMR Spectrum: (DMSOd$_6$) 1.40 (s, 9H), 2.40 (s, 3H), 2.50 (m, 4H), 2.80 (m, 2H), 3.35 (m, 4H), 4.00 (s, 3H), 4.30 (t, 2H), 6.15 (s, 1H), 6.85 (d, 1H), 7.25 (s, 1H), 7.30 (d, 1H), 7.40 (s, 1H), 7.60 (s, 1H), 8.50 (s, 1H)

TFA (8 ml) was added to a solution of 7-{2-[4-(tert-butoxycarbonyl)piperazin-1-yl]ethoxy}-6-methoxy-4-[(2-methyl-1H-indol-5-yl)oxy]quinazoline (2.75 g) in dichloromethane (30 ml) at 0° C. and the reaction mixture was stirred at this temperature for 1 hour before being concentrated in vacuum in a cold bath (~20° C.). Cold water was added to the residue and the pH was adjusted to 10.5 with 1N sodium hydroxide. After several extractions with dichloromethane, the combined organic layers were dried over magnesium sulphate, filtered and concentrated in vacuum to give 6-methoxy-4-[(2-methyl-1H-indol-5-yl)oxy]-7-[2-(piperazin-1-yl)ethoxy]quinazoline (1.8 g) as a white solid.

Mass Spectrum: M+H$^+$434

$^1$H NMR Spectrum: (DMSOd$_6$) 2.40 (s, 3H), 2.45 (m, 4H), 2.70 (m, 4H), 2.75 (t, 2H), 4.00 (s, 3H), 4.30 (t, 2H), 6.15 (s, 1H), 6.90 (d, 1H), 7.25 (s, 1H), 7.30 (d, 1H), 7.40 (s, 1H), 7.60 (s, 1H), 8.50 (s, 1H)

EXAMPLE 14

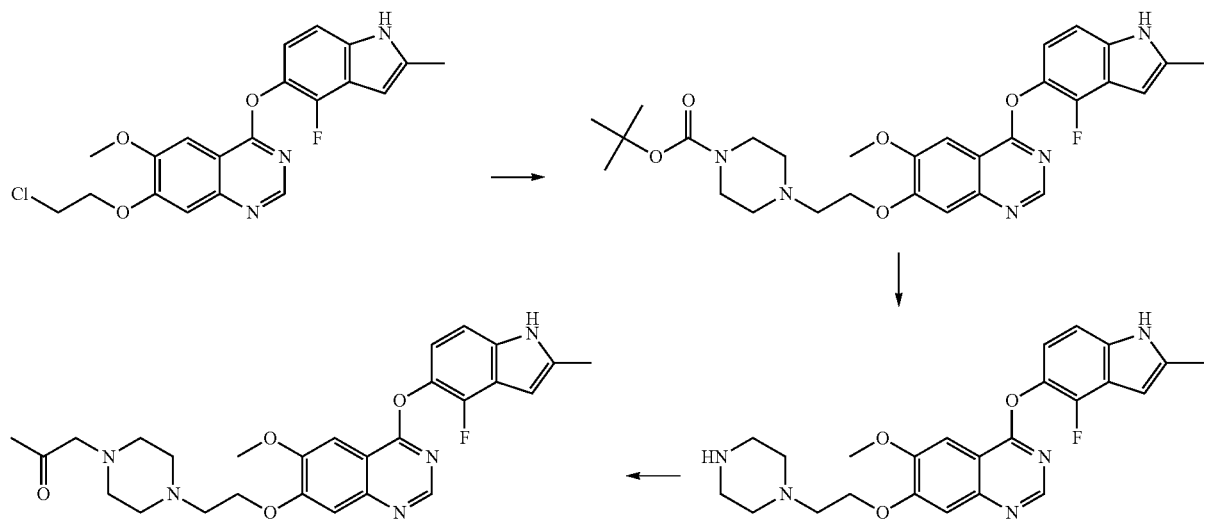

4-[(4-Fluoro-2-methyl-1H-indol-5-yl)oxy]-6-methoxy-7-[2-(piperazin-1-yl)ethoxy]quinazoline (0.15 g) was reacted with chloroacetone (0.034 ml) using an analogous procedure to that described in Example 13 to give, after work up and purification, 7-{2-[4-(acetylmethyl)piperazin-1-yl]ethoxy}-4-[(4-fluoro-2-methyl-1H-indol-5-yl)oxy]-6-methoxyquinazoline (0.10 g) as a beige solid.

Mass Spectrum: M+H+508

$^1$H NMR Spectrum: (DMSOd$_6$) 2.10 (s, 3H), 2.40 (s, 3H), 2.40 (m, 4H), 2.55 (m, 4H), 2.80 (t, 2H), 3.15 (s, 2H), 4.00 (s, 3H), 4.30 (t, 2H), 6.20 (s, 1H), 7.00 (t, 1H), 7.15 (d, 1H), 7.45 (s, 1H), 7.60 (s, 1H), 8.50 (s, 1H)

The starting material was prepared as follows:

7-(2-Chloroethoxy)-4-[(4-fluoro-2-methyl-1H-indol-5-yl)oxy]-6-methoxyquinazoline (2.5 g), prepared as described in Example 10, was reacted with tert-butyl 1-piperazinecarboxylate (2.3 g), potassium iodide (1.6 g) and potassium carbonate (0.4 g) using an analogous procedure to that described in Example 7 to give, after work up and purification, 7-{2-[4-(tert-butoxycarbonyl)piperazin-1-yl]ethoxy}-4-[(4-fluoro-2-methyl-1H-indol-5-yl)oxy]-6-methoxyquinazoline (3.0 g) as a solid.

Mass Spectrum: M+H+552

$^1$H NMR Spectrum: (DMSOd$_6$) 1.40 (s, 9H), 2.40 (s, 3H), 2.50 (m, 4H), 2.85 (t, 2H), 3.35 (m, 4H), 4.00 (s, 3H), 4.30 (t, 2H), 6.25 (s, 1H), 7.00 (t, 1H), 7.15 (d, 1H), 7.40 (s, 1H), 7.60 (s, 1H), 8.50 (s, 1H)

7-{2-[4-(tert-Butoxycarbonyl)piperazin-1-yl]ethoxy}-4-[(4-fluoro-2-methyl-1H-indol-5-yl)oxy]-6-methoxyquinazoline (3.0 g) was reacted with TFA (8.5 ml) using an analogous procedure to that described in Example 13 to give, after work up and purification 4-[(4-fluoro-2-methyl-1H-indol-5-yl)oxy]-6-methoxy-7-[2-(piperazin-1-yl)ethoxy]quinazoline (1.8 g) as a white solid.

Mass Spectrum: M+H+452

$^1$H NMR Spectrum: (DMSOd$_6$) 2.40 (s, 3H), 2.45 (m, 4H), 2.70 (m, 4H), 2.75 (t, 2H), 4.00 (s, 3H), 4.30 (t, 2H), 6.25 (s, 1H), 7.00 (t, 1H), 7.15 (d, 1H), 7.40 (s, 1H), 7.60 (s, 1H), 8.50 (s, 1H)

EXAMPLE 15

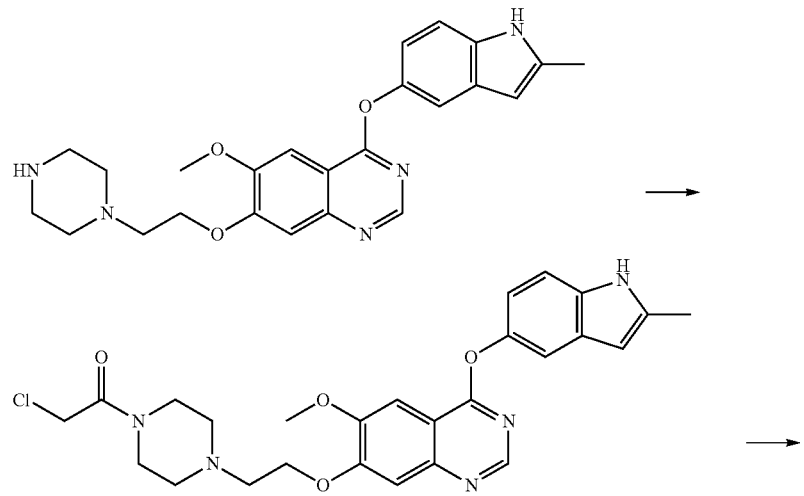

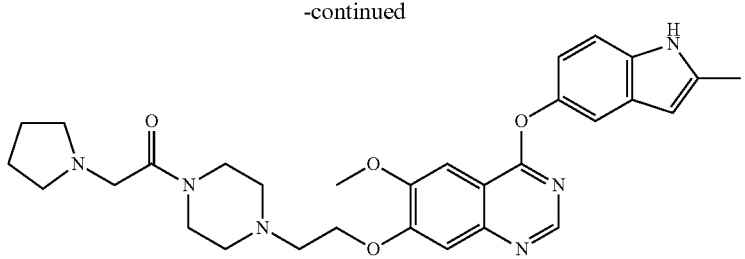

A mixture of 7-{2-[4-(chloroacetyl)piperazin-1-yl]ethoxy}-6-methoxy-4-[(2-methyl-1H-indol-5-yl)oxy]quinazoline (0.130 g), pyrrolidine (0.04 ml), potassium iodide (0.01 g) and DMF (3.5 ml) was stirred and heated to 80° C. for 1 hour. The mixture was cooled to ambient temperature, the solvent evaporated under vacuum and the residue was purified by column chromatography on silica using increasingly polar solvent mixtures, starting with dichloromethane and ending with dichloromethane/methanol saturated with ammonia (3.5M) (95/5). Evaporation of the solvents gave a foam, which was triturated under ether to give 6-methoxy-4-[(2-methyl-1H-indol-5-yl)oxy]-7-{2-[4-(pyrrolidin-1-ylacetyl)piperazin-1-yl]ethoxy}quinazoline (0.09 g) as a pale yellow solid which was collected by filtration and dried under vacuum.

Mass Spectrum: M+H$^+$545

$^1$H NMR Spectrum: (DMSOd$_6$) 1.70 (m, 4H), 2.40 (s, 3H), 2.50 (m, 8H), 2.80 (t, 2H), 3.25 (s, 2H), 3.45 (m, 2H), 3.55 (m, 2H), 4.00 (s, 3H), 4.30 (t, 2H), 6.15 (s, 1H), 6.90 (d, 1H), 7.25 (s, 1H), 7.30 (d, 1H), 7.40 (s, 1H), 7.60 (s, 1H), 8.50 (s, 1H)

The starting material was prepared as follows:

Chloroacetyl chloride (0.09 ml) was added dropwise to a solution of 6-methoxy-4-[(2-methyl-1H-indol-5-yl)oxy]-7-[2-(piperazin-1-yl)ethoxy]quinazoline (0.45 g), prepared as described in Example 13, and PS-DIEA resin (0.66 g) in dichloromethane (15 ml). After 1 hour at ambient temperature, methanol was added and the reaction mixture was filtered. Solvents were removed by evaporation in vacuum and the residue was triturated under diethyl ether, filtrated and dried to give 7-{2-[4-(chloroacetyl)piperazin-1-yl]ethoxy}-6-methoxy-4-[(2-methyl-1H-indol-5-yl)oxy]quinazoline (0.36 g) as a solid.

Mass Spectrum: M+H$^+$510 and 512

$^1$H NMR Spectrum: (DMSOd$_6$) 2.40 (s, 3H), 2.55 (m, 2H), 2.60 (m, 2H), 2.85 (t, 2H), 3.50 (m, 4H), 4.00 (s, 3H), 4.35 (t, 2H), 4.40 (s, 2H), 6.15 (s, 1H), 6.90 (d, 1H), 7.25 (s, 1H), 7.30 (d, 1H), 7.40 (s, 1H), 7.60 (s, 1H), 8.50 (s, 1H)

EXAMPLE 16

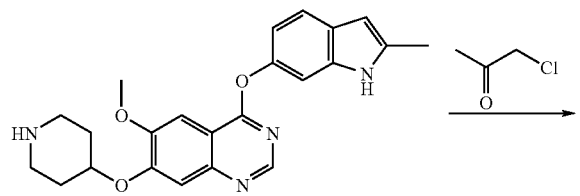

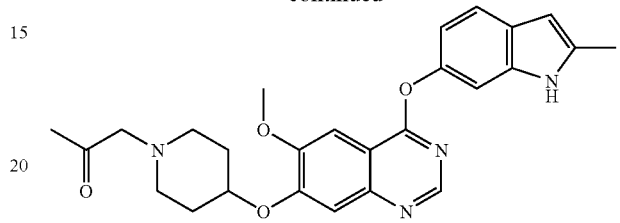

6-Methoxy-4-[(2-methyl-1H-indol-6-yl)oxy]-7-[(piperidin-4-yl)oxy]quinazoline (0.25 g) was reacted with chloroacetone (0.054 ml) using an analogous procedure to that described in Example 1 to give, after work up and purification, 7-{[1-(acetylmethyl)piperidin-4-yl]oxy}-6-methoxy-4-[(2-methyl-1H-indol-6-yl)oxy]quinazoline (0.21 g) as a white solid.

Mass Spectrum: M+H$^+$461

$^1$H NMR Spectrum: (DMSOd$_6$) 1.75 (m, 2H), 2.05 (m, 2H), 2.10 (s, 3H), 2.35 (m, 2H), 2.40 (s, 3H), 2.75 (m, 2H), 3.20 (s, 2H), 3.95 (s, 3H), 4.75 (s, 1H), 6.15 (s, 1H), 6.8 (d, 1H), 7.15 (s, 1H), 7.40 (m, 2H), 7.6 (s, 1H), 8.50 (s, 1H)

Elemental Analysis Found C, 67.74; H, 6.28; N, 11.66; $C_{26}H_{28}N_4O_4$ 0.1 ether. Requires C, 67.76; H, 6.25; N, 11.97%

The starting material was prepared as follows:

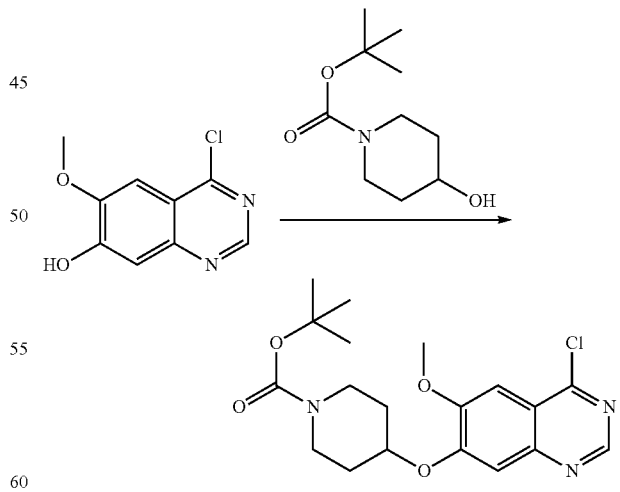

A suspension of 4-chloro-7-hydroxy-6-methoxyquinazoline (11.5 g), prepared as described in Example 1, in dichloromethane (250 ml) was treated with triphenylphosphine (21.5 g), 1-(tert-butoxycarbonyl)-4-hydroxypiperidine (13.2 g) and di-tert-butyl azodicarboxylate (19 g) and the mixture stirred at ambient temperature overnight. The crude reaction mixture was concentrated to a third and loaded onto a silica column and eluted using ethyl acetate/petroleum ether (35/65) as solvent. The relevant fractions were combined and evaporated under vacuum to give 7-{[1-(tert-butoxycarbonyl)-piperidin-4-yl]oxy}-4-chloro-6-methoxyquinazoline as a white solid (20 g).

¹H NMR Spectrum: (DMSOd₆) 1.40 (s, 9H), 1.60 (m, 2H), 2.05 (m, 2H), 3.2 (m, 2H), 3.70 (m, 2H), 4.0 (s, 3H), 4.95 (m, 1H), 7.40 (s, 1H), 7.60 (s, 1H), 8.90 (s, 1H)

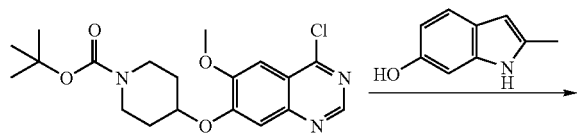

7-{[1-(tert-Butoxycarbonyl)-piperidin-4-yl]oxy}-4-chloro-6-methoxyquinazoline (5 g) was dissolved in DMF (100 ml). 6-Hydroxy-2-methylindole (2.3 g), (Eur. J. Med. Chem. 1975, 10, 187), and potassium carbonate (2.6 g), were added and the mixture heated at 90° C. for 3 hours. The solid was removed by filtration and the filtrate was concentrated to dryness under vacuum. The residue was purified by column chromatography on silica using increasingly polar solvent mixtures, starting with ethyl acetate/petroleum ether (1/1) and ending with (75/25). Evaporation of the solvents gave, 7-{[1-(tert-butoxycarbonyl)-piperidin-4-yl]oxy}-6-methoxy-4-[(2-methyl-1H-indol-6-yl)oxy]quinazoline (5.4 g) as a yellow foam.

¹H NMR Spectrum: (DMSOd₆) 1.40 (s, 9H), 1.60 (m, 2H), 2.05 (m, 2H), 2.30 (s, 3H), 3.20 (m, 2H), 3.70 (m, 2H), 4.0 (s, 3H), 4.90 (s, 1H), 6.20 (s, 1H), 6.85 (d, 1H), 7.15 (s, 1H), 7.40 (d, 1H), 7.50 (s, 1H), 7.60 (s, 1H), 8.50 (s, 1H)

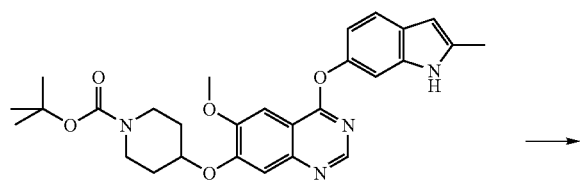

7-{[1-(tert-Butoxycarbonyl)-piperidin-4-yl]oxy}-6-methoxy-4-[(2-methyl-1H-indol-6-yl)oxy]quinazoline (1 g) was dissolved in dichloromethane (5 ml) and cooled in an ice bath. TFA (2.5 ml) was added and the reaction mixture stirred at this temperature for 35 minutes. The volatiles were removed by filtration and the residue taken up into ice cold water. The pH was adjusted to 12 with sodium hydroxide 2N and extracted twice with dichloromethane. The combined extracts were washed in turn with water and brine and dried over magnesium sulphate and the solvent evaporated under vacuum to give 6-methoxy-4-[(2-methyl-1H-indol-6-yl)oxy]-7-[(piperidin-4-yl)oxy]quinazoline (0.765 g) as a solid foam.

¹H NMR Spectrum: (DMSOd₆) 1.55 (m, 2H), 2.05 (m, 2H), 2.40 (s, 3H), 2.65 (m, 2H), 2.95 (m, 2H), 4.0 (s, 3H), 4.75 (m, 1H), 6.15 (s, 1H), 6.80 (d, 1H), 7.15 (s, 1H), 7.45 (m, 2H), 7.60 (s, 1H), 8.45 (s, 1H)

EXAMPLE 17

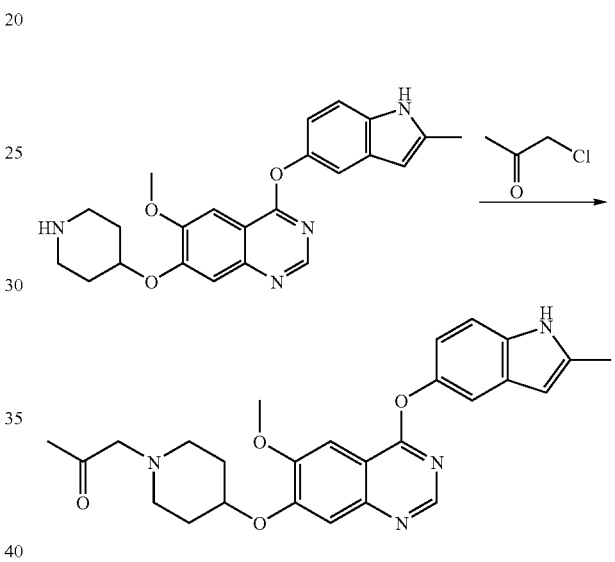

6-Methoxy-4-[(2-methyl-1H-indol-5-yl)oxy]-7-[(piperidin-4-yl)oxy]quinazoline (0.25 g) was reacted with chloroacetone (0.054 ml) using an analogous procedure to that described in Example 1 to give, after work up and purification, 7-{[1-(acetylmethyl)piperidin-4-yl]oxy}-6-methoxy-4-[(2-methyl-1H-indol-5-yl)oxy]quinazoline (0.216 g).

Mass Spectrum: M+H⁺461

¹H NMR Spectrum: (DMSOd₆) 1.75 (m, 2H), 2.05 (m, 2H), 2.10 (s, 3H), 2.35 (m, 2H), 2.40 (s, 3H), 2.75 (m, 2H), 3.20 (s, 2H), 3.95 (s, 3H), 4.70 (m, 1H), 6.15 (s, 1H), 6.90 (d, 1H), 7.25 (s, 1H), 7.30 (d, 1H), 7.40 (s, 1H), 7.60 (s, 1H), 8.50 (s, 1H)

Elemental Analysis Found C, 67.79; H, 5.99; N, 12.07; C₂₆H₂₈N₄O₄. Requires C, 67.81; H, 6.13; N, 12.17%

The starting material was prepared as follows:

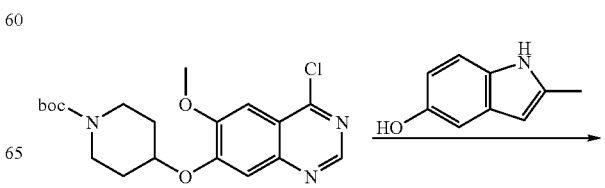

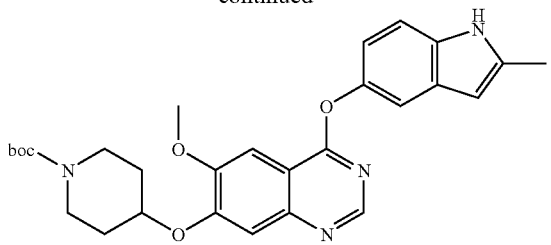

7-{[1-(tert-Butoxycarbonyl)-piperidin-4-yl]oxy}-4-chloro-6-methoxyquinazoline (5 g), prepared as described in Example 16, was reacted with 5-hydroxy-2-methylindole (2.3 g) using an analogous procedure to that described in Example 16 to give, after work up and purification, 7-{[1-(tert-butoxycarbonyl)-piperidin-4-yl]oxy}-6-methoxy-4-[(2-methyl-1H-indol-5-yl)oxy]quinazoline (2.3 g).

Mass Spectrum: M+H+505

¹H NMR Spectrum: (DMSOd₆) 1.40 (s, 9H), 1.60 (m, 2H), 2.05 (m, 2H), 2.40 (s, 3H), 3.20 (m, 2H), 3.75 (m, 2H), 4.0 (s, 3H), 4.90 (s, 1H), 6.15 (s, 1H), 6.85 (d, 1H), 7.25 (s, 1H), 7.30 (d, 1H), 7.50 (s, 1H), 7.60 (s, 1H), 8.50 (s, 1H)

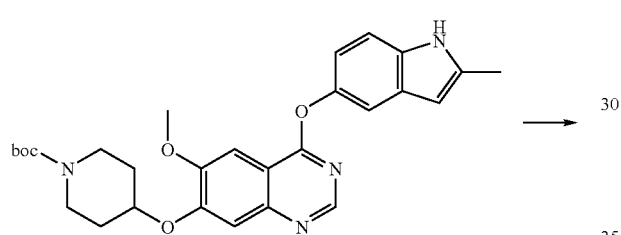

7-{[1-(tert-Butoxycarbonyl)-piperidin-4-yl]oxy}-6-methoxy-4-[(2-methyl-1H-indol-5-yl)oxy]quinazoline (2.3 g) was reacted with TFA (7 ml) using an analogous procedure to that described in Example 16 to give, after work up and purification, 6-methoxy-4-[(2-methyl-1H-indol-5-yl)oxy]-7-[(piperidin-4-yl)oxy]quinazoline (1.6 g).

Mass Spectrum: M+H+405

EXAMPLE 18

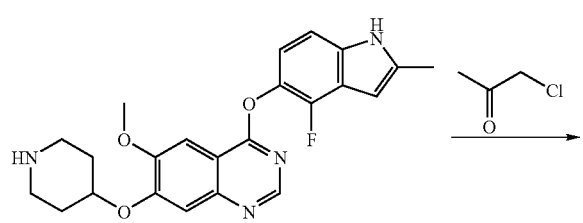

4-[(4-Fluoro-2-methyl-1H-indol-5-yl)oxy]-6-methoxy-7-[(piperidin-4-yl)oxy]quinazoline (0.18 g) was reacted with chloroacetone (0.038 ml) using an anaolgous procedure to that described in Example 1 to give, after work up and purification, 7-{[1-(acetylmethyl)piperidin-4-yl]oxy}-4-[(4-fluoro-2-methyl-1H-indol-5-yl)oxy]-6-methoxyquinazoline (0.14 g).

Mass Spectrum: M+H+479

¹H NMR Spectrum: (DMSOd₆) 1.75 (m, 2H), 2.05 (m, 2H), 2.10 (s, 3H), 2.35 (m, 2H), 3.40 (s, 3H), 2.70 (m, 2H), 3.20 (s, 3H), 4.0 (s, 3H), 4.70 (m, 1H), 6.20 (s, 1H), 6.95 (m, 1H), 7.15 (d, 1H), 7.45 (s, 1H), 7.60 (s, 1H), 8.50 (s, 1H)

Elemental Analysis Found C, 65.04; H, 5.55; N, 11.53; $C_{26}H_{27}N_4O_4F$. Requires C, 65.26; H, 5.69; N, 11.71%

The starting material was prepared as follows:

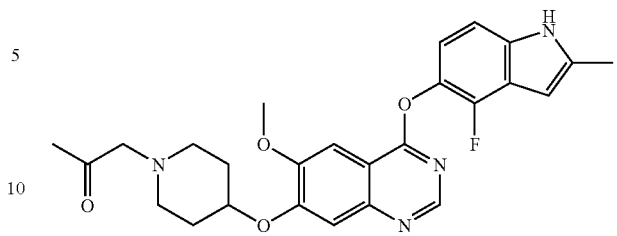

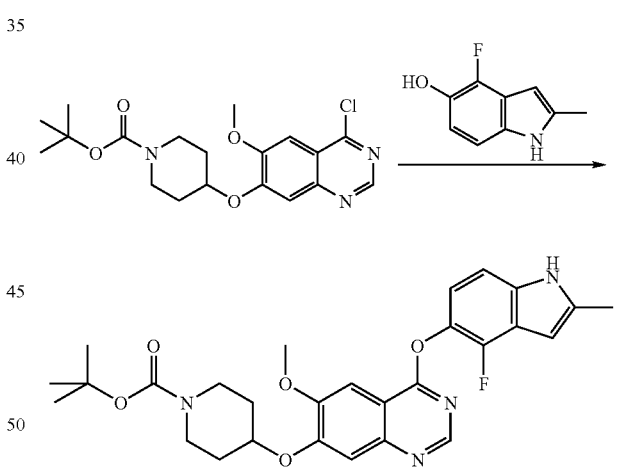

7-{[1-(tert-Butoxycarbonyl)-piperidin-4-yl]oxy}-4-chloro-6-methoxyquinazoline (3 g), prepared as described in Example 16, was reacted with 4-fluoro-5-hydroxy-2-methylindole (1.4 g), prepared by any of the methods described in WO 00/47212, see in particular Example 237 therein, using an analogous procedure to that described in Example 16 to give, after work up and purification, 7-{[1-(tert-butoxycarbonyl)-piperidin-4-yl]oxy}-4-[(4-fluoro-2-methyl-1H-indol-5-yl)oxy]-6-methoxyquinazoline (1.76 g).

¹H NMR Spectrum: (DMSOd₆) 1.40 (s, 9H), 1.60 (m, 2H), 2.05 (m, 2H), 2.40 (s, 3H), 3.20 (m, 2H), 3.70 (m, 2H), 4.0 (s, 3H), 4.90 (m, 1H), 6.25 (s, 1H), 6.95 (m, 1H), 7.15 (d, 1H), 7.55 (s, 1H), 7.65 (s, 1H), 8.50 (s, 1H)

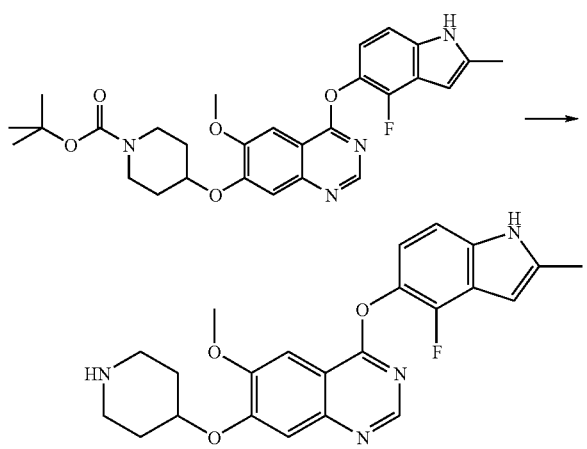

7-{[1-(tert-Butoxycarbonyl)-piperidin-4-yl]oxy}-4-[(4-fluoro-2-methyl-1H-indol-5-yl)oxy]-6-methoxyquinazoline (1.7 g) was reacted with TFA (5 ml) using an analogous procedure to that described in Example 16 to give, after work up and purification, 4-[(4-fluoro-2-methyl-1H-indol-5-yl)oxy]-6-methoxy-7-[(piperidin-4-yl)oxy]quinazoline (1.2 g).

Mass Spectrum: M+H$^+$423

EXAMPLE 19

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium stearate | 1.5 |
| (e) | Injection I | (50 mg/ml) |
| | Compound X | 5.0% w/v |
| | 1M Sodium hydroxide solution | 15.0% v/v |
| | 0.1M Hydrochloric acid | |
| | (to adjust pH to 7.6) | |
| | Polyethylene glycol 400 | 4.5% w/v |
| | Water for injection to 100% | |
| (f) | Injection II | 10 mg/ml |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note
The above formulations may be obtained by conventional procedures well known in the pharmaceutical art. The tablets (a)-(c) may be enteric coated by conventional means, for example to provide a coating of cellulose acetate phthalate.

The invention claimed is:
1. A compound of the formula IIb:

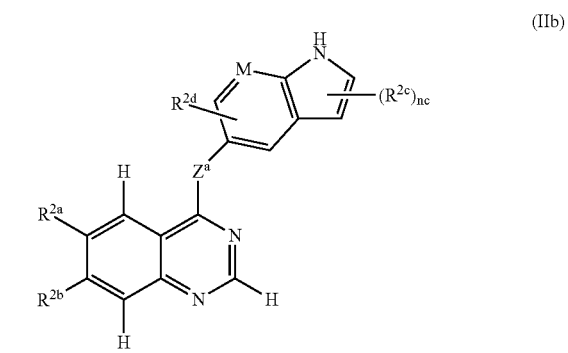

(IIb)

wherein:

M is —CH— or —N—;

nc is 0, 1 or 2;

$R^{2c}$ is linked to a carbon atom of the 5-membered ring and is selected from hydrogen and methyl;

$R^{2d}$ is linked to a carbon atom of the 6-membered ring and is selected from hydrogen and fluoro;

$R^{2a}$ and $R^{2b}$ are each independently selected from hydrogen, hydroxy, halogeno, cyano, nitro, trifluoromethyl, $C_{1-3}$alkyl, $C_{1-3}$alkoxy, $C_{1-3}$alkylsulphanyl, —NR$^{3a}$R$^{4a}$ (wherein R$^{3a}$ and R$^{4a}$, which may be the same or different, each represents hydrogen or $C_{1-3}$alkyl), and $Q^1X^1$— wherein $Q^1$ is selected from one of the following groups:

1) —$C_{1-4}$alkyl-$Q^{13}$-C(O)—$C_{1-4}$alkyl-$Q^{14}$ wherein $Q^{13}$ and $Q^{14}$ are each independently selected from pyrrolidinyl, piperidinyl, piperazinyl,

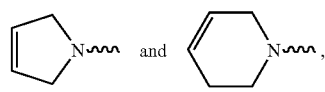

wherein $Q^{14}$ is linked to $C_{1-4}$alkanoyl through a nitrogen atom;

2) $Q^2$ (wherein $Q^2$ is a 5-6-membered heterocyclic group selected from pyrrolidinyl, piperidinyl, piperazinyl,

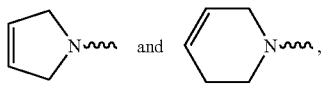

which heterocyclic group bears either one substituent selected from methylenedioxy or ethylenedioxy to form a bicyclic ring, or bears at least one substituent selected from $C_{2-4}$alkanoyl$C_{1-3}$alkyl and optionally bears a further 1 or 2 substituents selected from $C_{2-5}$alkenyl, $C_{2-5}$alkynyl, $C_{1-6}$fluoroalkyl, $C_{1-6}$alkanoyl, $C_{2-4}$alkanoyl$C_{1-3}$alkyl, amino$C_{1-6}$alkanoyl, $C_{1-4}$alkylamino$C_{1-6}$alkanoyl, di($C_{1-4}$alkyl)amino$C_{1-6}$alkanoyl, $C_{1-6}$-fluoroalkanoyl, carbamoyl, $C_{1-4}$alkylcarbamoyl, di($C_{1-4}$alkyl)carbamoyl, carbamoyl$C_{1-6}$alkyl, $C_{1-4}$alkylcarbamoyl$C_{1-6}$alkyl, di($C_{1-4}$alkyl)carbamoyl$C_{1-6}$alkyl, $C_{1-6}$alkylsulphonyl, $C_{1-6}$fluoroalkylsulphonyl, oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$ alkoxy and a group —(—O—)$_f$($C_{1-4}$alkyl)$_g$ ringD (wherein f is 0 or 1, g is 0 or 1 and ring D is a 5-6-membered saturated or partially unsaturated heterocyclic group with 1-2 heteroatoms, selected independently from O, S and N, which cyclic group may bear one or more substituents selected from $C_{1-4}$alkyl)); and 3) —$C_{1-5}$alkyl$Q^2$ (wherein $Q^2$ is as defined herein); and $X^1$ is O;

and additionally wherein any $C_{1-5}$alkyl group in $Q^1X^1$— which is linked to $X^1$ may bear one or more substituents selected from hydroxy, halogeno and amino;

Za is —O— or —S—;

with the proviso that at least one of $R^{2a}$ and $R^{2b}$ is $Q^1X^1$— wherein $Q^1$ and $X^1$ are as defined herein;

or a pharmaceutically-acceptable salt thereof.

2. The compound according to claim 1 wherein one of $R^{2a}$ and $R^{2b}$ is methoxy and the other is $Q^1X^1$— wherein $X^1$ and $Q^1$ are as defined in claim 1.

3. The compound according to claim 1 wherein one of $R^{2a}$ and $R^{2b}$ is methoxy and the other is $Q^1X^1$— wherein $X^1$ is —O— and $Q^1$ is —$C_{1-4}$alkyl-$Q^{13}$-C(O)—$C_{1-4}$alkyl-$Q^{14}$ wherein $Q^{13}$ and $Q^{14}$ are each independently selected from pyrrolidinyl, piperidinyl, piperazinyl,

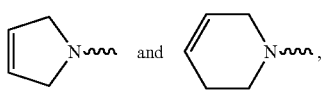

wherein $Q^{14}$ is linked to —$C_{1-4}$alkanoyl through a nitrogen atom.

4. The compound according to claim 1 wherein one of $R^{2a}$ and $R^{2b}$ is methoxy and the other is $Q^1X^1$— wherein $X^1$ is —O— and $Q^1$ is selected from one of the following groups:

1) $Q^2$ (wherein $Q^2$ is a 5-6-membered heterocyclic group selected from pyrrolidinyl, piperidinyl, piperazinyl,

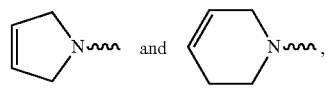

which heterocyclic group bears either one substituent selected from methylenedioxy or ethylenedioxy to form a bicyclic ring, or bears one substituent selected from $C_{2-4}$alkanoyl$C_{1-3}$alkyl; and 2) —$C_{1-5}$alkyl$Q^2$ (wherein $Q^2$ is as defined herein).

5. The compound according to claim 3 or claim 4 wherein $R^{2a}$ is methoxy.

6. The compound according to claim 1 selected from:
7-{[1-(acetylmethyl)piperidin-4-yl]methoxy}-6-methoxy-4-[(3-methyl-1H-indol-5-yl)oxy]quinazoline,
7-{[1-(acetylmethyl)piperidin-4-yl]methoxy}-6-methoxy-4-[(2-methyl-1H-indol-5-yl)oxy]quinazoline,
6-methoxy-4-[(3-methyl-1H-indol-5-yl)oxy]-7-{[1-(pyrrolidin-1-ylacetyl)piperidin-4-yl]methoxy}quinazoline,
6-methoxy-4-[(2-methyl-1H-indol-5-yl)oxy]-7-{[1-(pyrrolidin-1-ylacetyl)piperidin-4-yl]methoxy}quinazoline,
6-methoxy-4-[(2-methyl-1H-indol-5-yl)oxy]-7-[2-(tetrahydro-5H-[1,3]dioxolo[4,5-c]pyrrol-5-yl)ethoxy]quinazoline,
6-methoxy-4-[(3-methyl-1H-indol-5-yl)oxy]-7-[2-(tetrahydro-5H-[1,3]dioxolo[4,5-c]pyrrol-5-yl)ethoxy]quinazoline,
4-[(2,3-dimethyl-1H-indol-5-yl)oxy]-6-methoxy-7-[2-(tetrahydro-5H-[1,3]dioxolo[4,5-c]pyrrol-5-yl)ethoxy]quinazoline,
4-[(4-fluoro-2-methyl-1H-indol-5-yl)oxy]-6-methoxy-7-[2-(tetrahydro-5H-[1,3]dioxolo[4,5-c]pyrrol-5-yl)ethoxy]quinazoline,
7-{2-[4-(acetylmethyl)piperazin-1-yl]ethoxy}-4-[(2,3-dimethyl-1H-indol-5-yl)oxy]-6-methoxyquinazoline,
7-{2-[4-(acetylmethyl)piperazin-1-yl]ethoxy}-6-methoxy-4-[(3-methyl-1H-indol-5-yl)oxy]quinazoline,
7-{2-[4-(acetylmethyl)piperazin-1-yl]ethoxy}-6-methoxy-4-[(2-methyl-1H-indol-5-yl)oxy]quinazoline,
7-{2-[4-(acetylmethyl)piperazin-1-yl]ethoxy}-4-[(4-fluoro-2-methyl-1H-indol-5-yl)oxy]-6-methoxyquinazoline,
6-methoxy-4-[(2-methyl-1H-indol-5-yl)oxy]-7-{2-[4-(pyrrolidin-1-ylacetyl)piperazin-1-yl]ethoxy}quinazoline,
7-{[1-(acetylmethyl)piperidin-4-yl]oxy}-6-methoxy-4-[(2-methyl-1H-indol-5-yl)oxy]quinazoline, and
7-{[1-(acetylmethyl)piperidin-4-yl]oxy}-4-[(4-fluoro-2-methyl-1H-indol-5-yl)oxy]-6-methoxyquinazoline,
and pharmaceutically-acceptable salts thereof.

7. A pharmaceutical composition which comprises a compound of the formula IIb as defined in claim 1 or a pharmaceutically acceptable salt thereof, in association with a pharmaceutically acceptable excipient or carrier.

* * * * *